(12) United States Patent
Bischoff et al.

(10) Patent No.: US 9,220,716 B2
(45) Date of Patent: Dec. 29, 2015

(54) METHODS AND COMPOSITIONS FOR THE TREATMENT OF PROLIFERATIVE VASCULAR DISORDERS

(75) Inventors: Joyce Bischoff, Weston, MA (US); Shoshana Greenberger, Modiin (IL)

(73) Assignee: Children's Medical Center Corporation, Boston, MA (US)

( * ) Notice: Subject to any disclaimer, the term of this patent is extended or adjusted under 35 U.S.C. 154(b) by 0 days.

(21) Appl. No.: 13/558,850

(22) Filed: Jul. 26, 2012

(65) Prior Publication Data
US 2013/0029950 A1   Jan. 31, 2013

Related U.S. Application Data

(60) Provisional application No. 61/511,799, filed on Jul. 26, 2011.

(51) Int. Cl.
| | |
|---|---|
| *A61K 31/573* | (2006.01) |
| *A61K 45/06* | (2006.01) |
| *A61K 31/436* | (2006.01) |
| *A61K 31/138* | (2006.01) |
| *A61K 31/165* | (2006.01) |
| *A61K 31/5377* | (2006.01) |

(52) U.S. Cl.
CPC .............. *A61K 31/573* (2013.01); *A61K 31/138* (2013.01); *A61K 31/165* (2013.01); *A61K 31/436* (2013.01); *A61K 31/5377* (2013.01); *A61K 45/06* (2013.01)

(58) Field of Classification Search
None
See application file for complete search history.

(56) References Cited

U.S. PATENT DOCUMENTS

2003/0170287 A1 *   9/2003   Prescott ................... 424/423

OTHER PUBLICATIONS

Greenberger et al ("Corticosteroid Suppression of VEGF-A in Infantile Hemangioma-Derived Stem Cells." New England Journal of Medicine. 2010; 362(11):1005-1013).*
Petroulakis et al ("mTOR signaling: implications for cancer and anticancer therapy." British Journal of Cancer. 2006; 94:195-199).*
Dutcher ("Mammalian Target of Rapamycin inhibition." Clin Cancer Res 2004; 10:6382S-6387S).*
Buckmiller et al ("Propranolol for Airway Hemangiomas: Case Report of Novel Treatment" The Laryngoscope. 2009; 119:2051-2054).*
Bennett M.L. et al., "Oral Corticosteroid Use Is Effective for Cutaneous Hemangiomas: An Evidence-Based Evaluation," Arch Dermatol. 137(9):1208-1213 (Sep. 2001).
Boon, LM et al., "Complications of Systemic Corticosteroid Therapy for Problematic Hemangioma," Plast Reconstr Surg. 104(6):1616-1623 (Nov. 1999).
Frieden, I.J. et al., "Propranolol for Infantile Hemangiomas: Promise, Peril, Pathogenesis," Pediatric Dermatology 26 (5):642-644 (2009).
Leaute-Labreze, C. et al., "Propranolol for Severe Hemangiomas of Infancy," N Engl J Ned 358(24):2649-2651 (Jun. 12, 2008).
Siegfried, E.C. et al. "More on Propranolol for Hemangiomas of Infancy," N Engl J Ned 359:(26):2846-2847 (Dec. 25, 2008).
Loan, FL et al., Kidney International 63: 917-926 (2003) "Rapamycin is an effective inhibitor of human renal cancer metastasis.".

* cited by examiner

*Primary Examiner* — Marcos Sznaidman
*Assistant Examiner* — Rayna B Rodriguez
(74) *Attorney, Agent, or Firm* — Nixon Peabody LLP

(57) ABSTRACT

The technology described herein is directed to methods and compositions for the treatment of proliferative vascular disorders, e.g. hemangioma. In some aspects, the methods and compositions described herein related to a mTOR inhibitor or nifedipine.

14 Claims, 16 Drawing Sheets

SEQUENCE LISTING

<160> NUMBER OF SEQ ID NOS: 24

<210> SEQ ID NO 1
<211> LENGTH: 8733
<212> TYPE: DNA
<213> ORGANISM: Homo sapiens

<400> SEQUENCE: 1

| | | | | | | |
|---|---|---|---|---|---|---|
| gctcccggct | tagaggacag | cggggaaggc | gggcggtggg | gcaggggcc | tgaagcggcg | 60 |
| gtaccggtgc | tggcggcggc | agctgaggcc | ttggccgaag | ccgcgcgaac | ctcagggcaa | 120 |
| gatgcttgga | accggacctg | ccgccgccac | caccgctgcc | accacatcta | gcaatgtgag | 180 |
| cgtcctgcag | cagtttgcca | gtggcctaaa | gagccggaat | gaggaaacca | gggccaaagc | 240 |
| cgccaaggag | ctccagcact | atgtcaccat | ggaactccga | gagatgagtc | aagaggagtc | 300 |
| tactcgcttc | tatgaccaac | tgaaccatca | cattttttgaa | ttggtttcca | gctcagatgc | 360 |
| caatgagagg | aaaggtggca | tcttggccat | agctagcctc | ataggagtgg | aaggtgggaa | 420 |
| tgccacccga | attggcagat | tgccaacta | tcttcggaac | ctcctcccct | ccaatgaccc | 480 |
| agttgtcatg | gaaatggcat | ccaaggccat | tggccgtctt | gccatggcag | gggacacttt | 540 |
| taccgctgag | tacgtggaat | ttgaggtgaa | gcgagccctg | aatggctgg | gtgctgaccg | 600 |
| caatgagggc | cggagacatg | cagctgtcct | ggttctccgt | gagctggcca | tcagcgtccc | 660 |
| taccttcttc | ttccagcaag | tgcaacccctt | ctttgacaac | attttttgtgg | ccgtgtggga | 720 |
| ccccaaacag | gccatccgtg | agggagctgt | agccgccctt | cgtgcctgtc | tgattctcac | 780 |
| aacccagcgt | gagccgaagg | agatgcagaa | gcctcagtgg | tacaggcaca | catttgaaga | 840 |
| agcagagaag | ggatttgatg | agaccttggc | caaagagaag | ggcatgaatc | gggatgatcg | 900 |
| gatccatgga | gccttgttga | tccttaacga | gctggtccga | atcagcagca | tggagggaga | 960 |
| gcgtctgaga | gaagaaatgg | aagaaatcac | acagcagcag | ctggtacacg | acaagtactg | 1020 |
| caaagatctc | atgggcttcg | gaacaaaacc | tcgtcacatt | accccttca | ccagtttcca | 1080 |
| ggctgtacag | ccccagcagt | caaatgcctt | ggtggggctg | ctggggtaca | gctctcacca | 1140 |
| aggcctcatg | ggatttggga | cctcccccag | tccagctaag | tccaccctgg | tggagagccg | 1200 |
| gtgttgcaga | gacttgatgg | aggagaaatt | tgatcaggtg | tgccagtggg | tgctgaaatg | 1260 |
| caggaatagc | aagaactcgc | tgatccaaat | gacaatcctt | aatttgttgc | cccgcttggc | 1320 |
| tgcattccga | ccttctgcct | tcacagatac | ccagtatctc | caagatacca | tgaaccatgt | 1380 |
| cctaagctgt | gtcaagaagg | agaaggaacg | tacagcggcc | ttccaagccc | tggggctact | 1440 |
| ttctgtggct | gtgaggtctg | agtttaaggt | ctatttgcct | cgcgtgctgg | acatcatccg | 1500 |
| agcggccctg | cccccaaagg | acttcgccca | taagaggcag | aaggcaatgc | aggtggatgc | 1560 |
| cacagtcttc | acttgcatca | gcatgctggc | tcgagcaatg | gggccaggca | tccagcagga | 1620 |
| tatcaaggag | ctgctggagc | ccatgctggc | agtgggacta | agccctgccc | tcactgcagt | 1680 |
| gctctacgac | ctgagccgtc | agattccaca | gctaaagaag | gacattcaag | atggctact | 1740 |
| gaaaatgctg | tccctggtcc | ttatgcacaa | acccccttcgc | cacccaggca | tgcccaaggg | 1800 |
| cctggcccat | cagctggcct | ctcctggcct | cacgaccctc | cctgaggcca | gcgatgtggg | 1860 |
| cagcatcact | cttgccctcc | gaacgcttgg | cagctttgaa | tttgaaggcc | actctctgac | 1920 |
| ccaatttgtt | cgccactgtg | cggatcattt | cctgaacagt | gagcacaagg | agatccgcat | 1980 |
| ggaggctgcc | cgcacctgct | cccgcctgct | cacaccctcc | atccacctca | tcagtggcca | 2040 |
| tgctcatgtg | gttagccaga | ccgcagtgca | agtggtggca | gatgtgctta | gcaaactgct | 2100 |

```
cgtagttggg ataacagatc ctgaccctga cattcgctac tgtgtcttgg cgtccctgga    2160
cgagcgcttt gatgcacacc tggcccaggc ggagaacttg caggccttgt ttgtggctct    2220
gaatgaccag gtgtttgaga tccgggagct ggccatctgc actgtgggcc gactcagtag    2280
catgaaccct gcctttgtca tgcctttcct gcgcaagatg ctcatccaga ttttgacaga    2340
gttggagcac agtgggattg gaagaatcaa agagcagagt gcccgcatgc tggggcacct    2400
ggtctccaat gcccccgac  tcatccgccc ctacatggag cctattctga aggcattaat    2460
tttgaaactg aaagatccag accctgatcc aaacccaggt gtgatcaata atgtcctggc    2520
aacaatagga gaattggcac aggttagtgg cctggaaatg aggaaatggg ttgatgaact    2580
ttttattatc atcatggaca tgctccagga ttcctctttg ttggccaaaa ggcaggtggc    2640
tctgtggacc ctgggacagt tggtggccag cactggctat gtagtagagc cctacaggaa    2700
gtaccctact ttgcttgagg tgctactgaa ttttctgaag actgagcaga accagggtac    2760
acgcagagag gccatccgtg tgttagggct tttaggggct ttggatcctt acaagcacaa    2820
agtgaacatt ggcatgatag accagtcccg ggatgcctct gctgtcagcc tgtcagaatc    2880
caagtcaagt caggattcct ctgactatag cactagtgaa atgctggtca catgggaaa   2940
cttgcctctg gatgagttct acccagctgt gtccatggtg gccctgatgc ggatcttccg    3000
agaccagtca ctctctcatc atcacaccat ggttgtccag gccatcacct tcatcttcaa    3060
gtccctggga ctcaaatgtg tgcagttcct gccccaggtc atgcccacgt tccttaacgt    3120
cattcgagtc tgtgatgggg ccatccggga attttgttc  cagcagctgg aatgttggt    3180
gtcctttgtg aagagccaca tcagaccttta tatggatgaa atagtcaccc tcatgagaga    3240
attctgggtc atgaacacct caattcagag cacgatcatt cttctcattg agcaaattgt    3300
ggtagctctt gggggtgaat ttaagctcta cctgccccag ctgatcccac acatgctgcg    3360
tgtcttcatg catgacaaca gcccaggccg cattgtctct atcaagttac tggctgcaat    3420
ccagctgttt ggcgccaacc tggatgacta cctgcattta ctgctgcctc ctattgttaa    3480
gttgtttgat gcccctgaag ctccactgcc atctcgaaag gcagcgctag agactgtgga    3540
ccgcctgacg gagtccctgg atttcactga ctatgcctcc cggatcattc ccctattgt    3600
tcgaacactg accagagcc  cagaactgcg ctccacagcc atggacacgc tgtcttcact    3660
tgttttcag  ctggggaaga agtaccaaat tttcattcca atggtgaata agttctggt    3720
gcgacaccga atcaatcatc agcgctatga tgtgctcatc tgcagaattg tcaagggata    3780
cacacttgct gatgaagagg aggatccttt gatttaccag catcggatgc ttaggagtgg    3840
ccaaggggat gcattggcta gtggaccagt ggaaacagga cccatgaaga aactgcacgt    3900
cagcaccatc aacctccaaa aggcctgggg cgctgccagg agggtctcca agatgactg    3960
gctggaatgg ctgagacggc tgagcctgga gctgctgaag gactcatcat cgccctccct    4020
gcgctcctgc tgggccctgg cacaggccta aacccgatg  gccagggatc tcttcaatgc    4080
tgcatttgtg tcctgctggt ctgaactgaa tgaagatcaa caggatgagc tcatcagaag    4140
catcgagttg gccctcacct cacaagacat cgctgaagtc acacagaccc tcttaaactt    4200
ggctgaattc atggaacaca gtgacaaggg ccccctgcca ctgagagatg acaatggcat    4260
tgttctgctg ggtgagagag ctgccaagtg ccgagcatat gccaaagcac tacactacaa    4320
agaactggag ttccagaaag gccccacccc tgccattcta gaatctctca tcagcattaa    4380
taataagcta cagcagccgg aggcagcggc cggagtgtta gaatatgcca tgaaacactt    4440
tggagagctg gagatccagg ctacctggta tgagaaactg cacgagtggg aggatgccct    4500
```

```
tgtggcctat gacaagaaaa tggacaccaa caaggacgac ccagagctga tgctgggccg      4560
catgcgctgc ctcgaggcct tgggggaatg gggtcaactc caccagcagt gctgtgaaaa      4620
gtggaccctg gttaatgatg agacccaagc caagatggcc cggatggctg ctgcagctgc      4680
atggggttta ggtcagtggg acagcatgga agaatacacc tgtatgatcc ctcgggacac      4740
ccatgatggg gcattttata gagctgtgct ggcactgcat caggacctct tctccttggc      4800
acaacagtgc attgacaagg ccagggacct gctggatgct gaattaactg cgatggcagg      4860
agagagttac agtcgggcat atggggccat ggtttcttgc cacatgctgt ccgagctgga      4920
ggaggttatc cagtacaaac ttgtccccga gcgacgagag atcatccgcc agatctggtg      4980
ggagagactg cagggctgcc agcgtatcgt agaggactgg cagaaaatcc ttatggtgcg      5040
gtcccttgtg gtcagccctc atgaagacat gagaacctgg ctcaagtatg caagcctgtg      5100
cggcaagagt ggcaggctgg ctcttgctca taaaacttta gtgttgctcc tgggagttga      5160
tccgtctcgg caacttgacc atcctctgcc aacagttcac cctcaggtga cctatgccta      5220
catgaaaaac atgtggaaga gtgcccgcaa gatcgatgcc ttccagcaca tgcagcattt      5280
tgtccagacc atgcagcaac aggcccagca tgccatcgct actgaggacc agcagcataa      5340
gcaggaactg cacaagctca tggcccgatg cttcctgaaa cttggagagt ggcagctgaa      5400
tctacagggc atcaatgaga gcacaatccc caaagtgctg cagtactaca gcgccgccac      5460
agagcacgac cgcagctggt acaaggcctg gcatgcgtgg gcagtgatga acttcgaagc      5520
tgtgctacac tacaaacatc agaaccaagc ccgcgatgag aagaagaaac tgcgtcatgc      5580
cagcggggcc aacatcacca acgccaccac tgccgccacc acggccgcca ctgccaccac      5640
cactgccagc accgagggca gcaacagtga gagcgaggcc gagagcaccg agaacagccc      5700
caccccatcg ccgctgcaga agaaggtcac tgaggatctg tccaaaaccc tcctgatgta      5760
cacggtgcct gccgtccagg gcttcttccg ttccatctcc ttgtcacgag caacaacct      5820 ccaggataca ctcagagttc tcaccttatg gtttgattat ggtcactggc cagatgtcaa      5880
tgaggcctta gtggaggggg tgaaagccat ccagattgat acctggctac aggttatacc      5940
tcagctcatt gcaagaattg atacgcccag acccttggtg ggacgtctca ttcaccagct      6000
tctcacagac attggtcggt accacccccca ggccctcatc tacccactga cagtggcttc      6060
taagtctacc acgacagccc ggcacaatgc agccaacaag attctgaaga acatgtgtga      6120
gcacagcaac ccctggtcc agcaggccat gatggtgagc gaggagctga tccgagtggc      6180
catcctctgg catgagatgt ggcatgaagg cctggaagag gcatctcgtt tgtactttgg      6240
ggaaaggaac gtgaaaggca tgtttgaggt gctggagccc ttgcatgcta tgatggaacg      6300
gggcccccag actctgaagg aaacatcctt taatcaggcc tatggtcgag atttaatgga      6360
ggcccaagag tggtgcagga agtacatgaa atcagggaat gtcaaggacc tcacccaagc      6420
ctgggacctc tattatcatg tgttccgacg aatctcaaag cagctgcctc agctcacatc      6480
cttagagctg caatatgttt ccccaaaact tctgatgtgc cgggaccttg aattggctgt      6540
gccaggaaca tatgaccccca accagccaat cattcgcatt cagtccatag caccgtcttt      6600
gcaagtcatc acatccaagc agaggcccccg gaaattgaca cttatgggca gcaacggaca      6660
tgagtttgtt ttccttctaa aaggccatga agatctgcgc caggatgagc gtgtgatgca      6720
gctcttcggc ctggttaaca cccttctggc caatgaccca acatctcttc ggaaaaacct      6780
cagcatccag agatacgctg tcatcccttt atcgaccaac tcgggcctca ttggctgggt      6840
tccccactgt gacacactgc acgccctcat ccggactac agggagaaga agaagatcct      6900
```

-continued

| | |
|---|---|
| tctcaacatc gagcatcgca tcatgttgcg gatggctccg gactatgacc acttgactct | 6960 |
| gatgcagaag gtggaggtgt ttgagcatgc cgtcaataat acagctgggg acgacctggc | 7020 |
| caagctgctg tggctgaaaa gccccagctc cgaggtgtgg tttgaccgaa gaaccaatta | 7080 |
| tacccgttct ttagcggtca tgtcaatggt tgggtatatt ttaggcctgg agatagaca | 7140 |
| cccatccaac ctgatgctgg accgtctgag tgggaagatc ctgcacattg actttgggga | 7200 |
| ctgctttgag gttgctatga cccgagagaa gtttccagag aagattccat ttagactaac | 7260 |
| aagaatgttg accaatgcta tggaggttac aggcctggat ggcaactaca gaatcacatg | 7320 |
| ccacacagtg atggaggtgc tgcgagagca caaggacagt gtcatggccg tgctggaagc | 7380 |
| cttttgtctat gaccccttgc tgaactggag gctgatggac acaaatacca aaggcaacaa | 7440 |
| gcgatcccga acgaggacgg attcctactc tgctggccag tcagtcgaaa ttttggacgg | 7500 |
| tgtggaactt ggagagccag cccataagaa acggggacc acagtgccag aatctattca | 7560 |
| ttctttcatt ggacacggtt tggtgaaacc agaggcccta aataagaaag ctatccagat | 7620 |
| tattaacagg gttcgagata agctcactgg tcgggacttc tctcatgatg acactttgga | 7680 |
| tgttccaacg caagttgagc tgctcatcaa acaagcgaca tcccatgaaa acctctgcca | 7740 |
| gtgctatatt ggctggtgcc cttttctgta actggaggcc cagatgtgcc catcacgttt | 7800 |
| tttctgaggc ttttgtactt tagtaaatgc ttccactaaa ctgaaaccat ggtgagaaag | 7860 |
| tttgactttg ttaaatattt tgaaatgtaa atgaaaagaa ctactgtata ttaaaagttg | 7920 |
| gtttgaacca actttctagc tgctgttgaa gaatatattg tcagaaacac aaggcttgat | 7980 |
| ttggttccca ggacagtgaa acatagtaat accacgtaaa tcaagccatt cattttgggg | 8040 |
| aacagaagat ccataacttt agaaatacgg gttttgactt aactcacaag agaactcatc | 8100 |
| ataagtactt gctgatggaa gaatgaccta gttgctcctc tcaacatggg tacagcaaac | 8160 |
| tcagcacagc caagaagcct caggtcgtgg agaacatgga ttaggatcct agactgtaaa | 8220 |
| gacacagaag atgctgacct caccccctgcc acctatccca agacctcact ggtctgtgga | 8280 |
| cagcagcaga atgtttgca agataggcca aaatgagtac aaaaggtctg tcttccatca | 8340 |
| gacccagtga tgctgcgact cacacgcttc aattcaagac ctgaccgcta gtagggaggt | 8400 |
| ttattcagat cgctggcagc ctcggctgag cagatgcaca gaggggatca ctgtgcagtg | 8460 |
| ggaccaccct cactggcctt ctgcagcagg ttctgggat gttttcagtg gtcaaaatac | 8520 |
| tctgtttaga gcaagggctc agaaaacaga atactgtca tggaggtgct gaacacaggg | 8580 |
| aaggtctggt acatattgga aattatgagc agaacaaata ctcaactaaa tgcacaaagt | 8640 |
| ataaagtgta gccatgtcta gacaccatgt tgtatcagaa taattttttgt gccaataaat | 8700 |
| gacatcagaa ttttaaacat atgtaaaaaa aaa | 8733 |

<210> SEQ ID NO 2
<211> LENGTH: 2549
<212> TYPE: PRT
<213> ORGANISM: Homo sapiens

<400> SEQUENCE: 2

Met Leu Gly Thr Gly Pro Ala Ala Ala Thr Thr Ala Ala Thr Thr Ser
1               5                   10                  15

Ser Asn Val Ser Val Leu Gln Gln Phe Ala Ser Gly Leu Lys Ser Arg
            20                  25                  30

Asn Glu Glu Thr Arg Ala Lys Ala Ala Lys Glu Leu Gln His Tyr Val
        35                  40                  45

```
Thr Met Glu Leu Arg Glu Met Ser Gln Glu Glu Ser Thr Arg Phe Tyr
    50              55                  60

Asp Gln Leu Asn His His Ile Phe Glu Leu Val Ser Ser Asp Ala
 65              70                  75              80

Asn Glu Arg Lys Gly Gly Ile Leu Ala Ile Ala Ser Leu Ile Gly Val
                85                  90                  95

Glu Gly Gly Asn Ala Thr Arg Ile Gly Arg Phe Ala Asn Tyr Leu Arg
            100                 105                 110

Asn Leu Leu Pro Ser Asn Asp Pro Val Val Met Glu Met Ala Ser Lys
        115                 120                 125

Ala Ile Gly Arg Leu Ala Met Ala Gly Asp Thr Phe Thr Ala Glu Tyr
    130                 135                 140

Val Glu Phe Glu Val Lys Arg Ala Leu Glu Trp Leu Gly Ala Asp Arg
145                 150                 155                 160

Asn Glu Gly Arg Arg His Ala Ala Val Leu Val Leu Arg Glu Leu Ala
                165                 170                 175

Ile Ser Val Pro Thr Phe Phe Gln Gln Val Gln Pro Phe Phe Asp
            180                 185                 190

Asn Ile Phe Val Ala Val Trp Asp Pro Lys Gln Ala Ile Arg Glu Gly
        195                 200                 205

Ala Val Ala Ala Leu Arg Ala Cys Leu Ile Leu Thr Thr Gln Arg Glu
    210                 215                 220

Pro Lys Glu Met Gln Lys Pro Gln Trp Tyr Arg His Thr Phe Glu Glu
225                 230                 235                 240

Ala Glu Lys Gly Phe Asp Glu Thr Leu Ala Lys Glu Lys Gly Met Asn
                245                 250                 255

Arg Asp Asp Arg Ile His Gly Ala Leu Leu Ile Leu Asn Glu Leu Val
                260                 265                 270

Arg Ile Ser Ser Met Glu Gly Glu Arg Leu Arg Glu Glu Met Glu Glu
            275                 280                 285

Ile Thr Gln Gln Gln Leu Val His Asp Lys Tyr Cys Lys Asp Leu Met
    290                 295                 300

Gly Phe Gly Thr Lys Pro Arg His Ile Thr Pro Phe Thr Ser Phe Gln
305                 310                 315                 320

Ala Val Gln Pro Gln Gln Ser Asn Ala Leu Val Gly Leu Leu Gly Tyr
                325                 330                 335

Ser Ser His Gln Gly Leu Met Gly Phe Gly Thr Ser Pro Ser Pro Ala
                340                 345                 350

Lys Ser Thr Leu Val Glu Ser Arg Cys Cys Arg Asp Leu Met Glu Glu
            355                 360                 365

Lys Phe Asp Gln Val Cys Gln Trp Val Leu Lys Cys Arg Asn Ser Lys
    370                 375                 380

Asn Ser Leu Ile Gln Met Thr Ile Leu Asn Leu Leu Pro Arg Leu Ala
385                 390                 395                 400

Ala Phe Arg Pro Ser Ala Phe Thr Asp Thr Gln Tyr Leu Gln Asp Thr
                405                 410                 415

Met Asn His Val Leu Ser Cys Val Lys Lys Glu Lys Gly Arg Thr Ala
                420                 425                 430

Ala Phe Gln Ala Leu Gly Leu Leu Ser Val Ala Val Arg Ser Glu Phe
    435                 440                 445

Lys Val Tyr Leu Pro Arg Val Leu Asp Ile Ile Arg Ala Ala Leu Pro
450                 455                 460
```

```
Pro Lys Asp Phe Ala His Lys Arg Gln Lys Ala Met Gln Val Asp Ala
465                 470                 475                 480

Thr Val Phe Thr Cys Ile Ser Met Leu Ala Arg Ala Met Gly Pro Gly
            485                 490                 495

Ile Gln Gln Asp Ile Lys Glu Leu Leu Glu Pro Met Leu Ala Val Gly
        500                 505                 510

Leu Ser Pro Ala Leu Thr Ala Val Leu Tyr Asp Leu Ser Arg Gln Ile
    515                 520                 525

Pro Gln Leu Lys Lys Asp Ile Gln Asp Gly Leu Leu Lys Met Leu Ser
530                 535                 540

Leu Val Leu Met His Lys Pro Leu Arg His Pro Gly Met Pro Lys Gly
545                 550                 555                 560

Leu Ala His Gln Leu Ala Ser Pro Gly Leu Thr Thr Leu Pro Glu Ala
                565                 570                 575

Ser Asp Val Gly Ser Ile Thr Leu Ala Leu Arg Thr Leu Gly Ser Phe
            580                 585                 590

Glu Phe Glu Gly His Ser Leu Thr Gln Phe Val Arg His Cys Ala Asp
    595                 600                 605

His Phe Leu Asn Ser Glu His Lys Glu Ile Arg Met Glu Ala Ala Arg
610                 615                 620

Thr Cys Ser Arg Leu Leu Thr Pro Ser Ile His Leu Ile Ser Gly His
625                 630                 635                 640

Ala His Val Val Ser Gln Thr Ala Val Gln Val Ala Asp Val Leu
                645                 650                 655

Ser Lys Leu Leu Val Val Gly Ile Thr Asp Pro Asp Pro Asp Ile Arg
            660                 665                 670

Tyr Cys Val Leu Ala Ser Leu Asp Glu Arg Phe Asp Ala His Leu Ala
            675                 680                 685

Gln Ala Glu Asn Leu Gln Ala Leu Phe Val Ala Leu Asn Asp Gln Val
        690                 695                 700

Phe Glu Ile Arg Glu Leu Ala Ile Cys Thr Val Gly Arg Leu Ser Ser
705                 710                 715                 720

Met Asn Pro Ala Phe Val Met Pro Phe Leu Arg Lys Met Leu Ile Gln
                725                 730                 735

Ile Leu Thr Glu Leu Glu His Ser Gly Ile Gly Arg Ile Lys Glu Gln
            740                 745                 750

Ser Ala Arg Met Leu Gly His Leu Val Ser Asn Ala Pro Arg Leu Ile
    755                 760                 765

Arg Pro Tyr Met Glu Pro Ile Leu Lys Ala Leu Ile Leu Lys Leu Lys
770                 775                 780

Asp Pro Asp Pro Asp Pro Asn Pro Gly Val Ile Asn Asn Val Leu Ala
785                 790                 795                 800

Thr Ile Gly Glu Leu Ala Gln Val Ser Gly Leu Glu Met Arg Lys Trp
        805                 810                 815

Val Asp Glu Leu Phe Ile Ile Met Asp Met Leu Gln Asp Ser Ser
            820                 825                 830

Leu Leu Ala Lys Arg Gln Val Ala Leu Trp Thr Leu Gly Gln Leu Val
            835                 840                 845

Ala Ser Thr Gly Tyr Val Val Glu Pro Tyr Arg Lys Tyr Pro Thr Leu
    850                 855                 860

Leu Glu Val Leu Leu Asn Phe Leu Lys Thr Glu Gln Asn Gln Gly Thr
865                 870                 875                 880
```

```
Arg Arg Glu Ala Ile Arg Val Leu Gly Leu Leu Gly Ala Leu Asp Pro
                885                 890                 895

Tyr Lys His Lys Val Asn Ile Gly Met Ile Asp Gln Ser Arg Asp Ala
        900                 905                 910

Ser Ala Val Ser Leu Ser Glu Ser Lys Ser Ser Gln Asp Ser Ser Asp
            915                 920                 925

Tyr Ser Thr Ser Glu Met Leu Val Asn Met Gly Asn Leu Pro Leu Asp
        930                 935                 940

Glu Phe Tyr Pro Ala Val Ser Met Val Ala Leu Met Arg Ile Phe Arg
945                 950                 955                 960

Asp Gln Ser Leu Ser His His His Thr Met Val Val Gln Ala Ile Thr
                965                 970                 975

Phe Ile Phe Lys Ser Leu Gly Leu Lys Cys Val Gln Phe Leu Pro Gln
                980                 985                 990

Val Met Pro Thr Phe Leu Asn Val Ile Arg Val Cys Asp Gly Ala Ile
                995                 1000                1005

Arg Glu Phe Leu Phe Gln Gln Leu Gly Met Leu Val Ser Phe Val
    1010                1015                1020

Lys Ser His Ile Arg Pro Tyr Met Asp Glu Ile Val Thr Leu Met
    1025                1030                1035

Arg Glu Phe Trp Val Met Asn Thr Ser Ile Gln Ser Thr Ile Ile
    1040                1045                1050

Leu Leu Ile Glu Gln Ile Val Val Ala Leu Gly Gly Glu Phe Lys
    1055                1060                1065

Leu Tyr Leu Pro Gln Leu Ile Pro His Met Leu Arg Val Phe Met
    1070                1075                1080

His Asp Asn Ser Pro Gly Arg Ile Val Ser Ile Lys Leu Leu Ala
    1085                1090                1095

Ala Ile Gln Leu Phe Gly Ala Asn Leu Asp Asp Tyr Leu His Leu
    1100                1105                1110

Leu Leu Pro Pro Ile Val Lys Leu Phe Asp Ala Pro Glu Ala Pro
    1115                1120                1125

Leu Pro Ser Arg Lys Ala Ala Leu Glu Thr Val Asp Arg Leu Thr
    1130                1135                1140

Glu Ser Leu Asp Phe Thr Asp Tyr Ala Ser Arg Ile Ile His Pro
    1145                1150                1155

Ile Val Arg Thr Leu Asp Gln Ser Pro Glu Leu Arg Ser Thr Ala
    1160                1165                1170

Met Asp Thr Leu Ser Ser Leu Val Phe Gln Leu Gly Lys Lys Tyr
    1175                1180                1185

Gln Ile Phe Ile Pro Met Val Asn Lys Val Leu Val Arg His Arg
    1190                1195                1200

Ile Asn His Gln Arg Tyr Asp Val Leu Ile Cys Arg Ile Val Lys
    1205                1210                1215

Gly Tyr Thr Leu Ala Asp Glu Glu Asp Pro Leu Ile Tyr Gln
    1220                1225                1230

His Arg Met Leu Arg Ser Gly Gln Gly Asp Ala Leu Ala Ser Gly
    1235                1240                1245

Pro Val Glu Thr Gly Pro Met Lys Lys Leu His Val Ser Thr Ile
    1250                1255                1260

Asn Leu Gln Lys Ala Trp Gly Ala Ala Arg Arg Val Ser Lys Asp
    1265                1270                1275
```

-continued

```
Asp Trp Leu Glu Trp Leu Arg Arg Leu Ser Leu Glu Leu Leu Lys
    1280            1285                1290

Asp Ser Ser Pro Ser Leu Arg Ser Cys Trp Ala Leu Ala Gln
    1295            1300                1305

Ala Tyr Asn Pro Met Ala Arg Asp Leu Phe Asn Ala Ala Phe Val
    1310            1315                1320

Ser Cys Trp Ser Glu Leu Asn Glu Asp Gln Asp Glu Leu Ile
    1325            1330                1335

Arg Ser Ile Glu Leu Ala Leu Thr Ser Gln Asp Ile Ala Glu Val
    1340            1345                1350

Thr Gln Thr Leu Leu Asn Leu Ala Glu Phe Met Glu His Ser Asp
    1355            1360                1365

Lys Gly Pro Leu Pro Leu Arg Asp Asp Asn Gly Ile Val Leu Leu
    1370            1375                1380

Gly Glu Arg Ala Ala Lys Cys Arg Ala Tyr Ala Lys Ala Leu His
    1385            1390                1395

Tyr Lys Glu Leu Glu Phe Gln Lys Gly Pro Thr Pro Ala Ile Leu
    1400            1405                1410

Glu Ser Leu Ile Ser Ile Asn Asn Lys Leu Gln Gln Pro Glu Ala
    1415            1420                1425

Ala Ala Gly Val Leu Glu Tyr Ala Met Lys His Phe Gly Glu Leu
    1430            1435                1440

Glu Ile Gln Ala Thr Trp Tyr Glu Lys Leu His Glu Trp Glu Asp
    1445            1450                1455

Ala Leu Val Ala Tyr Asp Lys Lys Met Asp Thr Asn Lys Asp Asp
    1460            1465                1470

Pro Glu Leu Met Leu Gly Arg Met Arg Cys Leu Glu Ala Leu Gly
    1475            1480                1485

Glu Trp Gly Gln Leu His Gln Gln Cys Cys Glu Lys Trp Thr Leu
    1490            1495                1500

Val Asn Asp Glu Thr Gln Ala Lys Met Ala Arg Met Ala Ala Ala
    1505            1510                1515

Ala Ala Trp Gly Leu Gly Gln Trp Asp Ser Met Glu Glu Tyr Thr
    1520            1525                1530

Cys Met Ile Pro Arg Asp Thr His Asp Gly Ala Phe Tyr Arg Ala
    1535            1540                1545

Val Leu Ala Leu His Gln Asp Leu Phe Ser Leu Ala Gln Gln Cys
    1550            1555                1560

Ile Asp Lys Ala Arg Asp Leu Leu Asp Ala Glu Leu Thr Ala Met
    1565            1570                1575

Ala Gly Glu Ser Tyr Ser Arg Ala Tyr Gly Ala Met Val Ser Cys
    1580            1585                1590

His Met Leu Ser Glu Leu Glu Glu Val Ile Gln Tyr Lys Leu Val
    1595            1600                1605

Pro Glu Arg Arg Glu Ile Ile Arg Gln Ile Trp Trp Glu Arg Leu
    1610            1615                1620

Gln Gly Cys Gln Arg Ile Val Glu Asp Trp Gln Lys Ile Leu Met
    1625            1630                1635

Val Arg Ser Leu Val Val Ser Pro His Glu Asp Met Arg Thr Trp
    1640            1645                1650

Leu Lys Tyr Ala Ser Leu Cys Gly Lys Ser Gly Arg Leu Ala Leu
    1655            1660                1665
```

```
Ala His Lys Thr Leu Val Leu Leu Leu Gly Val Asp Pro Ser Arg
1670            1675            1680

Gln Leu Asp His Pro Leu Pro Thr Val His Pro Gln Val Thr Tyr
1685            1690            1695

Ala Tyr Met Lys Asn Met Trp Lys Ser Ala Arg Lys Ile Asp Ala
1700            1705            1710

Phe Gln His Met Gln His Phe Val Gln Thr Met Gln Gln Gln Ala
1715            1720            1725

Gln His Ala Ile Ala Thr Glu Asp Gln Gln His Lys Gln Glu Leu
1730            1735            1740

His Lys Leu Met Ala Arg Cys Phe Leu Lys Leu Gly Glu Trp Gln
1745            1750            1755

Leu Asn Leu Gln Gly Ile Asn Glu Ser Thr Ile Pro Lys Val Leu
1760            1765            1770

Gln Tyr Tyr Ser Ala Ala Thr Glu His Asp Arg Ser Trp Tyr Lys
1775            1780            1785

Ala Trp His Ala Trp Ala Val Met Asn Phe Glu Ala Val Leu His
1790            1795            1800

Tyr Lys His Gln Asn Gln Ala Arg Asp Glu Lys Lys Lys Leu Arg
1805            1810            1815

His Ala Ser Gly Ala Asn Ile Thr Asn Ala Thr Thr Ala Ala Thr
1820            1825            1830

Thr Ala Ala Thr Ala Thr Thr Thr Ala Ser Thr Glu Gly Ser Asn
1835            1840            1845

Ser Glu Ser Glu Ala Glu Ser Thr Glu Asn Ser Pro Thr Pro Ser
1850            1855            1860

Pro Leu Gln Lys Lys Val Thr Glu Asp Leu Ser Lys Thr Leu Leu
1865            1870            1875

Met Tyr Thr Val Pro Ala Val Gln Gly Phe Phe Arg Ser Ile Ser
1880            1885            1890

Leu Ser Arg Gly Asn Asn Leu Gln Asp Thr Leu Arg Val Leu Thr
1895            1900            1905

Leu Trp Phe Asp Tyr Gly His Trp Pro Asp Val Asn Glu Ala Leu
1910            1915            1920

Val Glu Gly Val Lys Ala Ile Gln Ile Asp Thr Trp Leu Gln Val
1925            1930            1935

Ile Pro Gln Leu Ile Ala Arg Ile Asp Thr Pro Arg Pro Leu Val
1940            1945            1950

Gly Arg Leu Ile His Gln Leu Leu Thr Asp Ile Gly Arg Tyr His
1955            1960            1965

Pro Gln Ala Leu Ile Tyr Pro Leu Thr Val Ala Ser Lys Ser Thr
1970            1975            1980

Thr Thr Ala Arg His Asn Ala Ala Asn Lys Ile Leu Lys Asn Met
1985            1990            1995

Cys Glu His Ser Asn Thr Leu Val Gln Gln Ala Met Met Val Ser
2000            2005            2010

Glu Glu Leu Ile Arg Val Ala Ile Leu Trp His Glu Met Trp His
2015            2020            2025

Glu Gly Leu Glu Glu Ala Ser Arg Leu Tyr Phe Gly Glu Arg Asn
2030            2035            2040

Val Lys Gly Met Phe Glu Val Leu Glu Pro Leu His Ala Met Met
2045            2050            2055
```

```
Glu Arg Gly Pro Gln Thr Leu Lys Glu Thr Ser Phe Asn Gln Ala
2060                2065                2070

Tyr Gly Arg Asp Leu Met Glu Ala Gln Glu Trp Cys Arg Lys Tyr
2075                2080                2085

Met Lys Ser Gly Asn Val Lys Asp Leu Thr Gln Ala Trp Asp Leu
2090                2095                2100

Tyr Tyr His Val Phe Arg Arg Ile Ser Lys Gln Leu Pro Gln Leu
2105                2110                2115

Thr Ser Leu Glu Leu Gln Tyr Val Ser Pro Lys Leu Leu Met Cys
2120                2125                2130

Arg Asp Leu Glu Leu Ala Val Pro Gly Thr Tyr Asp Pro Asn Gln
2135                2140                2145

Pro Ile Ile Arg Ile Gln Ser Ile Ala Pro Ser Leu Gln Val Ile
2150                2155                2160

Thr Ser Lys Gln Arg Pro Arg Lys Leu Thr Leu Met Gly Ser Asn
2165                2170                2175

Gly His Glu Phe Val Phe Leu Leu Lys Gly His Glu Asp Leu Arg
2180                2185                2190

Gln Asp Glu Arg Val Met Gln Leu Phe Gly Leu Val Asn Thr Leu
2195                2200                2205

Leu Ala Asn Asp Pro Thr Ser Leu Arg Lys Asn Leu Ser Ile Gln
2210                2215                2220

Arg Tyr Ala Val Ile Pro Leu Ser Thr Asn Ser Gly Leu Ile Gly
2225                2230                2235

Trp Val Pro His Cys Asp Thr Leu His Ala Leu Ile Arg Asp Tyr
2240                2245                2250

Arg Glu Lys Lys Lys Ile Leu Leu Asn Ile Glu His Arg Ile Met
2255                2260                2265

Leu Arg Met Ala Pro Asp Tyr Asp His Leu Thr Leu Met Gln Lys
2270                2275                2280

Val Glu Val Phe Glu His Ala Val Asn Asn Thr Ala Gly Asp Asp
2285                2290                2295

Leu Ala Lys Leu Leu Trp Leu Lys Ser Pro Ser Ser Glu Val Trp
2300                2305                2310

Phe Asp Arg Arg Thr Asn Tyr Thr Arg Ser Leu Ala Val Met Ser
2315                2320                2325

Met Val Gly Tyr Ile Leu Gly Leu Gly Asp Arg His Pro Ser Asn
2330                2335                2340

Leu Met Leu Asp Arg Leu Ser Gly Lys Ile Leu His Ile Asp Phe
2345                2350                2355

Gly Asp Cys Phe Glu Val Ala Met Thr Arg Glu Lys Phe Pro Glu
2360                2365                2370

Lys Ile Pro Phe Arg Leu Thr Arg Met Leu Thr Asn Ala Met Glu
2375                2380                2385

Val Thr Gly Leu Asp Gly Asn Tyr Arg Ile Thr Cys His Thr Val
2390                2395                2400

Met Glu Val Leu Arg Glu His Lys Asp Ser Val Met Ala Val Leu
2405                2410                2415

Glu Ala Phe Val Tyr Asp Pro Leu Leu Asn Trp Arg Leu Met Asp
2420                2425                2430

Thr Asn Thr Lys Gly Asn Lys Arg Ser Arg Thr Arg Thr Asp Ser
2435                2440                2445
```

```
Tyr Ser Ala Gly Gln Ser Val Glu Ile Leu Asp Gly Val Glu Leu
    2450                2455                2460

Gly Glu Pro Ala His Lys Lys Thr Gly Thr Thr Val Pro Glu Ser
    2465                2470                2475

Ile His Ser Phe Ile Gly Asp Gly Leu Val Lys Pro Glu Ala Leu
    2480                2485                2490

Asn Lys Lys Ala Ile Gln Ile Ile Asn Arg Val Arg Asp Lys Leu
    2495                2500                2505

Thr Gly Arg Asp Phe Ser His Asp Asp Thr Leu Asp Val Pro Thr
    2510                2515                2520

Gln Val Glu Leu Leu Ile Lys Gln Ala Thr Ser His Glu Asn Leu
    2525                2530                2535

Cys Gln Cys Tyr Ile Gly Trp Cys Pro Phe Trp
    2540                2545
```

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gccttgccgc cttgctgctc ta                                              22

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gtgctggcct tggtgagg                                                   18

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ccactcagct cttctcct                                                   18

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
agggtaccac ttccacct                                                   18

<210> SEQ ID NO 7
<211> LENGTH: 20
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 7
gggcgttttg ttgttggtct                                              20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gcgcttgttg ccatgaataa                                              20

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gataaagcca aacaacgcaa cg                                           22

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ctagagatcc agcgacccga a                                            21

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
taactacccc ctagacaacg tcca                                         24

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
aagagatgaa tggagcgctc g                                            21

<210> SEQ ID NO 13
<211> LENGTH: 19
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 13
tgcaccacca actgcttag                                                  19

<210> SEQ ID NO 14
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gatgcaggga tgatgttc                                                   18

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
catggtcttc aagcagatgg                                                 20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ctgcgctttc ttcataaacc                                                 20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
cccagaagta tgaccaccag                                                 20

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gcagcttatt gatgaattcg c                                               21

<210> SEQ ID NO 19
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 19
cctggagaat ggtggaagag                                                    20

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
ctgtgtttgt agtgaggatg g                                                  21

<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
agaagccagg gagaaggaaa ccaa                                               24

<210> SEQ ID NO 22
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
tggagctgac caggtcttcc attt                                               24

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
cggaaataac tgagatcacc a                                                  21

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
ttgatggatg acacctggag                                                    20
```

METHODS AND COMPOSITIONS FOR THE TREATMENT OF PROLIFERATIVE VASCULAR DISORDERS

CROSS-REFERENCE TO RELATED APPLICATIONS

This application claims benefit under 35 U.S.C. §119(e) of U.S. Provisional Application No. 61/511,799 filed Jul. 26, 2011, the contents of which are incorporated herein by reference in their entirety.

GOVERNMENT SUPPORT

This invention was made with federal funding under Grant Nos. R01 HL096384 and P01 AR48564 awarded by the National Institutes of Health. The U.S. government has certain rights in the invention.

SEQUENCE LISTING

The instant application contains a Sequence Listing which has been submitted in ASCII format via EFS-Web and is hereby incorporated by reference in its entirety. Said ASCII copy, created on Jul. 20, 2012, is named 71397132.txt and is 39,143 bytes in size

TECHNICAL FIELD

The technology described herein relates to treatments for proliferative vascular disorders, including, for example, hemangioma.

BACKGROUND

Proliferative vascular disorders can result in malformed vasculature, causing not only aesthetic concerns but, dependent upon location, a serious threat to a patient's health. For example, infantile hemangioma (LH) is a common childhood tumor composed of disorganized blood vessels and immature cells. IH results from a disruption of neonatal vasculogenesis, de novo formation of vessels from progenitor cells, angiogenesis, and a sprouting of new vessels from pre-existing vasculature. Although benign and usually a harmless tumor, some IH deform or destroy facial features and/or obstruct vision and breathing. Forty to eighty percent result in permanent cutaneous residua, which can be disfiguring. Corticosteroids are the traditional first-line therapy, however the adverse effects are numerous (Boon et al., Plast Reconstr Surg 1999 104:1616-1623) and approximately 16% of hemangiomas do not respond (Bennett et al., Arch Dermatol 2001 137:1208-1213). Propranolol has recently been introduced as a treatment for IH (Leaute-Labreze et al., N Engl J Med 2008 358:2649-2651) (Siegfried et al., N Engl J Med 2008 359:2846). However, its use is not without risks, and not all tumors respond (Frieden and Drolet. Pediatr Dermatol 2009 26:642-644). More effective therapies could improve outcomes and/or shorten treatment duration, thereby reducing the risk of adverse side effects.

SUMMARY

The technology described herein is directed to methods and compositions relating to the treatment of proliferative vascular disorders, e.g. hemangiomas. Aspects of the technology described herein are based on the inventors' discovery that while current treatments (e.g. corticosteroids and propranolol) may inhibit vessel formation, they have no apparent therapeutic effect upon a stem cell population derived from or present in the diseased tissue (referred to herein as "hemangioma stem cells" or "HemSCs"). Described herein is the inventors' discovery and identification of compounds which inhibit the self-renewal, proliferation, and vasculogenic potential of these HemSCs, as well as modifying their differentiation potential. These compounds are referred to collectively herein as HemSC inhibitors. Accordingly, provided herein are methods and compositions for to the treatment of proliferative vascular disorders relating to HemSC inhibitors.

In one aspect, the technology described herein relates to a method of treating a proliferative vascular disorder, the method comprising: administering a HemSC inhibitor; and, optionally, administering a steroid and/or a beta-blocker.

In some embodiments, the HemSC inhibitor can be selected from the group consisting of: an mTOR inhibitor and nifedipine. In some embodiments, the mTOR inhibitor can be selected from the group consisting of: everolimus; temisrolimus; and rapamycin.

In some embodiments, the steroid can be a corticosteroid. In some embodiments, the corticosteroid can be selected from the group consisting of: dexamethasone; prednisone; prednisolone; triamcinolone; clobetasol propionate; betamethasone valerate; betamethasone dipropionate; and mometasone furoate.

In some embodiments, the beta-blocker can be selected from the group consisting of: atenolol; nadolol; propranolol and timolol.

In some embodiments, the i) HemSC inhibitor and ii) the steroid and/or beta-blocker can be administered concomitantly.

In some embodiments, the proliferative vascular disorder can be a vascular malformation. In some embodiments, the proliferative vascular disorder can be a vascular tumor. In some embodiments, the proliferative vascular disorder can be selected from the group consisting of: hemangioma; verrucous hemangioma; nevoid hemangioma; senile hemangioma; kaposiform hemangioendothelioma; pyogenic granuloma and congenital hemangioma. In some embodiments, the proliferative vascular disorder can be infantile hemangioma.

In some embodiments, one or more of the compounds can be administered systemically. In some embodiments, one or more of the compounds can be administered orally. In some embodiments, one or more of the compounds can be administered intralesionally. In some embodiments, one or more of the compounds can be administered topically.

In one aspect, the technology described herein relates to a pharmaceutical composition comprising i) a HemSC inhibitor and ii) a steroid and/or beta-blocker. In some embodiments, the composition can further comprise a pharmaceutically acceptable carrier.

In some embodiments, the HemSC inhibitor can be selected from the group consisting of: an mTOR inhibitor and nifedipine. In some embodiments, the mTOR inhibitor can be selected from the group consisting of: everolimus; temisrolimus; and rapamycin.

In some embodiments, the steroid can be a corticosteroid. In some embodiments, the corticosteroid can be selected from the group consisting of: dexamethasone; prednisone; prednisolone; triamcinolone; clobetasol propionate; betamethasone valerate; betamethasone dipropionate; and mometasone furoate.

In some embodiments, the beta-blocker can be selected from the group consisting of: atenolol; nadolol; propranolol and timolol.

In some embodiments, the composition can be administered systemically. In some embodiments, the composition can be administered orally. In some embodiments, the composition can be administered intralesionally. In some embodiments, the composition can be administered topically.

BRIEF DESCRIPTION OF THE DRAWINGS

FIG. 1A depicts dose-response curves of HemSCs (squares), NHDF (triangles), and BM-MSCs (circles) treated with Rapamycin. Error bars denote standard deviation (SD) (n=32). FIG. 1B depicts a graph of the quantification of PCNA-positive cells in HemSCs treated with Rapamycin. Error bars denote SD (n=8). *P<0.05 compared with the non-treated group. FIG. 1C depicts the results of a Western blot for phospho4EBP-1(S65) and total 4EBP-1 in HemSCs serum-starved for 24 hours, pretreated with vehicle alone ("0") or rapamycin for 20 minutes and then stimulated with media containing serum and growth factors for 30 minutes. FIG. 1D depicts a graph of the bands in FIG. 1C quantified using ImageJ; normalized to β-actin.

FIG. 2A depicts a graph of mean vessel density (MVD) (erythrocyte-filled vessels). Mean value determined from explants±the standard error of mean (SEM). N=6-8/group *P<0.05 compared with vehicle-injected group. **P<0.05 compared with 0.1 mg/kg-injected group. FIG. 2B depicts a graph of MVD of Matrigel explants from mice injected systemically with Rapamycin, Everolimus or Temsirolimus. Bars and * as in FIG. 2A. N=6/group. FIG. 2C depicts a graph of MVD in Matrigel explants from mice injected with Rapamycin pre-treated HemSCs. Bars and * as in (FIG. 2A). N=7/group.

FIG. 3A depicts a graph of cellular proliferation of HemSCs treated with increasing doses of Roscovitine. Bars denote the SD (n=32). FIG. 3B depicts a graph of MVD analysis of Matrigel explants. Bars denote mean value determined from all explants±the SEM. N=8-10/group *P<0.05 compared with the DMSO-pre-treated group. Experiment was repeated twice with similar results.

FIG. 4A depicts a graph of HemSCs pre-treated with Rapamycin or DMSO for 4 days; number of clones with >10 cells after 9 days. FIG. 4B depicts a graph of the percentage of clones from FIG. 4A that expanded to the indicated number of cells/well. FIG. 4C depicts a graph of the results of quantitative PCR of LPL and C/EBP-α in HemSCs in adipogenic medium±Rapamycin. FIG. 4D depicts a graph of the results of quantitative PCR of smMHC and SM22 in HemSCs±Rapamycin. HemSCs co-cultured with cbEPCs, positive control. FIG. 4E depicts the results of a Western blot for SM22 and αSMA in HemSCs±Rapamycin. HemSCs co-cultured with cbEPCs, positive control. FIG. 4F depicts a schematic of the experimental design for FIG. 4G. FIG. 4G depicts a graph of MVD of explants treated as shown in FIG. 4F. Mean value±SEM. N=7-8/group. *P<0.05.

FIG. 5A depicts a graph of the quantification of microbubble perfusion (contrast intensity above baseline) for individual mice injected with vehicle (dark grey lines) or Rapamycin (light grey lines). FIG. 5B depicts a graph of the mean change of perfusion from day 7 to day 17 in vehicle or Rapamycin-injected mice. Error bars denote SEM. N=6/group *P<0.05 compared with vehicle-injected group. FIG. 5C depicts a graph of MVD analysis of Matrigel explants. Bars denote mean value determined from all explants±the SEM. N=6/group. *P<0.05 compared with the DMSO-pre-treated group. Experiment was repeated twice with similar results.

FIG. 6A depicts a graph of quantitative ELISA analysis of VEGF-A protein in conditioned media of Rapamycin treated HemSCs. FIG. 6B depicts a graph of quantitative PCR analysis of the VEGF-A mRNA expression in HemSCs incubated with Rapamycin or dexamethasone (200 nM). FIG. 6C depicts an image of the results of protein array analysis of 43 pro-angiogenic cytokines in conditioned media of HemSCs incubated with Rapamycin. FIG. 6D depicts a graph of MVD analysis of Matrigel explants at Day 7 of mice systemically injected with dexamethasone, Rapamycin or the combination. Bars denote mean value determined from all explants±the SEM. N=6/group *P<0.05.

FIG. 9 depicts microvessel density (MVD) quantification of Matrigel explants at day 7. Lumens with red blood cells were counted.

FIG. 10A depicts a graph of quantitative RT-PCR performed on HemSC incubated with rapamycin for 5 days analyzed for the mRNA expression of SMC markers. FIG. 10B depicts graphs of the effect of nifedipine on spontaneous $Ca^{2+}$ oscillations in HemSC treated with Rapamycin or DMSO for 6 days. Each line indicates the whole-cell $Ca^{2+}$ changes in an individual cell. As reported for human mesenchymal stem cells (Sun et al., 2007), HemSC displayed spontaneous intracellular calcium oscillations. Exposure to nifedipine led to cessation of oscillations in Rapamycin-treated cells but not in DMSO-treated cells, indicating the expression of L-type voltage gated channels in these cells.

FIG. 11A depicts a graph of cell number of cbEPCs treated for 48 hours with Rapamycin or (20 ng/ml) DMSO as a control, in the presence of either VEGF-A (37.5 ng/ml), PLGF-1 (37.5 ng/ml) or the combination. Cell number was quantified by automatic microscopy and software analysis. Bars denote the standard deviation with n=32 for each treatment combination. FIG. 11B depicts a graph of cell number of cbEPCs treated for 48 hours with Everolimus (20 ng/ml), Temsirolimus (200 ng/ml) or DMSO as a control, in the presence of VEGF-A (37.5 ng/ml) or PLGF-1 (37.5 ng/ml). Cell number was quantified by automatic microscopy and software analysis. Bars denote the standard deviation with n=32 for each treatment combination. FIG. 11C depicts a graph of quantitative ELISA analysis of PLGF-1 protein secreted from HemECs and Human Dermal Microvascular Endothelial Cells (HDMECs) following 48 hours of incubation with Rapamycin. FIG. 11D depicts a graph of the dose-response of Rapamycin on PLGF-1 mRNA expression in HemECs. Quantitative RT-PCR analyses of HemECs PLGF-1 expression following 48 hours of incubation with Rapamycin at the indicated concentration. FIG. 11E depicts a graph of the dose-response of Rapamycin on PLGF-1 protein secretion from HemECs. PLGF-1 was measured by quantitative ELISA analysis following 48 hours of incubation with Rapamycin at the indicated concentration.

DETAILED DESCRIPTION

Figure 1A:
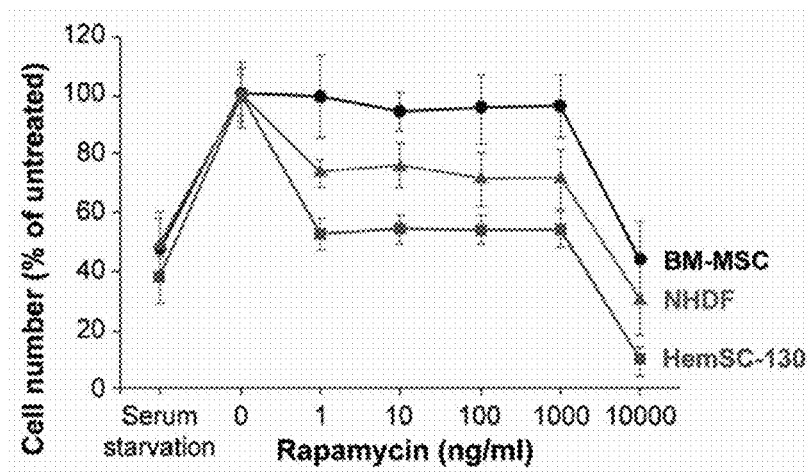
FIGS. 1A-1D demonstrate that rapamycin selectively inhibits the proliferation of HemSCs.

Embodiments of the technology described herein are based on the inventors' discovery of HemSC inhibitor compounds which inhibit the growth and proliferations of stem cells associated with proliferative vascular disorders, thereby reducing vasculogenesis by a mechanism not utilized by current therapies such as corticosteroids. Furthermore, as demonstrated herein, in some embodiments, the HemSC inhibitors identified by the inventors are able to synergize with existing treatments (e.g. corticosteroids) for proliferative vascular disorders (e.g. hemangioma) such that a combination therapy produces a markedly improved therapeutic result as compared to administration of a single agent.

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

For convenience, certain terms employed herein, in the specification, examples and appended claims are collected here.

The term "synergize" as used herein refers to the effect observed when two or more compounds, administered to the same subject, can effect a response which is greater in magnitude than the mere addition of the responses observed for each of the compounds when they are administered to subjects independently.

The terms "decrease", "reduced", "reduction", or "inhibit" are all used herein generally to mean a decrease by a statistically significant amount. However, for avoidance of doubt, "reduced", "reduction", "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g. absent level or non-detectable level as compared to a reference level), or any decrease between 10-100% as compared to a reference level. In the context of a marker or symptom, term refers to a statistically significant decrease in such level. The decrease can be, for example, at least 10%, at least 20%, at least 30%, at least 40% or more, and is preferably down to a level accepted as within the normal range for an individual without such disorder.

The terms "increased", "increase", "enhance", or "activate" are all used herein to generally mean an increase by a statically significant amount; for the avoidance of doubt, the terms "increased", "increase", "enhance", or "activate" mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In some embodiments, the subject is a mammal, e.g., a primate, e.g., a human. The terms, "individual," "patient" and "subject" are used interchangeably herein.

Preferably, the subject is a mammal. The mammal can be a human, non-human primate, mouse, rat, dog, cat, horse, or cow, but is not limited to these examples. Mammals other than humans can be advantageously used as subjects that represent animal models of proliferative vascular disorders. A subject can be male or female.

A subject can be one who has been previously diagnosed with or identified as suffering from or having a condition in need of treatment (e.g. a proliferative vascular disorder), or one or more complications related to such a condition, and optionally, have already undergone treatment for a proliferative vascular disorder or the one or more complications related to a proliferative vascular disorder. Alternatively, a subject can also be one who has not been previously diagnosed as having a proliferative vascular disorder or one or more complications related to a proliferative vascular disorder. For example, a subject can be one who exhibits one or more risk factors for a proliferative vascular disorder or one or more complications related to a proliferative vascular disorder or a subject who does not exhibit risk factors.

A "subject in need" of treatment for a particular condition can be a subject having that condition, diagnosed as having that condition, or at risk of developing that condition.

A "tumor" as used herein refers to an uncontrolled growth of cells which interferes with the normal functioning of the bodily organs and systems. A subject that has a tumor is a subject having objectively measurable tumor cells present in the subject's body. Included in this definition are benign and malignant cancers, as well as dormant tumors or micrometastases.

As used herein, the term "vascular" refers to the circulatory system of an organism. As such, "vascular" can refer to arteries, veins, and capillaries, as well as specialized organs that are closely associated with the circulatory system, e.g. the heart.

As used herein, the term "proteins" and "polypeptides" are used interchangeably herein to designate a series of amino acid residues connected to the other by peptide bonds between the alpha-amino and carboxy groups of adjacent residues. The terms "protein", and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing.

As used herein, the term "nucleic acid" or "nucleic acid sequence" refers to any molecule, preferably a polymeric molecule, incorporating units of ribonucleic acid, deoxyribonucleic acid or an analog thereof. The nucleic acid can be either single-stranded or double-stranded. A single-stranded nucleic acid can be one strand nucleic acid of a denatured double-stranded DNA. Alternatively, it can be a single-stranded nucleic acid not derived from any double-stranded DNA. In one aspect, the template nucleic acid is DNA. In another aspect, the template is RNA. Suitable nucleic acid molecules are DNA, including genomic DNA or cDNA. Other suitable nucleic acid molecules are RNA, including mRNA.

As used herein, the terms "treat," "treatment," "treating," or "amelioration" refer to therapeutic treatments, wherein the object is to reverse, alleviate, ameliorate, inhibit, slow down or stop the progression or severity of a condition associated with a proliferative vascular disease or disorder, e.g. tumor growth. The term "treating" includes reducing or alleviating at least one adverse effect or symptom of a condition, disease or disorder associated with a proliferative vascular disorder. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality, whether detectable or undetectable. The term "treatment" of a disease also includes providing relief from the symptoms or side-effects of the disease (including palliative treatment).

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "pharmaceutical composition" refers to the active agent in combination with a pharmaceutically acceptable carrier e.g. a carrier commonly used in the pharmaceutical industry.

As used herein, the term "administering," refers to the placement of a compound as disclosed herein into a subject by a method or route which results in at least partial delivery of the agent at a desired site. Pharmaceutical compositions comprising the compounds disclosed herein can be administered by any appropriate route which results in an effective treatment in the subject.

The terms "compound" and "agent" refer to any entity which is normally not present or not present at the levels being administered to a cell, tissue or subject. An agent can be selected from a group comprising: chemicals; small organic or inorganic molecules; nucleic acid sequences; nucleic acid analogues; proteins; peptides; aptamers; peptidomimetic, peptide derivative, peptide analogs, antibodies; intrabodies; biological macromolecules, extracts made from biological materials such as bacteria, plants, fungi, or animal cells or tissues; naturally occurring or synthetic compositions or functional fragments thereof. In some embodiments, the agent is any chemical, entity or moiety, including without limitation synthetic and naturally-occurring non-proteinaceous entities. In certain embodiments the agent is a small molecule having a chemical moiety. For example, chemical moieties include unsubstituted or substituted alkyl, aromatic, or heterocyclyl moieties including macrolides, leptomycins and related natural products or analogues thereof. Agents can be known to have a desired activity and/or property, or can be selected from a library of diverse compounds.

As used herein, the term "small molecule" refers to a chemical agent which can include, but is not limited to, a peptide, a peptidomimetic, an amino acid, an amino acid analog, a polynucleotide, a polynucleotide analog, an aptamer, a nucleotide, a nucleotide analog, an organic or inorganic compound (I.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

The term "statistically significant" or "significantly" refers to statistical significance and generally means a two standard deviation (2SD) below normal, or lower, concentration of the marker.

Other than in the operating examples, or where otherwise indicated, all numbers expressing quantities of ingredients or reaction conditions used herein should be understood as modified in all instances by the term "about." The term "about" when used in connection with percentages can mean±1%.

As used herein the term "comprising" or "comprises" is used in reference to compositions, methods, and respective component(s) thereof, that are essential to the method or composition, yet open to the inclusion of unspecified elements, whether essential or not.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of elements that do not materially affect the basic and novel or functional characteristic(s) of that embodiment.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Definitions of common terms in cell biology and molecular biology can be found in "The Merck Manual of Diagnosis and Therapy", 19th Edition, published by Merck Research Laboratories, 2006 (ISBN 0-911910-19-0); Robert S. Porter et al. (eds.), and The Encyclopedia of Molecular Biology, published by Blackwell Science Ltd., 1994 (ISBN 0-632-02182-9). Definitions of common terms in molecular biology can also be found in Benjamin Lewin, Genes X, published by Jones & Bartlett Publishing, 2009 (ISBN-10: 0763766321); Kendrew et al. (eds.), Molecular Biology and Biotechnology: a Comprehensive Desk Reference, published by VCH Publishers, Inc., 1995 (ISBN 1-56081-569-8) and Current Protocols in Protein Sciences. 2009, Wiley Intersciences, Coligan et al., eds.

Unless otherwise stated, the present invention was performed using standard procedures, as described, for example in Davis et al., Basic Methods in Molecular Biology, Elsevier Science Publishing, Inc., New York, USA (1995); Current Protocols in Protein Science (CPPS) (John E. Coligan, et. al., ed., John Wiley and Sons, Inc.), Current Protocols in Cell Biology (CPCB) (Juan S. Bonifacino et. al. ed., John Wiley and Sons, Inc.), Culture of Animal Cells: A Manual of Basic Technique by R. Ian Freshney, Publisher: Wiley-Liss; 5th edition (2005), and Animal Cell Culture Methods (Methods in Cell Biology, Vol. 57, Jennie P. Mather and David Barnes editors, Academic Press, 1st edition, 1998) which are all incorporated by reference herein in their entireties.

Other terms are defined herein within the description of the various aspects of the invention.

Methods and compositions described herein relate to the treatment of proliferative vascular disorders. As used herein, the term "proliferative vascular disorder" refers to any disease or condition characterized by abnormal vascular structures (e.g. structures not normally present in a healthy subject or malformed structures as compared to a healthy subject) and an abnormally high growth of vascular cells. Non-limiting examples of proliferative vascular disorders include vascular tumors, hemangioma, and proliferative vascular malformations.

Vascular malformations are disorders in which the vasculature is improperly formed, resulting in discolored areas, masses, benign growths, and lesions. In some embodiments, vascular malformations can be proliferative vascular disorders. Non-limiting examples of vascular malformations include slow-flow vascular malformations (e.g. capillary malformation, venous malformation, and lymphatic malformation), fast-flow vascular malformations (e.g. arterial malformation, arteriovenous fistula, and arteriovenous malformation), and combined-complex vascular malformations. Methods of diagnosing vascular malformations are well known in the art, see, e.g. Buckmiller et al. Oral Diseases 2010 16:405-418; Flors et al. RadioGraphics 2011 31:1321-1340; Paltiel et al. Radiology 2000 214:747-754; and Werner et al. Eur Arch Otorhiolaryngol 2001 258:141-9; all of which are incorporated by reference herein in their entireties. Vascular malformations are typically treated with surgical reduction, sclerotherapy, or pulsed light therapy.

In some embodiments, the proliferative vascular disorder can be a hemangioma or vascular tumor. As used herein "hemangioma" refers to a benign, usually self-involuting tumor of the endothelial cells of blood vessels. A hemangioma can comprise an increased number of blood vessels and/or capillaries. The vessels and/or capillaries can comprise blood and be connected to the circulatory system. Hemangiomas can occur anywhere in the body, but are typically found in or on the skin, particularly on the face and neck, or in the liver. Hemangiomas can form in utero (e.g. congenital hemangioma) or after birth. Most hemangiomas appear within a few months of birth. Examples of hemangioma include, but are not limited to: infantile hemangioma, congenital hemangioma, kaposiform hemangioendothelioma, infant nevoid hemangioma ("strawberry naevus"), senile hemangioma ("cherry hemangioma"), arteriovenous hemangioma ("cirsoid aneurysm"), verrucous hemangioma, and pyogenic granuloma. Hemangiomas have also been referred to variously as strawberry hemangioma, capillary hemangioma, and/or cavernous hemangioma. The diagnosis and treatment of hemangiomas and vascular tumors is well known in the art and has been described, for example, in Mulliken, J B; Glowacki, J. Plastic and reconstructive surgery 1982 69 (3): 412-22; Greene, A K. Clinics in plastic surgery 2011 38 (1): 1-5; Ernemann, U. et al. European journal of radiology 2010 75(1): 2-11; and Gupta, A. et al. Clinics in plastic surgery 2011 38 (1): 31-44; which are incorporated by reference herein in their entireties.

Hemangiomas affecting the skin can, in some cases, be diagnosed by visual examination. Other approaches that can aid a physician in detecting and/or diagnosing hemangioma can include ultrasound, MRI, and/or a biopsy. Hemangiomas can be distinguished from numerous similar conditions by immunohistochemical staining for, e.g. GLUT-1. Markers and symptoms of proliferative vascular disorders, e.g. hemangioma can include, but are not limited to tumors of the endothelial cells of blood vessels; an increased number of blood vessels and/or capillaries; discoloration of the skin; GLUT-1 expression; hemosiderin pigmentation; ulceration; and bleeding.

While many hemangiomas will regress without medical intervention, the location and extent of some cases can be harmful or dangerous to the subject's health, e.g. interfere with breathing or vision, or induce bone erosion, high-output heart failure, ulceration, and/or raise the possibility of significant cosmetic injury. Symptoms and complications of hemangioma can include, but are not limited to, ulcerations (break down of the hemangioma), bleeding, occlusion, amblyopia (if the hemangioma is near or in the eye), psychosocial complications, alteration of the subject's appearance, attention and malicious reactions from others, and PHACES syndrome (in the case of segmented hemangiomas of the head and neck). Treatments for hemangioma can include, but are not limited to, laser surgery, pulsed dye laser, corticosteroid therapy, oral corticosteroid therapy, beta-blockers, topical beta-blockers, vincristine, interferon, and surgical removal. Hemangiomas of the vertebrae are typically treated with radiation, surgical removal, and/or by cutting blood flow to the hemangioma. The methods and compositions described herein can be combined with any known treatment for hemangioma.

As described herein, the inventor's have discovered a number of compounds which inhibit the self-renewal, proliferation, and/or vasculogenesis of a population of stem cells associated with a proliferative vascular disease (HemSCs), and/or modulate the differentiation potential of these cells. In some embodiments, these compounds can reduce, or in some instances, reverse abnormal vasculogenesis in a subject having a proliferative vascular disorder. This group of compounds acts upon proliferative vascular disorder cells in a way which can be distinguished from the action of corticosteroids as described herein. Compounds are referred to herein as "HemSC inhibitors." Non-limiting examples of HemSC inhibitors include an mTOR inhibitor (e.g. rapamycin, everolimus, or temsirolimus); nifedipine (e.g. a compound having the structure of Formula XVI); antimycin A; chelidonine monohydrate; lycorine hydrochloride; ionomycin; LY-294,002; cerulenin; and monensin sodium. In some embodiments, a HemSC inhibitor can be an mTOR inhibitor or nifedipine.

Formula XVI

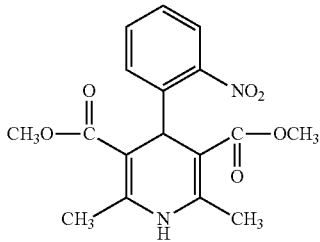

Accordingly, provided herein are methods of treating proliferative vascular disorders with a HemSC inhibitor. In some embodiments, a subject in need of treatment for a proliferative vascular disorder can be administered a HemSC inhibitor. In some embodiments, a subject in need of treatment for a proliferative vascular disorder can be administered a HemSC inhibitor in combination with a steroid and/or beta-blocker. In some embodiments, the HemSC inhibitor can be selected from the group consisting of an mTOR inhibitor (e.g. rapamycin, everolimus, or temsirolimus); nifedipine (e.g. a compound having the structure of Formula XVI); antimycin A; chelidonine monohydrate; lycorine hydrochloride; ionomycin; LY-294,002; cerulenin; and monensin sodium. In some embodiments, the HemSC inhibitor can be selected from the group consisting of an mTOR inhibitor and nifedipine. In some embodiments, multiple HemSC inhibitors can be administered, e.g. concurrently or sequentially. In some embodiments, the method described herein comprises a) selecting a subject having a proliferative vascular disorder, and b) administering a HemSC inhibitor to the subject.

In some embodiments, the HemSC inhibitor can be an mTOR inhibitor. In some embodiments, a subject in need of treatment for a proliferative vascular disorder can be administered an mTOR inhibitor. In some embodiments, a subject in need of treatment for a proliferative vascular disorder can be administered an mTOR inhibitor and a steroid or beta-blocker. In some embodiments, the mTOR inhibitor can be selected from the group consisting of everolimus, temsirolimus, and rapamycin.

As used herein, the term "mTOR inhibitor" refers to an agent that can reduce the expression level and/or activity of mTOR protein and/or mRNA. In some embodiments, an mTOR inhibitor can reduce the expression level of mTOR mRNA. In some embodiments, an mTOR inhibitor can reduce the expression level of mTOR polypeptide. In some embodiments, an mTOR inhibitor can reduce the activity of mTOR polypeptide. As used herein, the term "mTOR" refers to a serine/threonine kinase of the PI3K enzyme family that functions as the catalytic subunit of the mTORC1 and mTORC2 complexes (e.g. NCBI Gene ID: 2475). The sequences of mTOR nucleic acids and polypeptides in a number of species are known in the art (e.g. human mTOR nucleic acid, NCBI Ref Seq: NM_004958, SEQ ID NO: 1 and human mTOR polypeptides, NCBI Ref Seq: NP_004949, SEQ ID NO: 2). mTOR is also referred to as FRAP, RAFT1, and RAPT. mTOR inhibitors can inhibit mTOR via any known mechanism, including, e.g., binding of a competitive inhibitor, binding of a non-competitive inhibitor, increasing the rate of degradation of mTOR polypeptides, blocking the biosynthesis, transcription, and/or translation of mTOR, blocking the targeting of AKT to mTOR, and increasing the inhibition of mTOR by TSC1/2. mTOR inhibition can be determined by methods well known in the art, e.g. by detecting the level of phosphorylation of mTOR targets such as p70-S6 kinase 1 (S6K1), 4EBP1, and Akt, where inhibition or a decreased in the phosphorylation of these targets indicates effective inhibition of mTOR. In certain embodiments, an agent can increase or decrease the expression of a component of the targeted signaling pathway. Components of the mTOR signaling pathway include, but are not limited to RAPTOR, DEPTOR, Rheb, AKT, RICTOR, GβL, and HIF-1. The mTOR signaling pathways have been described in the art, e.g. in Dunlop and Tee Cell Signal 2009 26:827-835; Laplante and Sabatini J Cell Sci 2009 122:3589-3594; Kudchodkar et al. PNAS 2006 103:14182-7; which are incorporated by reference herein in their entireties. Transcriptional assays are well known to those of skill in the art (see e.g. U.S. Pat. Nos. 7,319,933, 6,913,880 which is incorporated herein by reference in its entirety).

Non-limiting examples of mTOR inhibitors for use in the methods and compositions described herein include everolimus (e.g. a compound having the structure of Formula III), temsirolimus (e.g. a compound having the structure of Formula II), rapamycin (e.g. a compound having the structure of Formula I), deforolimus, TOP216, OSI-027, TAFA93, nab-rapamycin, tacrolimus, biolimus, CI-779, ABT-578, AP-23675, BEZ-235, QLT-0447, ABI-009, BC-210, salirasib, AP-23841, AP-23573, KU-0059475, 32-deoxorapamycin, 16-pent-2-ynyloxy-32-deoxorapamycin, 16-pent-2-ynyloxy-32 (S or R)-dihydro-rapamycin, 16-pent-2-ynyloxy-32 (S or R)-dihydro-40-O-(2-hydroxyethyl)-rapamycin, 40-O-(2-hydroxyethyl)-rapamycin, 32-deoxorapamycin; 16-pent-2-ynyloxy-32(S)-dihydrorapamycin; socalledrapalogs; AP23464; PI-103, PP242, PP30, Torin1; and derivatives or pharmaceutically acceptable salts thereof as well as and compounds described in, e.g. U.S. Patent Publications 2011/0178070; 2011/0021515; 2007/0112005; 2011/0054013; International Patent Publications WO98/02441; WO01/14387; WO99/15530; WO07/135,411; WO03/64383; WO96/41807; WO95/16691; WO94/09010; European Patent No. EP1880723; and U.S. Pat. Nos. 8,163,775; 6,329,386; 6,200,985; 6,117,863; 6,015,815; 6,015,809; 6,004,973; 5,985,890; 5,955,457; 5,922,730; 5,912,253; 5,780,462; 5,665,772; 5,637,590; 5,567,709; 5,563,145; 5,559,122; 5,559,120; 5,559,119; 5,559,112; 5,550,133; 5,541,192; 5,541,191; 5,532,355; 5,530,121; 5,530,007; 5,525,610; 5,521,194; 5,519,031; 5,516,780; 5,508,399; 5,508,290; 5,508,286; 5,508,285; 5,504,291; 5,504,204; 5,491,231; 5,489,680; 5,489,595; 5,488,054; 5,486,524; 5,486,523; 5,486,522; 5,484,791; 5,484,790; 5,480,989; 5,480,988; 5,463,048; 5,446,048; 5,434,260; 5,411,967; 5,391,730; 5,389,639; 5,385,910; 5,385,909; 5,385,908; 5,378,836; 5,378,696; 5,373,014; 5,362,718; 5,358,944; 5,346,893; 5,344,833; 5,302,584; 5,262,424; 5,262,423; 5,260,300; 5,260,299; 5,233,036; 5,221,740; 5,221,670; 5,202,332; 5,194,447; 5,177,203; 5,169,851; 5,164,399; 5,162,333; 5,151,413; 5,138,051; 5,130,307; 5,120,842; 5,120,727; 5,120,726; 5,120,725; 5,118,678; 5,118,677; 5,100,883; 5,023,264; 5,023,263; and 5,023,262; which are incorporated by reference herein in their entireties.

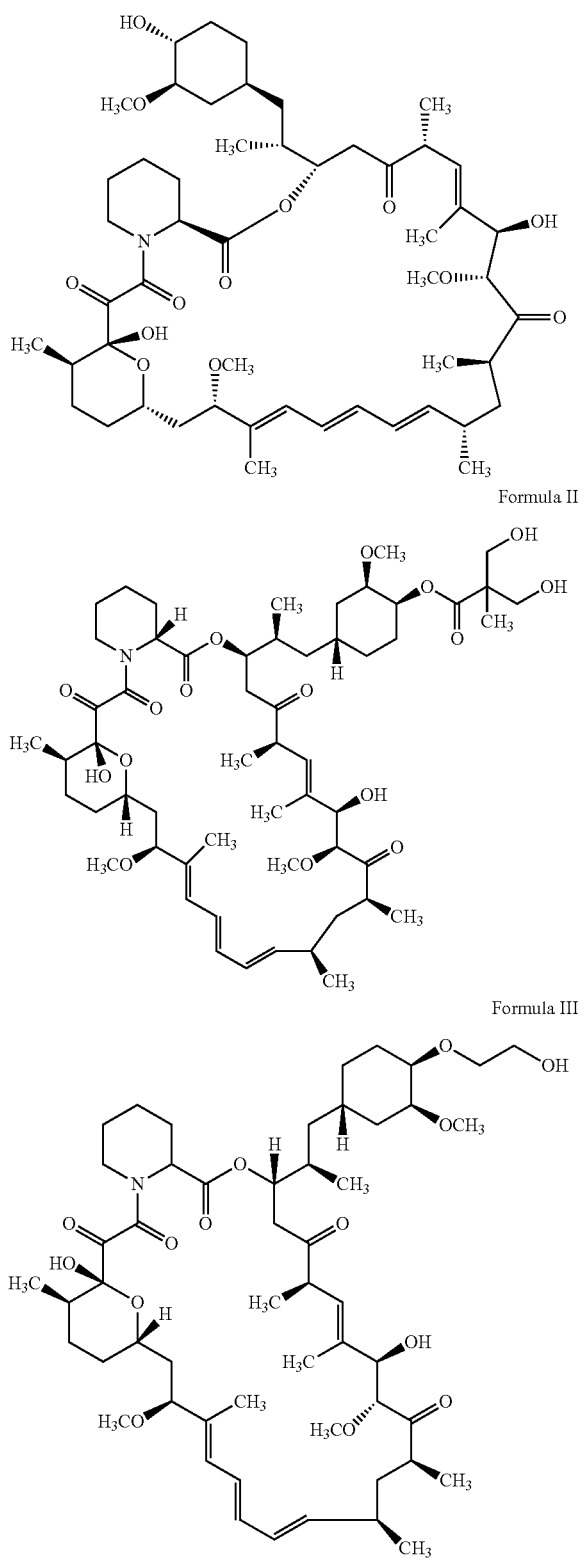

Formula I

Formula II

Formula III

In some embodiments, gene silencing or RNAi can be used to inhibit mTOR. In certain embodiments, contacting a cell with the HemSC inhibitor results in a decrease in the mRNA level in a cell for a target gene (e.g. mTOR) by at least about 10%, e.g., at least about 20%, about 30%, about 40%, about 50%, about 60%, about 70%, about 80%, about 90%, about 95%, about 99%, or more of the mRNA level found in the cell without the presence of the miRNA or RNA interference (RNAi) molecule. In one embodiment, the mRNA levels are decreased by at least about 30%, about 40%, about 50%, about 60%, about 70%, about 80%, about 90%, about 95%, about 99%, or more, i.e., no detectable target mRNA. In certain embodiments, the agent comprises an expression vector or viral vector comprising the RNAi molecule. Methods of assaying the ability of an agent to inhibit translation of a gene, e.g. mTOR, are known to those of ordinary skill in the art. Gene translation can be measured by quantitation of protein expressed from a gene, for example by Western blotting, by an immunological detection of the protein, ELISA (enzyme-linked immunosorbent assay), Western blotting, radioimmunoassay (RIA) or other immunoassays and fluorescence-activated cell analysis (FACS) to detect protein.

As used herein, the term "RNAi" refers to any type of interfering RNA, including but are not limited to, siRNAi, shRNAi, endogenous microRNA and artificial microRNA. For instance, it includes sequences previously identified as siRNA, regardless of the mechanism of down-stream processing of the RNA (i.e. although siRNAs are believed to have a specific method of in vivo processing resulting in the cleavage of mRNA, such sequences can be incorporated into the vectors in the context of the flanking sequences described herein). The term "RNAi" and "RNA interfering" with respect to a HemSC inhibitor are used interchangeably herein.

As used herein a "siRNA" refers to a nucleic acid that forms a double stranded RNA, which double stranded RNA has the ability to reduce or inhibit expression of a gene or target gene when the siRNA is present or expressed in the same cell as the target gene, e.g. mTOR. The double stranded RNA siRNA can be formed by the complementary strands. In one embodiment, a siRNA refers to a nucleic acid that can form a double stranded siRNA. The sequence of the siRNA can correspond to the full length target gene, or a subsequence thereof. Typically, the siRNA is at least about 15-50 nucleotides in length (e.g., each complementary sequence of the double stranded siRNA is about 15-50 nucleotides in length, and the double stranded siRNA is about 15-50 base pairs in length, preferably about 19-30 base nucleotides, preferably about 20-25 nucleotides in length, e.g., 20, 21, 22, 23, 24, 25, 26, 27, 28, 29, or 30 nucleotides in length).

As used herein "shRNA" or "small hairpin RNA" (also called stem loop) is a type of siRNA. In one embodiment, these shRNAs are composed of a short, e.g. about 19 to about 25 nucleotide, antisense strand, followed by a nucleotide loop of about 5 to about 9 nucleotides, and the analogous sense strand. Alternatively, the sense strand can precede the nucleotide loop structure and the antisense strand can follow.

The terms "microRNA" or "miRNA" are used interchangeably herein are endogenous RNAs, some of which are known to regulate the expression of protein-coding genes at the posttranscriptional level. Endogenous microRNA are small RNAs naturally present in the genome which are capable of modulating the productive utilization of mRNA. The term artificial microRNA includes any type of RNA sequence, other than endogenous microRNA, which is capable of modulating the productive utilization of mRNA. MicroRNA sequences have been described in publications such as Lim, et al., Genes & Development, 17, p. 991-1008 (2003), Lim et al Science 299, 1540 (2003), Lee and Ambros Science, 294, 862 (2001), Lau et al., Science 294, 858-861 (2001), Lagos-Quintana et al, Current Biology, 12, 735-739

(2002), Lagos Quintana et al, Science 294, 853-857 (2001), and Lagos-Quintana et al, RNA, 9, 175-179 (2003), which are incorporated by reference. Multiple microRNAs can also be incorporated into a precursor molecule. Furthermore, miRNA-like stem-loops can be expressed in cells as a vehicle to deliver artificial miRNAs and short interfering RNAs (siRNAs) for the purpose of modulating the expression of endogenous genes through the miRNA and or RNAi pathways.

As used herein, "double stranded RNA" or "dsRNA" refers to RNA molecules that are comprised of two strands. Double-stranded molecules include those comprised of a single RNA molecule that doubles back on itself to form a two-stranded structure. For example, the stem loop structure of the progenitor molecules from which the single-stranded miRNA is derived, called the pre-miRNA (Bartel et al. 2004. Cell 116: 281-297), comprises a dsRNA molecule.

As used herein, the term "complementary" or "complementary base pair" refers to A:T and G:C in DNA and A:U in RNA. Most DNA consists of sequences of nucleotide only four nitrogenous bases: base or base adenine (A), thymine (T), guanine (G), and cytosine (C). Together these bases form the genetic alphabet, and long ordered sequences of them contain, in coded form, much of the information present in genes. Most RNA also consists of sequences of only four bases. However, in RNA, thymine is replaced by uridine (U).

In some embodiments, in order to increase nuclease resistance of a HemSC inhibitor comprising a nucleic acid as disclosed herein, one can incorporate non-phosphodiester backbone linkages, as for example methylphosphonate, phosphorothioate or phosphorodithioate linkages or mixtures thereof. Other functional groups may also be joined to the oligonucleoside sequence to instill a variety of desirable properties, such as to enhance uptake of the oligonucleoside sequence through cellular membranes, to enhance stability or to enhance the formation of hybrids with the target nucleic acid, or to promote cross-linking with the target (as with a psoralen photo-cross-linking substituent). See, for example, PCT Publication No. WO 92/02532 which is incorporated herein in by reference.

A HemSC inhibitor can comprise a vector. Many vectors useful for transferring exogenous genes into target mammalian cells are available, e.g. the vectors may be episomal, e.g., plasmids, virus derived vectors such cytomegalovirus, adenovirus, etc., or may be integrated into the target cell genome, through homologous recombination or random integration, e.g., retrovirus derived vectors such MMLV, HIV-1, ALV, etc. Many viral vectors are known in the art and can be used as carriers of a nucleic acid modulatory compound into the cell. For example, constructs containing the modulatory compound may be integrated and packaged into non-replicating, defective viral genomes like Adenovirus, Adeno-associated virus (AAV), or Herpes simplex virus (HSV) or others, including retroviral and lentiviral vectors, for infection or transduction into cells. Alternatively, the construct may be incorporated into vectors capable of episomal replication, e.g. EPV and EBV vectors. The nucleic acid incorporated into the vector can be operatively linked to an expression control sequence when the expression control sequence controls and regulates the transcription and translation of that polynucleotide sequence.

In certain embodiments, the HemSC inhibitor can be a protein or peptide. A peptide agent can be a fragment of a naturally occurring protein, or a mimic or peptidomimetic. Agents in the form of a protein and/or peptide or fragment thereof can be designed to decrease the level and/or activity of mTOR as described herein, i.e. decrease mTOR gene expression or decrease the encoded protein mTOR activity. Such agents are intended to encompass proteins which are normally absent as well as proteins normally endogenously expressed within a cell, e.g. expressed at low levels. Examples of useful proteins are mutated proteins, genetically engineered proteins, peptides, synthetic peptides, recombinant proteins, chimeric proteins, modified proteins and fragments thereof. A decrease in mTOR gene expression or protein mTOR activity can be direct or indirect. In one embodiment, a protein/peptide agent directly binds to a protein which is a component of the targeted polypeptide, or directly binds to a nucleic acid which encodes such a protein.

In one embodiment, protein/peptide agents (including antibodies or fragments thereof) can be assessed for their ability to bind an encoded protein in vitro. Examples of direct binding assays include, but are not limited to, labeled in vitro protein-protein binding assays, electrophoretic mobility shift assays, immunoassays for protein binding, ELISA assays, co-immunoprecipitation assays, competition assays (e.g. with a known binder), and the like. See, e.g., U.S. Pat. Nos. 4,366,241; 4,376,110; 4,517,288; and 4,837,168; and also Bevan et al., Trends in Biotechnology 13:115-122, 1995; Ecker et al., Bio/Technology 13:351-360, 1995; and Hodgson, Bio/Technology 10:973-980, 1992. The agent can also be assayed or identified by detecting a signal that indicates that the agent binds to a protein of interest e.g., fluorescence quenching or FRET. Polypeptides can also be monitored for their ability to bind nucleic acid in vitro, e.g. ELISA-format assays can be a convenient alternative to gel mobility shift assays (EMSA) for analysis of protein binding to nucleic acid. Binding of an agent to an encoded protein provides an indication the agent may increase or decrease protein activity.

In certain embodiments, the HemSC inhibitor can be an antibody, e.g. a neutralizing antibody (See, generally, Hood et al., Immunology, Benjamin, N.Y., 2ND ed. (1984), Harlow and Lane, Antibodies. A Laboratory Manual, Cold Spring Harbor Laboratory (1988) and Hunkapiller and Hood, Nature, 323, 15-16 (1986), which are incorporated herein by reference). Monoclonal antibodies can be prepared using methods well known to those of skill in the art. Methods for intrabody production are well known to those of skill in the art, e.g. as described in WO 2002/086096; which is incorporated herein by reference in its entirety. Antibodies that specifically bind to a target polypeptide, (e.g. a mTOR polypeptide) will usually bind with at least a KD of about 30 µM, preferably at least about 10 µM, and more preferably at least about 3 µM or better, e.g., 100 µM, 50 µM, 1 µM or better.

A HemSC inhibitor can be a naturally occurring protein or a fragment thereof, e.g. a decoy protein. Such agents can be obtained from a natural source, e.g., a cell or tissue lysate. The agents can also be peptides, e.g., peptides of from about 5 to about 30 amino acids, with from about 5 to about 20 amino acids being preferred and from about 7 to about 15 being particularly preferred. The peptides can be digests of naturally occurring proteins, random peptides, "biased" random peptides, decoy proteins, dominant negative proteins, etc. In some methods, the agents are polypeptides or proteins.

A HemSC inhibitor can function directly in the form in which it is administered. Alternatively, the agent can be modified or utilized intracellularly to produce something which is an inhibitor of mTOR as described herein, e.g. introduction of a nucleic acid sequence into the cell and its transcription resulting in the production of an inhibitor of mTOR gene expression or protein activity.

Agents can be produced recombinantly using methods well known to those of skill in the art (see Sambrook et al., Molecular Cloning: A Laboratory Manual (3 ed.), Cold Spring Harbor Laboratory Press, Cold Spring Harbor, N.Y., USA (2001)).

HemSC inhibitors can be synthesized and/or isolated according to methods well known in the art and are available commercially, e.g. nifedipine (Cat No. N7634; Sigma-Aldrich; St. Louis, Mo.) or rapamycin (Cat No. R8781; Sigma-Aldrich; St. Louis, Mo.).

In some embodiments, a HemSC inhibitor can be administered in any combination with, e.g. concurrently or sequentially, with a steroid and/or a beta-blocker. In some embodiments, a HemSC inhibitor, a steroid and a beta-blocker can be administered. In embodiments where multiple compounds are administered (e.g. a HemSC inhibitor and a steroid), the compounds can be administered at varying times and/or for varying durations.

In some embodiments, the method described herein comprises a) selecting a subject having a proliferative vascular disorder, b) administering a HemSC inhibitor to the subject, and c) administering a steroid and/or beta-blocker to the subject.

In some embodiments, a HemSC inhibitor can synergize with a steroid and/or beta-blocker with respect to the treatment of a proliferative vascular disorder. This is advantageous in that the effective dose of each compound can be lower, and/or the length of time for which treatment must be administered can be shortened, both of which circumstances can lower the risk of adverse side effects.

In some embodiments, the steroid can be a corticosteroid. As used herein, the term "steroid" refers to a chemical substance comprising three cyclohexane rings and a cyclopentane ring. The rings are arranged to form tetracyclic cyclopentaphenanthrene, i.e. gonane. As used herein, the term "corticosteroid" refers to a class of steroid hormones that are produced in the adrenal cortex or produced synthetically. Corticosteroids are involved in a wide range of physiologic systems such as stress response, immune response and regulation of inflammation, carbohydrate metabolism, protein catabolism, blood electrolyte levels, and behavior. Corticosteroids are generally grouped into four classes, based on chemical structure. Group A corticosteroids (short to medium acting glucocorticoids) include hydrocortisone, hydrocortisone acetate, cortisone acetate, tixocortol pivalate, prednisolone, methylprednisolone, and prednisone. Group B corticosteroids include triamcinolone acetonide, triamcinolone alcohol, mometasone, amcinonide, budesonide, desonide, fluocinonide, fluocinolone acetonide, and halcinonide. Group C corticosteroids include betamethasone, betamethasone sodium phosphate, dexamethasone, dexamethasone sodium phosphate, and fluocortolone. Group D corticosteroids include hydrocortisone-17-butyrate, hydrocortisone-17-valerate, aclometasone dipropionate, betamethasone valerate, betamethasone dipropionate, prednicarbate, clobetasone-17-butyrate, clobetasol-17-propionate, fluocortolone caproate, fluocortolone pivalate, and fluprednidene acetate. Non-limiting examples of corticosteroids include, aldosternone, beclomethasone, beclomethasone dipropionate, betametahasone, betametahasone-21-phosphate disodium, betametahasone valerate, budesonide, clobetasol, clobetasol propionate, clobetasone butyrate, clocortolone pivalate, cortisol, cortisteron, cortisone, deflazacort, dexamethasone, dexamethasone acetate, dexamethasone sodium phosphate, diflorasone diacetate, dihydroxycortison, flucinonide, fludrocortisones acetate, flumethasone, flunisolide, flucionolone acetonide, fluticasone furate, fluticasone propionate, halcinonide, halpmetasone, hydrocortisone, hydroconrtisone acetate, hydrocortisone succinate, 16α-hydroxyprednisolone, isoflupredone acetate, medrysone, methylprednisolone, prednacinolone, predricarbate, prednisolone, prednisolone acetate, prednisolone sodium succinate, prednisone, triamcinolone, triamcinolone, and triamcinolone diacetate. As used herein, the term "corticosteroid" can include, but is not limited to, the following generic and brand name corticosteroids: cortisone (CORTONE™ ACETATE™, ADRESON™, ALTESONA™, CORTELANT™, CORTISTAB™, CORTISYL™, CORTOGEN™, CORTONE™, SCHEROSON™); dexamethasone-oral (DECADRON ORAL™, DEXAMETH™, DEXONE™, HEXADROL-ORAL™, DEXAMETHASONE™ INTENSOL™, DEXONE 0.5™, DEXONE 0.75™, DEXONE 1.5™, DEXONE 4™); hydrocortisone-oral (CORTEF™, HYDROCORTONE™); hydrocortisone cypionate (CORTEF ORAL SUSPENSION™); methylprednisolone-oral (MEDROL-ORAL™); prednisolone-oral (PRELONE™, DELTA-CORTEF™, PEDIAPRED™, ADNISOLONE™, CORTALONE™, DELTACORTRIL™, DELTASOLONE™, DELTASTAB™, DI-ADRESON F™, ENCORTOLONE™, HYDROCORTANCYL™, MEDISOLONE™, METICORTELONE™, OPREDSONE™, PANAAFCORTELONE™, PRECORTISYL™, PRENISOLONA™, SCHERISOLONA™, SCHERISOLONE™); prednisone (DELTASONE™, LIQUID PRED™, METICORTENT™, ORASONE 1™, ORASONE 5™, ORASONE 10™, ORASONE 20™, ORASONE 50™, PREDNICEN-M™, PREDNISONE INTENSOL™, STERAPRED™, STERAPRED DS™, ADASONE™, CARTANCYL™, COLISONE™, CORDROL™, CORTAN™, DACORTIN™, DECORTIN™, DECORTISYL™, DELCORTIN™, DELLACORT™, DELTADOME™, DELTACORTENE™, DELTISONA™, DIADRESON™, ECONOSONE™, ENCORTON™, FERNISONE™, NISONA™, NOVOPREDNISONE™, PANAFCORT™, PANASOL™, PARACORT™, PARMENISON™, PEHACORT™, PREDELTIN™, PREDNICORT™, PREDNICOT™, PREDNIDIB™, PREDNIMENT™, RECTODELT™, ULTRACORTEN™, WINPRED™); triamcinoloneoral (KENACORT™, ARISTOCORT™, ATOLONE™, SHOLOG A™, TRAMACORT-D™, TRIMED™, TRIAMCOT™, TRISTOPLEX™, TRYLONE D™, U-TRI-LONE™). In some embodiments, a corticosteroid can be a corticosteroid which is active when applied topically, including, but not limited to clobetasol propionate, betamethasone valerate, betamethasone dripropionate, and mometasone furoate. In some embodiments, a corticosteroid can be dexamethasone (e.g. a compound having the structure of Formula IV); prednisone (e.g. a compound having the structure of Formula V); prednisolone (e.g. a compound having the structure of Formula VI); triamcinolone (e.g. a compound having the structure of Formula VII); clobetasol propionate (e.g. a compound having the structure of Formula VIII); betamethasone valerate (e.g. a compound having the structure of Formula IX); betamethasone dipropionate (e.g. a compound having the structure of Formula X); or mometasone furoate (e.g. a compound having the structure of Formula XI). Methods of synthesizing steroids and corticosteroids are well known in the art and such compounds are also commercially available, e.g. dexamethasone (Cat. No. D4902, Sigma-Aldrich; St. Louis, Mo.) and predinsone (Cat. No. P6254, Sigma-Aldrich; St. Louis, Mo.).

Formula IV

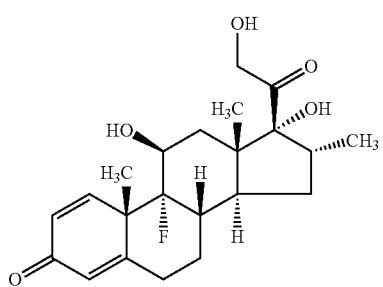

Formula V

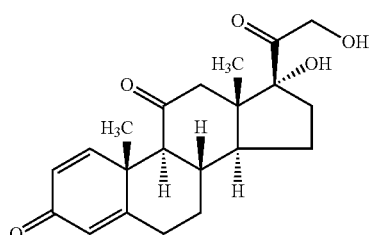

Formula VI

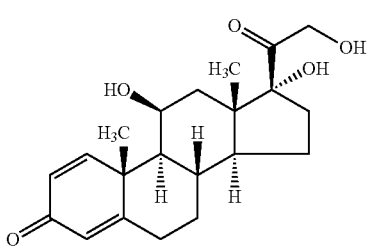

Formula VII

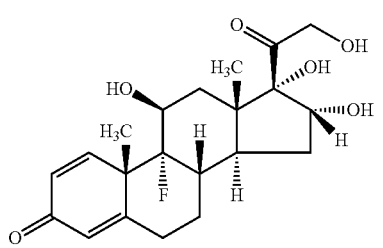

Formula VIII

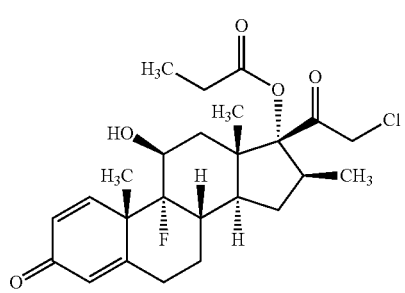

Formula IX

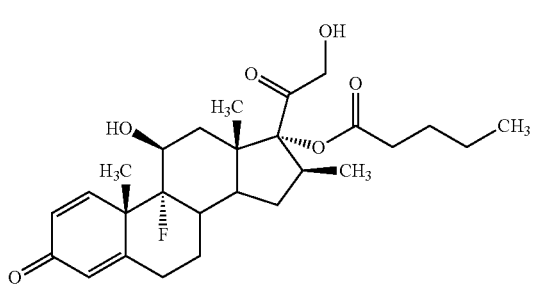

Formula X

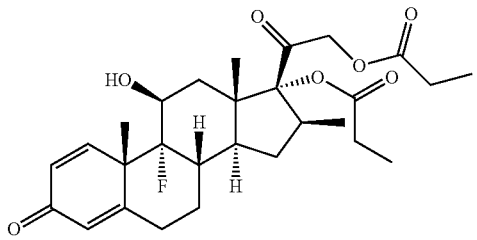

Formula XI

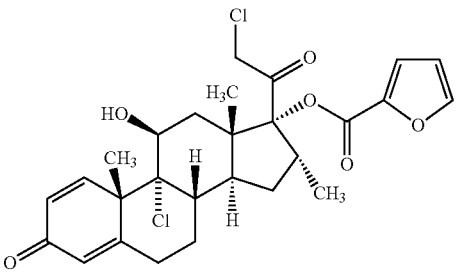

As used herein, "beta-blocker" refers to a chemical which inhibits or blocks the activity of one or more beta-adrengenic receptors. Some beta-blockers antagonize one specific subtype of beta-adrenergic receptors (e.g. a beta-1 selective beta blocker which selectively antagonizes the beta-1 adrenergic receptor), whereas other beta-blockers are non-selective. In some embodiments, a beta-blocker can inhibit the effect of, e.g. noradrenaline or norepinephrine on one or more beta-adrengenic receptors. In context of the technology described herein, the term "beta-blocker" refers to all types of antagonists or inhibitors of beta-adrenergic receptors, regardless of whether the beta-blocker antagonizes one, two or more beta-adrenergic receptors and regardless of whether they affect other processes. Examples of beta-blockers include, but are not limited to: acebutolol, alprenolol, atenolol, betaxolol, bisoprolol, bopindolol, bucindolol, butaxamine, carteolol, carvedilol, celiprolol, esmolol, labetalol, levobunolol, medroxalol, metipranolol, metoprolol, nadolol, nebivolol, nadolol, oxprenolol, penbutolol, pindolol, propafenone, propranolol, sotalol, timolol, eucommia bark, ICI-118,551, and SR59230A. As used herein, the term "beta-blocker" can include, but is not limited to, the following generic and brand name beta-blockers: SOTACORT™, BETAPACE™ (sotalol), NOVO-TIMOL™, APO-TIMOL™, BLOCADREN™ (timolol), BREVIBLOC™ (esmolol), CARTROL™ (carteolol), COREG™ (carvedilol), CORGARD™ (nadolol), INDERAL™ (propranolol), INDERALLA™, APO-PROPRANOLOL™ (propranolol), KERLONE™ (betaxolol), LEVATOL™ (penbutolol), BETALOC™, LOPRESSOR™, NOVOMETOPROLT™ (metoprolol), NORMODYNE™ (labetalol), SECTRAL™ (acebutolol), TENORMIN™, NOVO-ATENOL™ (atenolol), TOPROL-XL™ (metoprolol), TRANDATE™ (labetalol), NOVOPINDOL™, VISKEN™ (pindolol), ZEBETAT™ (bisoprolol), TRASICOR™ (oxprenolol), APOATENOLOL™ (atenolol), and MONITAN™ and SECTRAL™ (acebutolol). In some embodiments, a beta-blocker can be atenolol (e.g. a compound having the structure of Formula XII), nadolol (e.g. a compound having the structure of Formula XIII), propranolol (e.g. a compound having the structure of Formula XIV), or timolol (e.g. a compound having the structure of Formula XV). Methods of synthesizing beta-blockers are well known in the art and such compounds are also commercially available, e.g. timolol (Cat. No. T6394, Sigma-Aldrich; St. Louis, Mo.) and propranolol (Cat. No. P8688, Sigma-Aldrich; St. Louis, Mo.).

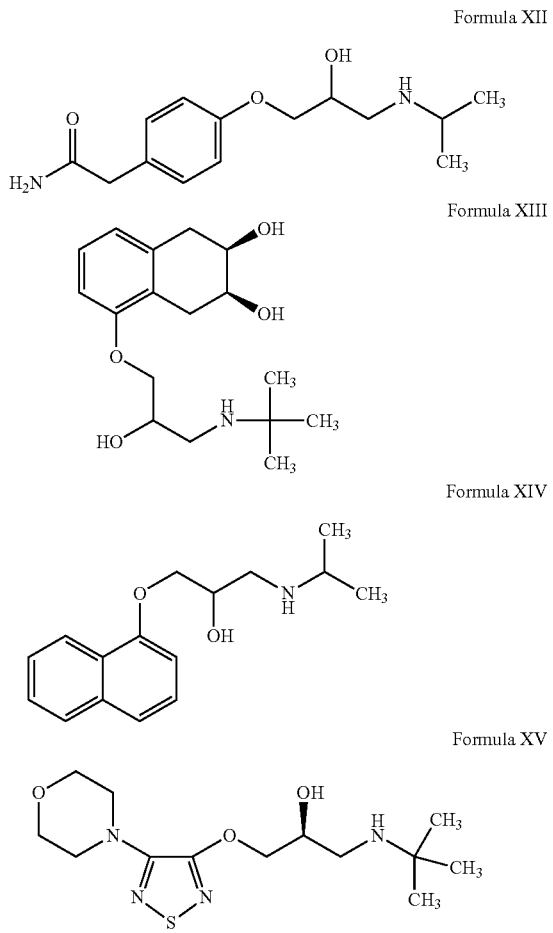

Formula XII

Formula XIII

Formula XIV

Formula XV

In some embodiments, the methods described herein relate to administering to a subject having, or diagnosed as having, a proliferative vascular disorder a HemSC inhibitor, optionally, in combination with a steroid and/or a beta-blocker. Subjects having a proliferative vascular disorder can be identified by a physician using current methods of diagnosing proliferative vascular disorders, as described herein. Symptoms of proliferative vascular disorders which characterize these conditions and aid in diagnosis are well known in the art and include but are not limited to, discolorations of the epidermis or the presence of a vascular tissue tumor. Tests that aid in a diagnosis of proliferative vascular disorders, e.g. hemangioma, include, but are not limited to, ultrasound, MRI, and histochemical examination of biopsies. A family history of hemangiomas can also aid in determining if a subject is likely to have a hemangioma or in making a diagnosis of hemangioma.

The HemSC inhibitor compositions and methods described herein can be administered to a subject having, or diagnosed as having, a proliferative vascular disorder. In some embodiments, the methods described herein comprise administering an effective amount of compositions described herein, e.g. a HemSC inhibitor to a subject in order to alleviate a symptom of a proliferative vascular disorder. As used herein, "alleviating a symptom of a proliferative vascular disorder" is ameliorating any condition or symptom associated with the proliferative vascular disorder, e.g. tumor size, extent of the irregular vasculature, or growth of irregular vasculature. As compared with an equivalent untreated control, such reduction is by at least 5%, 10%, 20%, 40%, 50%, 60%, 80%, 90%, 95%, 99% or more as measured by any standard technique. A variety of means for administering the compositions described herein to subjects are known to those of skill in the art. Such methods can include, but are not limited to oral, parenteral, intravenous, intramuscular, subcutaneous, transdermal, airway (aerosol), pulmonary, cutaneous, topical, injection, intralesionally, or intratumoral administration. Administration can be local or systemic.

In some embodiments, a HemSC inhibitor and a steroid and/or beta-blocker can be administered topically. In some embodiments, at least one of a HemSC inhibitor and a topical steroid (e.g. cloetasol propionate or mometasone furoate) can be administered, and one or both of the compounds can be administered topically. In some embodiments, a HemSC inhibitor and a topical beta-blocker (e.g. timolol) can be administered, and one or both of the compounds can be administered topically. In some embodiments, a HemSC inhibitor, topical steroid, and topical beta-blocker can be administered, and one, two, or all of the compounds can be administered topically.

The term "effective amount" as used herein refers to the amount of a HemSC inhibitor, and optionally, a steroid and/or beta-blocker needed to alleviate at least one or more symptoms of the disease or disorder, and relates to a sufficient amount of pharmacological composition to provide the desired effect. The term "therapeutically effective amount" therefore refers to an amount of a HemSC inhibitor, and optionally, a steroid and/or beta-blocker that is sufficient to effect a particular anti-vasculogenesis effect when administered to a typical subject. An effective amount as used herein in various contexts, would also include an amount sufficient to delay the development of a symptom of the disease, alter the course of a symptom disease (for example but not limited to, slowing the progression of a symptom of the disease), or reverse a symptom of the disease. Thus, it is not generally practicable to specify an exact "effective amount". However, for any given case, an appropriate "effective amount" can be determined by one of ordinary skill in the art using only routine experimentation.

Effective amounts, toxicity, and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dosage can vary depending upon the dosage form employed and the route of administration utilized. The dose ratio between toxic and therapeutic effects is the therapeutic index and can be expressed as the ratio LD50/ED50. Compositions and methods that exhibit large therapeutic indices are preferred. A therapeutically effective dose can be estimated initially from cell culture assays as described herein. Also, a dose can be formulated in animal models to achieve a circulating plasma concentration range that includes the IC50 (i.e., the concentration of the HemSC inhibitor which achieves a half-maximal inhibition of a symptom) as determined in cell culture, or in an appropriate animal model. The level of a HemSC inhibitor in plasma can be measured, for example, by high performance liquid chromatography. The effects of any particular dosage can be monitored by a suitable bioassay, e.g., in vitro or in vivo assay for vasculogenesis or tumor size among others. The dosage can be determined by a physician and adjusted, as necessary, to suit observed effects of the treatment.

In some embodiments, the technology described herein relates to a pharmaceutical composition comprising a HemSC inhibitor, and optionally, a steroid and/or beta-blocker as described herein, and optionally a pharmaceutically acceptable carrier. In some embodiments, the composition can comprise multiple HemSC inhibitors, multiple steroids, multiple beta-blockers, or any combination thereof. In some embodiments, a HemSC inhibitor can be nifedipine. In some embodiments, a HemSC inhibitor can be an mTOR inhibitor, e.g. everolimus, temsirolimus, or rapamycin. In some embodiments, a steroid can be a corticosteroid. In some embodiments, a corticosteroid can be selected from the group consisting of: dexamethasone; prednisone; prednisolone; triamcinolone; clobetasol propionate; betamethasone valerate; betamethasone dipropionate; and mometasone furoate. In some embodiments, a beta-blocker can be selected from the group consisting of: atenolol; nadolol; propranolol and timolol. In some embodiments, the composition can comprise rapamycin and/or dexamethasone. In some embodiments, the composition can be suitable for topical application.

Pharmaceutically acceptable carriers and diluents include saline, aqueous buffer solutions, solvents and/or dispersion media. The use of such carriers and diluents is well known in the art. Some non-limiting examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein. In some embodiments, the carrier inhibits the degradation of the active agent, e.g. a HemSC inhibitor as described herein.

In some embodiments, a HemSC inhibitor, and optionally, a steroid and/or beta-blocker can be administered to a subject topically. In some embodiments, topical dosage forms of the HemSC inhibitor, and optionally, a steroid and/or beta-blocker can include, but are not limited to, creams, lotions, ointments, gels, shampoos, sprays, aerosols, solutions, emulsions, patches, and other forms known to one of skill in the art. See, e.g., Remington: The Science and Practice of Pharmacy, 21st Ed., Lippincott, Williams, and Wilkins Philadelphia Pa. (2005); and Ansel's Pharmaceutical Dosage Forms and Drug Delivery Systems, 9th Ed., Lippincott, Williams, and Wilkins, Philadelphia, Pa. (2011). For non-sprayable topical dosage forms, viscous to semi-solid or solid forms comprising a carrier or one or more excipients compatible with topical application and having a dynamic viscosity preferably greater than water are typically employed. Suitable formulations include, without limitation, solutions, suspensions, emulsions, creams, ointments, powders, liniments, salves, and the like, which are, if desired, sterilized or mixed with auxiliary agents (e.g., preservatives, stabilizers, wetting agents, buffers, or salts) for influencing various properties, such as, for example, osmotic pressure. Other suitable topical dosage forms include sprayable aerosol preparations wherein the active ingredient, e.g. a HemSC inhibitor, preferably in combination with a solid or liquid inert carrier, is packaged in a mixture with a pressurized volatile (e.g., a gaseous propellant, such as freon), or in a squeeze bottle. Moisturizers or humectants can also be added to pharmaceutical compositions and dosage forms if desired. Examples of such additional ingredients are well known in the art. See, e.g., Remington: The Science and Practice of Pharmacy, 21st Ed., Lippincott, Williams, and Wilkins, Philadelphia Pa. (2005).

Transdermal and mucosal dosage forms of the compositions comprising a HemSC inhibitor, and optionally, a steroid and/or beta-blocker can include, but are not limited to, patches, sprays, aerosols, creams, lotions, suppositories, ointments, gels, solutions, emulsions, suspensions, or other forms known to one of skill in the art. See, e.g., Remington: The Science and Practice of Pharmacy, 21st Ed., Lippincott, Williams, and Wilkins, Philadelphia Pa. (2005); and Ansel's Pharmaceutical Dosage Forms and Drug Delivery Systems, 9th Ed., Lippincott, Williams, and Wilkins, Philadelphia, Pa. (2011). Dosage forms suitable for treating mucosal tissues within the oral cavity can be formulated as mouthwashes, as oral gels, or as buccal patches. Additional transdermal dosage forms include "reservoir type" or "matrix type" patches, which can be applied to the skin and worn for a specific period of time to permit the penetration of a desired amount of active ingredient.

Suitable excipients (e.g., carriers and diluents) and other materials that can be used to provide transdermal and mucosal dosage forms encompassed by this disclosure are well known to those skilled in the pharmaceutical arts, and depend on the particular tissue or organ to which a given pharmaceutical composition or dosage form will be applied. With that fact in mind, typical excipients include, but are not limited to water, acetone, ethanol, ethylene glycol, propylene glycol, butane-1,3-diol, isopropyl myristate, isopropyl palmitate, mineral oil, and mixtures thereof, to form dosage forms that are non-toxic and pharmaceutically acceptable. In some embodiments, penetration enhancers can be used to assist in delivering the active ingredients to or across the tissue. Suitable penetration enhancers include, but are not limited to: acetone; various alcohols such as ethanol, oleyl, an tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as TWEEN 80 (polysorbate 80) and SPAN 60 (sorbitan monostearate).

In some embodiments, the pharmaceutical composition comprising a HemSC inhibitor, and optionally, a steroid and/or beta-blocker as described herein can be a parenteral dose form. Since administration of parenteral dosage forms typically bypasses the patient's natural defenses against contaminants, parenteral dosage forms are preferably sterile or capable of being sterilized prior to administration to a patient.

Examples of parenteral dosage forms include, but are not limited to, solutions ready for injection, dry products ready to be dissolved or suspended in a pharmaceutically acceptable vehicle for injection, suspensions ready for injection, and emulsions. In addition, controlled-release parenteral dosage forms can be prepared for administration of a patient, including, but not limited to, administration DUROS®-type dosage forms, and dose-dumping.

Suitable vehicles that can be used to provide parenteral dosage forms of a HemSC inhibitor, and optionally, a steroid and/or beta-blocker as disclosed within are well known to those skilled in the art. Examples include, without limitation: sterile water; water for injection USP; saline solution; glucose solution; aqueous vehicles such as but not limited to, sodium chloride injection, Ringer's injection, dextrose Injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate. Compounds that alter or modify the solubility of a pharmaceutically acceptable salt of a HemSC inhibitor as disclosed herein can also be incorporated into the parenteral dosage forms of the disclosure, including conventional and controlled-release parenteral dosage forms.

Pharmaceutical compositions comprising a HemSC inhibitor, and optionally, a steroid and/or beta-blocker can also be formulated to be suitable for oral administration, for example as discrete dosage forms, such as, but not limited to, tablets (including without limitation scored or coated tablets), pills, caplets, capsules, chewable tablets, powder packets, cachets, troches, wafers, aerosol sprays, or liquids, such as but not limited to, syrups, elixirs, solutions or suspensions in an aqueous liquid, a non-aqueous liquid, an oil-in-water emulsion, or a water-in-oil emulsion. Such compositions contain a predetermined amount of the pharmaceutically acceptable salt of the disclosed compounds, and may be prepared by methods of pharmacy well known to those skilled in the art. See generally, Remington: The Science and Practice of Pharmacy, 21st Ed., Lippincott, Williams, and Wilkins, Philadelphia Pa. (2005).

Conventional dosage forms generally provide rapid or immediate drug release from the formulation. Depending on the pharmacology and pharmacokinetics of the drug, use of conventional dosage forms can lead to wide fluctuations in the concentrations of the drug in a patient's blood and other tissues. These fluctuations can impact a number of parameters, such as dose frequency, onset of action, duration of efficacy, maintenance of therapeutic blood levels, toxicity, side effects, and the like. Advantageously, controlled-release formulations can be used to control a drug's onset of action, duration of action, plasma levels within the therapeutic window, and peak blood levels. In particular, controlled- or extended-release dosage forms or formulations can be used to ensure that the maximum effectiveness of a drug is achieved while minimizing potential adverse effects and safety concerns, which can occur both from under-dosing a drug (i.e., going below the minimum therapeutic levels) as well as exceeding the toxicity level for the drug. In some embodiments, a HemSC inhibitor, and optionally, a steroid and/or beta-blocker can be administered in a sustained release formulation.

Controlled-release pharmaceutical products have a common goal of improving drug therapy over that achieved by their non-controlled release counterparts. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. Kim, Cherng-ju, Controlled Release Dosage Form Design, 2 (Technomic Publishing, Lancaster, Pa.: 2000).

Most controlled-release formulations are designed to initially release an amount of drug (active ingredient) that promptly produces the desired therapeutic effect, and gradually and continually release other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, ionic strength, osmotic pressure, temperature, enzymes, water, and other physiological conditions or compounds.

A variety of known controlled- or extended-release dosage forms, formulations, and devices can be adapted for use with the salts and compositions of the disclosure. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,733,566; and 6,365,185 B1; each of which is incorporated herein by reference. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), or a combination thereof to provide the desired release profile in varying proportions.

As used herein, a "prodrug" refers to compounds that can be converted via some chemical or physiological process (e.g., enzymatic processes and metabolic hydrolysis) to a therapeutic agent. Thus, the term "prodrug" also refers to a precursor of a biologically active compound that is pharmaceutically acceptable. A prodrug can be inactive when administered to a subject, i.e. an ester, but is converted in vivo to an active compound, for example, by hydrolysis to the free carboxylic acid or free hydroxyl. The prodrug compound often offers advantages of solubility, tissue compatibility or delayed release in an organism. The term "prodrug" is also meant to include any covalently bonded carriers, which release the active compound in vivo when such prodrug is administered to a subject. Prodrugs of an active compound may be prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a subject, cleaves to form a free hydroxy, free amino or free mercapto group, respectively. Examples of prodrugs include, but are not limited to, acetate, formate and benzoate derivatives of an alcohol or acetamide, formamide and benzamide derivatives of an amine functional group in the active compound and the like. See Harper, "Drug Latentiation" in Jucker, ed. *Progress in Drug Research* 4:221-294

(1962); Morozowich et al, "Application of Physical Organic Principles to Prodrug Design" in E. B. Roche ed. *Design of Biopharmaceutical Properties through Prodrugs and Analogs*, APHA Acad. Pharm. Sci. 40 (1977); Bioreversible Carriers in Drug in Drug Design, Theory and Application, E. B. Roche, ed., APHA Acad. Pharm. Sci. (1987); *Design of Prodrugs*, H. Bundgaard, Elsevier (1985); Wang et al. "prodrug approaches to the improved delivery of peptide drug" in *Curr. Pharm. Design.* 5(4):265-287 (1999); Pauletti et al. (1997) Improvement in peptide bioavailability: Peptidomimetics and prodrug Strategies, *Adv. Drug. Delivery Rev.* 27:235-256; Mizen et al. (1998) "The Use of Esters as prodrugs for Oral Delivery of (3-Lactam antibiotics," *Pharm. Biotech.* 11:345-365; Gaignault et al. (1996) "Designing Prodrugs and Bioprecursors I. Carrier Prodrugs," *Pract. Med. Chem.* 671-696; Asgharnejad, "Improving Oral Drug Transport", in *Transport Processes in Pharmaceutical Systems*, G. L. Amidon, P. I. Lee and E. M. Topp, Eds., Marcell Dekker, p. 185-218 (2000); Balant et al., "Prodrugs for the improvement of drug absorption via different routes of administration", *Eur. J. Drug Metab. Pharmacokinet.*, 15(2): 143-53 (1990); Balimane and Sinko, "Involvement of multiple transporters in the oral absorption of nucleoside analogues", *Adv. Drug Delivery Rev.*, 39(1-3): 183-209 (1999); Browne, "Fosphenyloin (Cerebyx)", Clin. Neuropharmacol. 20(1): 1-12 (1997); Bundgaard, "Bioreversible derivatization of drugs—principle and applicability to improve the therapeutic effects of drugs", *Arch. Pharm. Chemi* 86(1): 1-39 (1979); Bundgaard H. "Improved drug delivery by the prodrug approach", *Controlled Drug Delivery* 17: 179-96 (1987); Bundgaard H. "Prodrugs as a means to improve the delivery of peptide drugs", Arfv. *Drug Delivery Rev.* 8(1): 1-38 (1992); Fleisher et al. "Improved oral drug delivery: solubility limitations overcome by the use of prodrugs", Arfv. *Drug Delivery Rev.* 19(2): 115-130 (1996); Fleisher et al. "Design of prodrug for improved gastrointestinal absorption by intestinal enzyme targeting", *Methods Enzymol.* 112 (Drug Enzyme Targeting, Pt. A): 360-81, (1985); Farquhar D, et al., "Biologically Reversible Phosphate-Protective Groups", *Pharm. Sci.*, 72(3): 324-325 (1983); Freeman S, et al., "Bioreversible Protection for the Phospho Group: Chemical Stability and Bioactivation of Di(4-acetoxy-benzyl)Methylphosphonate with Carboxyesterase," *Chem. Soc., Chem. Commun.*, 875-877 (1991); Friis and Bundgaard, "Prodrugs of phosphates and phosphonates: Novel lipophilic alphaacyloxyalkyl ester derivatives of phosphate- or phosphonate containing drugs masking the negative charges of these groups", *Eur. J. Pharm. Sci.* 4: 49-59 (1996); Gangwar et al., "Pro-drug, molecular structure and percutaneous delivery", *Des. Biopharm. Prop. Prodrugs Analogs*, [Symp.] Meeting Date 1976, 409-21. (1977); Nathwani and Wood, "Penicillins: a current review of their clinical pharmacology and therapeutic use", *Drugs* 45(6): 866-94 (1993); Sinhababu and Thakker, "Prodrugs of anticancer agents", *Adv. Drug Delivery Rev.* 19(2): 241-273 (1996); Stella et al., "Prodrugs. Do they have advantages in clinical practice?", *Drugs* 29(5): 455-73 (1985); Tan et al. "Development and optimization of anti-HIV nucleoside analogs and prodrugs: A review of their cellular pharmacology, structure-activity relationships and pharmacokinetics", *Adv. Drug Delivery Rev.* 39(1-3): 117-151 (1999); Taylor, "Improved passive oral drug delivery via prodrugs", *Adv. Drug Delivery Rev.*, 19(2): 131-148 (1996); Valentino and Borchardt, "Prodrugs strategies to enhance the intestinal absorption of peptides", *Drug Discovery Today* 2(4): 148-155 (1997); Wiebe and Knaus, "Concepts for the design of anti-HIV nucleoside prodrug for treating cephalic HIV infection", *Adv. Drug Delivery Rev.*: 39(1-3):63-80 (1999); Waller et al., "Prodrugs", *Br. J. Clin. Pharmac.* 28: 497-507 (1989), content of all of which is herein incorporated by reference in its entirety.

The methods described herein can further comprise administering a second agent and/or treatment to the subject, e.g. as part of a combinatorial therapy. Non-limiting examples of a second agent and/or treatment can include one or more of laser surgery, pulsed dye laser, corticosteroid therapy, oral corticosteroid therapy, beta-blockers, topical beta-blockers, vincristine, interferon, surgical removal, and pharmaceutically acceptable salts, acids or derivatives of any of the preceding compounds.

In certain embodiments, an effective dose of a composition comprising a HemSC inhibitor, and optionally, a steroid and/or beta-blocker as described herein can be administered to a patient once. In certain embodiments, an effective dose of a composition comprising a HemSC inhibitor, and optionally, a steroid and/or beta-blocker can be administered to a patient repeatedly. For systemic administration, subjects can be administered a therapeutic amount of a composition comprising a HemSC inhibitor and, optionally, a steroid and/or beta-blocker, such as, e.g. 0.1 mg/kg, 0.5 mg/kg, 1.0 mg/kg, 2.0 mg/kg, 2.5 mg/kg, 5 mg/kg, 10 mg/kg, 15 mg/kg, 20 mg/kg, 25 mg/kg, 30 mg/kg, 40 mg/kg, 50 mg/kg, or more. A composition comprising a HemSC inhibitor, and, optionally, a steroid and/or beta-blocker can be administered over a period of time, such as over a 5 minute, 10 minute, 15 minute, 20 minute, or 25 minute period or longer. The administration can be repeated, for example, on a regular basis, such as hourly, every 3 hours, 6 hours, 12 hours or longer or such as biweekly (i.e., every two weeks) for one month, two months, three months, four months or longer.

In some embodiments, after an initial treatment regimen, the HemSC inhibitor can be administered on a less frequent basis. As a non-limiting example, after treatment biweekly for three months, treatment can be repeated once per month, for six months or a year or longer. Treatment according to the methods described herein can reduce levels of a marker or symptom of a condition, e.g. proliferative vascular disorder by at least 10%, at least 15%, at least 20%, at least 25%, at least 30%, at least 40%, at least 50%, at least 60%, at least 70%, at least 80% or at least 90% or more. Markers and symptoms of proliferative vascular disorders, e.g. hemangioma can include, but are not limited to tumors of the endothelial cells of blood vessels; an increased number of blood vessels and/or capillaries; discoloration of the skin; GLUT-1 expression; hemosiderin pigmentation; ulceration; and bleeding.

In some embodiments, a composition comprising a HemSC inhibitor and a steroid and/or a beta-blocker can be administered to the subject in the same pharmaceutical composition or in different pharmaceutical compositions (at the same time or at different times). When administered at different times, a composition comprising a HemSC inhibitor and a composition comprising a steroid and/or a beta-blocker can be administered substantially simultaneously with each other or within 5 minutes, or 10 minutes, or 20 minutes, or 60 minutes, or 2 hours, or 3 hours, or 4 hours, or 8 hours, or 12 hours, or 24 hours of administration of the other. When a HemSC inhibitor and a steroid and/or a beta-blocker are administered in different pharmaceutical compositions, routes of administration can be the same or different. For example, a composition comprising a HemSC inhibitor can be administered by any appropriate route known in the art including, but not limited to orally or systemically, and the steroid and/or beta-blocker can be administered by a different route, e.g. topically, or a route commonly used in the art for administration of the steroid and/or beta-blocker.

In some embodiments, administration of a composition comprising a HemSC inhibitor can precede, can be concurrently or concomitantly (e.g. at the same time) with and/or follow the administration of a steroid and/or beta-blocker by intervals ranging from minutes to weeks. In embodiments where a composition comprising a HemSC inhibitor and composition comprising a steroid and/or beta-blocker are applied administered to a subject, one would generally ensure that a significant period of time did not expire between the time of each delivery, such that the composition comprising a HemSC inhibitor and a steroid and/or beta-blocker would still be able to exert an advantageously combined effect on subject and/or the tissue of the subject affected by a proliferative vascular disorder.

The dosage of a composition as described herein can be determined by a physician and adjusted, as necessary, to suit observed effects of the treatment. With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment, or make other alterations to the treatment regimen. The dosing schedule can vary from once a week to daily depending on a number of clinical factors, such as the subject's sensitivity to a HemSC inhibitor, and optionally, a steroid and/or beta-blocker. The desired dose or amount of activation can be administered at one time or divided into subdoses, e.g., 2-4 subdoses and administered over a period of time, e.g., at appropriate intervals through the day or other appropriate schedule. In some embodiments, administration can be chronic, e.g., one or more doses and/or treatments daily over a period of weeks or months. Examples of dosing and/or treatment schedules are administration daily, twice daily, three times daily or four or more times daily over a period of 1 week, 2 weeks, 3 weeks, 4 weeks, 1 month, 2 months, 3 months, 4 months, 5 months, or 6 months, or more.

The dosage ranges for the administration of a HemSC inhibitor, and optionally, a steroid and/or beta-blocker, according to the methods described herein depend upon, for example, the form of the compound(s), its potency, and the extent to which symptoms, markers, or indicators of a condition described herein are desired to be reduced, for example the percentage reduction desired for vasculogenesis and/or tumor size. The dosage should not be so large as to cause adverse side effects, such as thrombocytopenia. Generally, the dosage will vary with the age, condition, and sex of the patient and can be determined by one of skill in the art. The dosage can also be adjusted by the individual physician in the event of any complication.

The efficacy of a HemSC inhibitor, and optionally, a steroid and/or beta-blocker in, e.g. the treatment of a condition described herein, or to induce a response as described herein (e.g. reduction of tumor size, extent, or rate of growth) can be determined by the skilled clinician. However, a treatment is considered "effective treatment," as the term is used herein, if any one or all of the signs or symptoms of a condition described herein are altered in a beneficial manner, other clinically accepted symptoms are improved, or even ameliorated, or a desired response is induced e.g., by at least 10% following treatment according to the methods described herein. Efficacy can be assessed, for example, by measuring a marker, indicator, symptom, and/or the incidence of a condition treated according to the methods described herein or any other measurable parameter appropriate, e.g. extent of vasculogenesis and/or tumor size. Efficacy can also be measured by a failure of an individual to worsen as assessed by hospitalization, or need for medical interventions (i.e., progression of the disease is halted). Methods of measuring these indicators are known to those of skill in the art and/or are described herein. Treatment includes any treatment of a disease in an individual or an animal (some non-limiting examples include a human or an animal) and includes: (1) inhibiting the disease, e.g., preventing a worsening of symptoms (e.g. pain or inflammation); or (2) relieving the disease, e.g., causing regression of symptoms. An effective amount for the treatment of a disease means that amount which, when administered to a subject in need thereof, is sufficient to result in effective treatment as that term is defined herein, for that disease. Efficacy of an agent can be determined by assessing physical indicators of a condition or desired response, (e.g. decrease in tumor size). It is well within the ability of one skilled in the art to monitor efficacy of administration and/or treatment by measuring any one of such parameters, or any combination of parameters. When using an experimental animal model, efficacy of treatment is evidenced when a statistically significant change in a marker is observed, e.g. extent of vascularization and/or tumor size.

In vitro and animal model assays are provided herein which allow the assessment of a given dose of a HemSC inhibitor, and optionally, a steroid and/or beta-blocker. By way of non-limiting example, the effects of a dose of a HemSC inhibitor, and optionally, a steroid and/or beta-blocker can be assessed by the degree to which HemSC proliferation is inhibited by the compound in an in vitro clonogenic assay as described here in the Examples. A non-limiting example of a protocol for such an assay is as follows: HemSCs can be incubated with the HemSC inhibitor, and, optionally a steroid and/or beta-blocker for 4 days. Following washout of the drug, cells can be serially diluted to 8 cells per ml and plated in 384 well plates, 40 µl/well. Medium can be replaced every 48 hours. At day 9, cells can be fixed and stained with Hoechst. Following image capture by automated fluorescence microscopy, colony formation and the number of cells/colony can be determined by quantifying the number of wells with Hoechst-stained nuclei and the number of Hoechst-stained nuclei/well using MetaXpress Software.

The efficacy of a given dosage combination can also be assessed in an animal model, e.g. the murine two cell model of IH described previously (Greenberger et al., 2010). HemSCs and cbEPCs can be mixed with Matrigel and injected subcutaneously into mice, e.g. nude mice. Blood flow can be measured in the Matrigel implants using contrast-enhanced micro-ultrasonic imaging. Baseline blood flow can be measured 7 days after implantation, and mice can then receive treatment with a HemSC inhibitor, e.g. rapamycin at 2 mg/kg by i.p. injection, and, optionally, a steroid and/or beta-blocker. Ten days after treatment, blood flow can be measured. A stable level of blood flow, or preferably, a reduction in blood flow indicates an effective dose. Vascularization can also be determined macroscopically and by histological analysis.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The technology described herein is further illustrated by the following examples which in no way should be construed as being further limiting.

Some embodiments of the technology described herein can be defined according to any of the following numbered paragraphs:

1. A method of treating a proliferative vascular disorder, the method comprising:
   administering a HemSC inhibitor; and, optionally,
   administering a steroid and/or a beta-blocker.
2. The method of paragraph 1, wherein the HemSC inhibitor is selected from the group consisting of:
   an mTOR inhibitor and nifedipine.
3. The method of paragraph 2, wherein the mTOR inhibitor is selected from the group consisting of:
   everolimus; temisrolimus; and rapamycin.
4. The method of any of paragraphs 1-3, wherein the steroid is a corticosteroid.
5. The method of paragraph 4, wherein the corticosteroid is selected from the group consisting of:
   dexamethasone; prednisone; prednisolone; triamcinolone; clobetasol propionate;
   betamethasone valerate; betamethasone dipropionate; and mometasone furoate.
6. The method of any of paragraphs 1-5, wherein the beta-blocker is selected from the group consisting of:
   atenolol; nadolol; propranolol and timolol.
7. The method of any of paragraphs 1-6, wherein the i) HemSC inhibitor and ii) the steroid and/or beta-blocker are administered concomitantly.
8. The method of any of paragraphs 1-7, wherein the proliferative vascular disorder is a vascular malformation.
9. The method of any of paragraphs 1-8, wherein the proliferative vascular disorder is a vascular tumor.
10. The method of any of paragraphs 1-9, wherein the proliferative vascular disorder is selected from the group consisting of:
    hemangioma; verrucous hemangioma; nevoid hemangioma; senile hemangioma;
    kaposiform hemangioendothelioma; pyogenic granuloma and congenital hemangioma.
11. The method of paragraph 10, wherein the proliferative vascular disorder is infantile hemangioma.
12. The method of any of paragraphs 1-11, wherein one or more of the compounds are administered systemically.
13. The method of any of paragraphs 1-12, wherein one or more of the compounds are administered orally.
14. The method of any of paragraph 1-11, wherein one or more of the compounds are administered intralesionally.
15. The method of any of paragraphs 1-11, wherein one or more of the compounds are administered topically.
16. A pharmaceutical composition comprising i) a HemSC inhibitor and ii) a steroid and/or beta-blocker.
17. The composition of paragraph 16, further comprising a pharmaceutically acceptable carrier.
18. The composition of any of paragraphs 16-17, wherein the HemSC inhibitor is selected from the group consisting of:
    an mTOR inhibitor and nifedipine.
19. The composition of paragraph 18, wherein the mTOR inhibitor is selected from the group consisting of:
    everolimus; temisrolimus; and rapamycin.
20. The composition of any of paragraphs 16-19, wherein the steroid is a corticosteroid.
21. The composition of paragraph 20, wherein the corticosteroid is selected from the group consisting of:
    dexamethasone; prednisone; prednisolone; triamcinolone; clobetasol propionate;
    betamethasone valerate; betamethasone dipropionate; and mometasone furoate.
22. The composition of any of paragraphs 16-21, wherein the beta-blocker is selected from the group consisting of:
    atenolol; nadolol; propranolol and timolol.

Examples

Infantile hemangioma (IH) is a common childhood vascular tumor. Although benign, some hemangiomas cause deformation and destruction of features or endanger life. The current treatments, corticosteroid or propranolol, are administered for several months and can have adverse effects for the infant. Described herein is a high-throughput screen to identify FDA-approved drugs that could be used to treat this tumor. Rapamycin, an mTOR inhibitor, was identified based on its ability to inhibit proliferation of a hemangioma-derived stem cell population, human vasculogenic cells previously discovered by the inventors. In vitro and in vivo studies show that Rapamycin reduces the self-renewal capacity of the hemangioma stem cells, diminishes differentiation potential, and inhibits the vasculogenic activity of these cells in vivo. Longitudinal in vivo imaging of blood flow through vessels formed with hemangioma stem cells shows that Rapamycin also leads to regression of hemangioma blood vessels, consistent with its known anti-angiogenic activity. Finally, it is demonstrated herein that Rapamycin-induced loss of stemness can work in concert with corticosteroid, the current standard therapy for problematic hemangioma, to block hemangioma formation in vivo. The experiments described herein reveal that Rapamycin targets the self-renewal and vascular differentiation potential in patient-derived hemangioma stem cells and supports a therapeutic strategy to prevent formation of this disfiguring and endangering childhood tumor.

Infantile Hemangioma (IH) is a common childhood tumor composed of disorganized blood vessels and immature cells (Mulliken, 1988) (Drolet et al., 1999). IH represents a disruption of neonatal vasculogenesis, the de novo formation of vessels from progenitor cells, and of angiogenesis, the sprouting of new vessels from pre-existing vasculature. It is demonstrated herein that Rapamycin, an inhibitor of the mTOR pathway, diminishes the self-renewal capacity of IHderived stem cells (HemSCs), initiates the differentiation of HemSCs towards a perivascular cell phenotype and inhibits de novo formation of vessels from HemSCs. This anti-vasculogenic activity of Rapamycin, which is distinct from its known anti-angiogenic effects, has not been shown previously, and has implications for the mTOR pathway in human neonatal vasculogenesis as well as permitting new strategies to treat the most endangering IH.

Although a benign and usually harmless tumor, some IH deform or destroy facial features and/or obstruct vision and breathing. 40-80% result in permanent cutaneous residua, which can be disfiguring. Corticosteroids are traditional first-line therapy, however the adverse effects are numerous (Boon et al., 1999) and approximately 16% of hemangiomas do not respond (Bennett et al., 2001). Propranolol has recently been introduced as a safe and effective treatment for IH (Leaute-Labreze et al., 2008) (Siegfried et al., 2008). However, its use is not without risks, and not all tumors respond (Frieden and Drolet, 2009). Thus, there is a need for additional therapies that will shorten treatment duration or, ultimately, prevent problematic hemangiomas from ever forming.

The inventors have previously isolated stem cells (HemSCs) and endothelial cells (HemECs) from specimens of proliferating IH (Boye et al., 2001; Khan et al., 2008). HemSCs have a mesenchymal morphology, robust proliferation, undergo multi-lineage differentiation and form human blood vessels with features of IH when injected subcutaneously into nude mice (Khan et al., 2008). Corticosteroids inhibit this vessel formation by suppressing VEGF-A in HemSCs, while having no effect on HemECs or normal human cord blood-derived endothelial progenitor cells (cbEPCs) (Greenberger et al., 2010). However, corticosteroids have no effect on the proliferation of HemSCs. Therefore, it was hypothesized a drug that inhibits proliferation of HemSCs might prevent the growth of proliferating IH. To pursue this, chemical libraries were screened to identify drugs that preferentially inhibit the proliferation of HemSCs.

Results

A Cell-Based Screen Identifies Compounds that Selectively Inhibit Proliferation of HemSCs.

Figure 7:
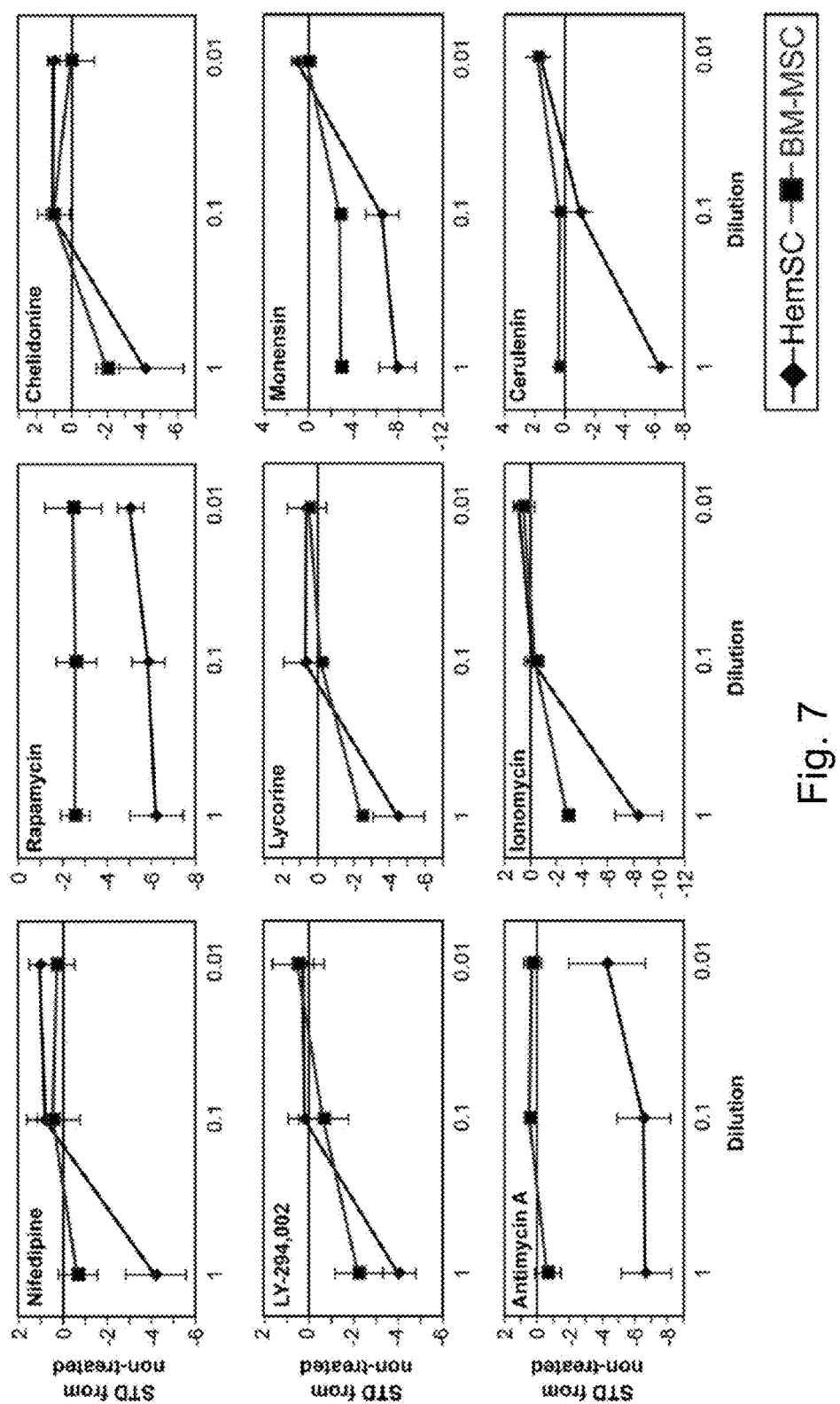
FIG. 7 depicts graphs demonstrating the identification and validation of compounds that selectively inhibit HemSCs. Dose-response curves of control BM-MSC and HemSCs treated with indicated compounds. Bars denote the standard deviation with n=8 for each treatment combination.

A proliferation assay was designed to test in parallel HemSCs and bone marrow-derived stem cells (BM-MSCs). BM-MSCs share several characteristics with HemSCs: expression of mesenchymal markers, spindle-shaped morphology, and the potential to differentiate into bone, fat and cartilage. In contrast to HemSCs, BM-MSCs do not form vessels when injected as a single cell type in Matrigel into nude mice (Khan et al., 2008). The methods and results of the screen are provided (FIG. 7, Table 1).

Figure 1B:
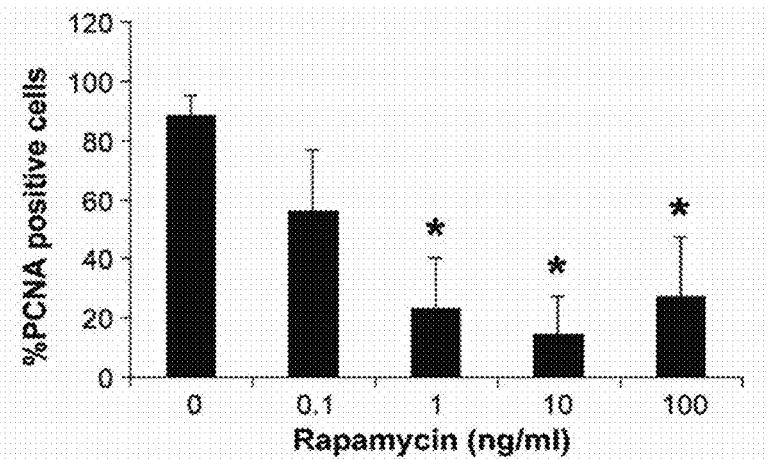
Figure 8:
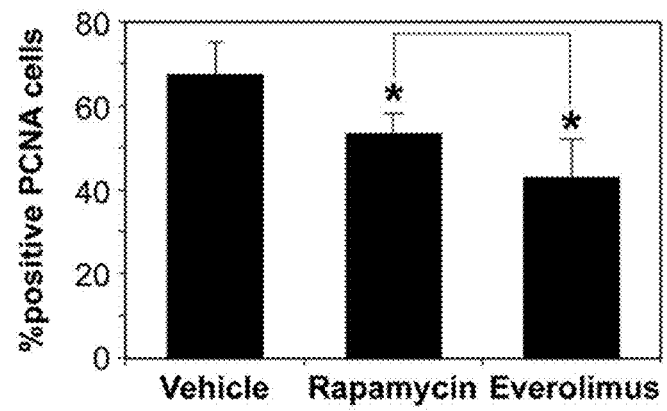
FIG. 8 depicts a graph of the quantification of PCNA-positive cells in Matrigel explants of mice injected with Rapamycin or Everolimus. Bars denote mean value determined from all explants±the SEM. N-6/group. *P<0.05 compared to vehicle injected group. This data accompanies FIG. 2B.

Of the nine compounds identified, rapamycin was selected for further study because its activity was maintained at low concentrations and its favorable safety profile has been established in pediatric clinical trials (Sindhi et al., 2005). Rapamycin led to ~40% inhibition of HemSCs proliferation at concentrations of 1 ng/ml and higher, while BM-MSCs or normal human dermal fibroblasts (NHDF) were less sensitive (FIG. 1A). Proliferating cell nuclear antigen (PCNA) served as an additional measure of proliferation (Prelich et al., 1987) (Hall and Levison, 1990). Rapamycin led to dose-dependent decrease in the percentage of PCNA-positive HemSCs with 80% suppression at 10 ng/ml (FIG. 1B). Viability was not affected by Rapamycin as seen by normal cell morphology visualized by phalloidin staining (FIG. 8; data not shown).

Figure 1C:
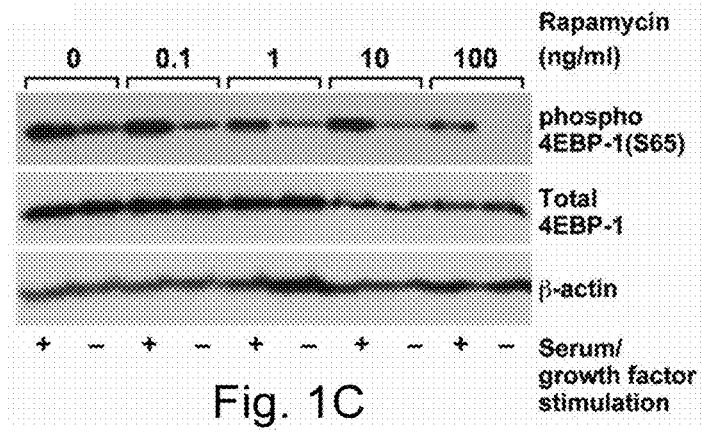
Figure 1D:
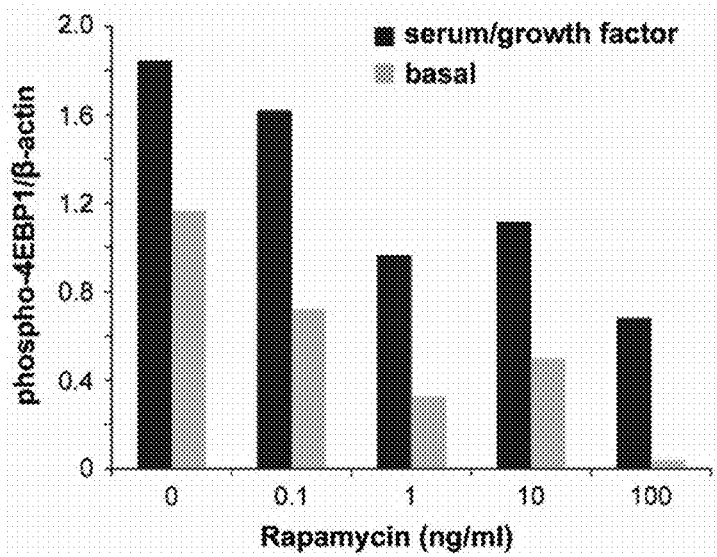

Rapamycin is an inhibitor of mTOR (mammalian target of Rapamycin). To verify that rapamycin inhibited mTOR in the HemSCs, the phosphorylation status of two targets of mTOR signaling—serine/threonine kinase p70 S6 kinase and eIF-4EBP1 (Hara et al., 1997) was examined. Rapamycin caused a dose-dependent decrease in the constitutive and serum/growth factor stimulated levels of phosphorylated 4EBP1 (FIG. 1C, D). To verify that mTOR is a relevant target in IH, we analyzed its upstream regulator AKT. Phosphorylated AKT was detected in proliferating IH tumor specimens. In contrast, very low expression was observed in involuting IH specimens (data not shown).

Rapamycin Suppresses Vasculogenesis in the IH Tumor Model.

Figure 2A:
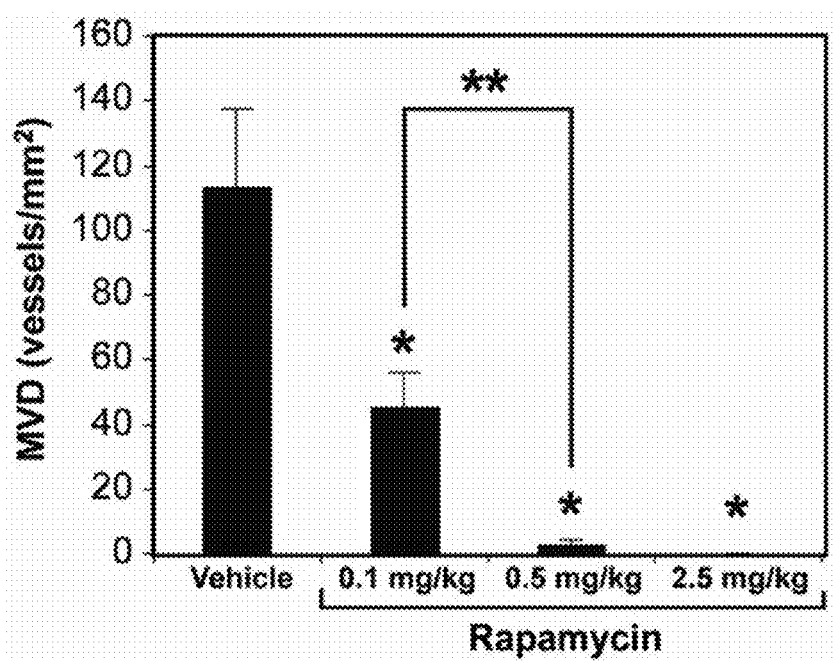
FIGS. 2A-2C demonstrate that rapamycin suppresses vessel formation in an IH tumor model.
Figure 2B:
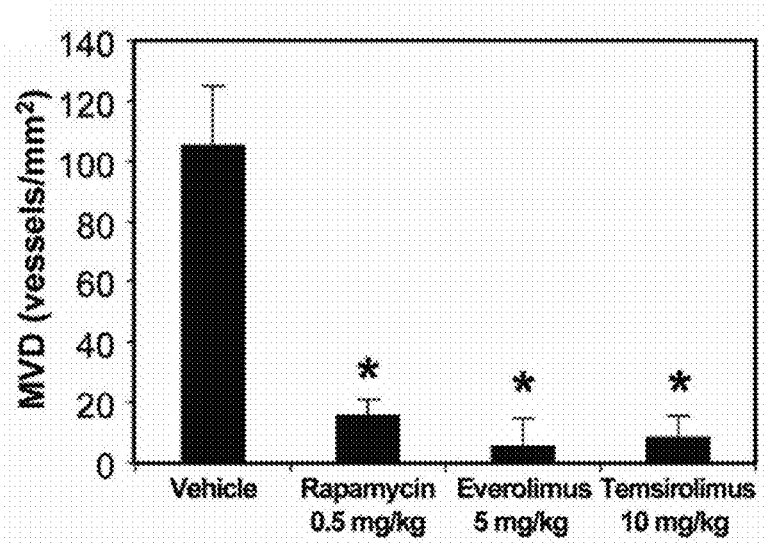
Figure 9:
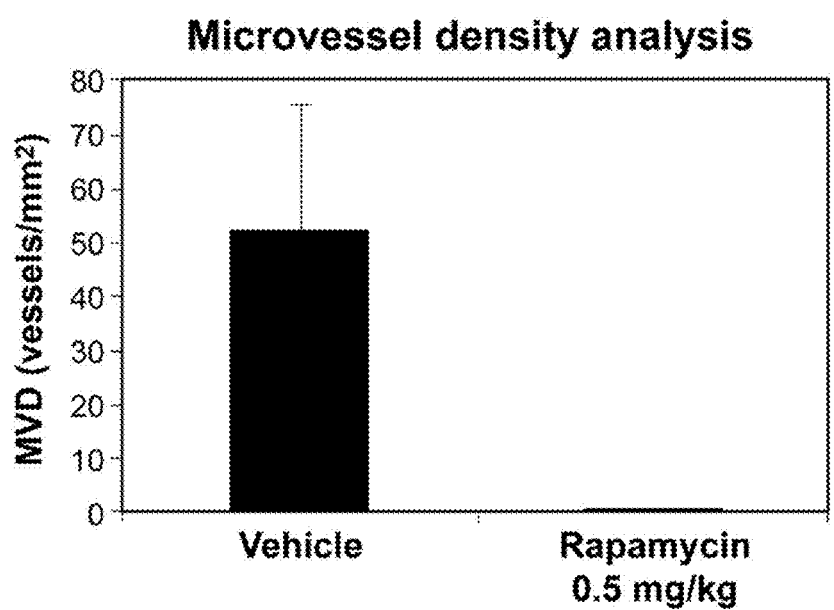
FIG. 9 depicts a graph of the effect of rapamycin on the "one cell" model. HemSCs were suspended in Matrigel and injected s.c. in nude mice (n=5/group). Mice were injected i.p. with vehicle or rapamycin on days 1-6. Matrigel implants were explanted on day 7.

Next, the effect of systemic Rapamycin was tested in a two cell model of IH described previously (Greenberger et al., 2010). HemSCs and cbEPCs were mixed with Matrigel and injected subcutaneously in nude mice. This two-cell model has advantages over injecting HemSC alone: first it is more robust and thus more sensitive for detecting dose-response activity. Second, it allows one to test separately the effect of rapamycin on the HemSC versus cbEPCs, which are primary ECs isolated from cord blood that serve as prototypic young ECs. Rapamycin was administered daily by intra-peritoneal injection. Compared with the vehicle-injected mice, Rapamycin caused dose-dependent inhibition of vascularization of the Matrigel implants (FIG. 2A). Anti-human CD31 staining verified that Rapamycin inhibited the de novo formation of human CD31-positive blood vessels: CD31-positive cells were detected, but without lumen formation (data not shown). Rapamycin also inhibited vessel formation when HemSC were implanted alone (FIG. 9; data not shown). Two other mTOR inhibitors, everolimus (Novartis) and temsirolimus (Wyeth/Pfizer), injected systemically as described for Rapamycin, also significantly inhibited formation of blood vessels (FIG. 2B).

Figure 2C:
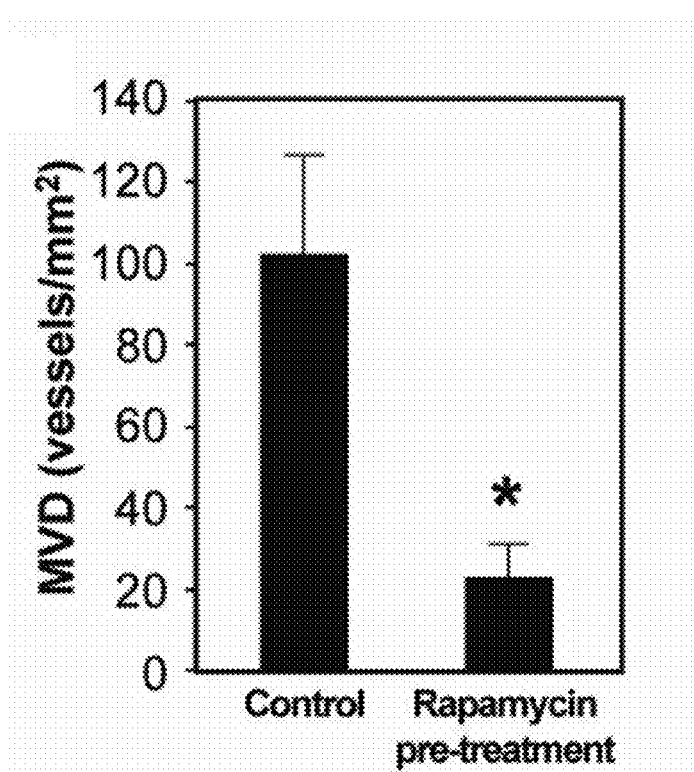

To test whether or not HemSCs are a target of Rapamycin, versus the cbEPCs or a murine host cell, HemSCs were pre-treated with Rapamycin for three days in vitro, the drug was washing out, and the Rapamycin-treated or control HemSCs were resuspended with cbEPCs in Matrigel, and injected into mice. Pre-treatment of HemSCs with Rapamycin led to 80% inhibition of blood vessel formation (FIG. 2C; data not shown). Pre-treatment of cbEPCs had no effect (data not shown). These results demonstrate that HemSCs are directly targeted by Rapamycin.

An Anti-Proliferative Drug is not Sufficient to Inhibit Vasculogenesis In Vivo.

Figure 3A:
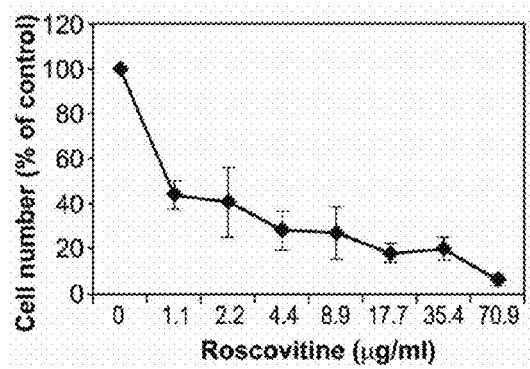
FIGS. 3A-3B demonstrate that the anti-vasculogenic effect of Rapamycin is beyond its anti-proliferative activity.
Figure 3B:
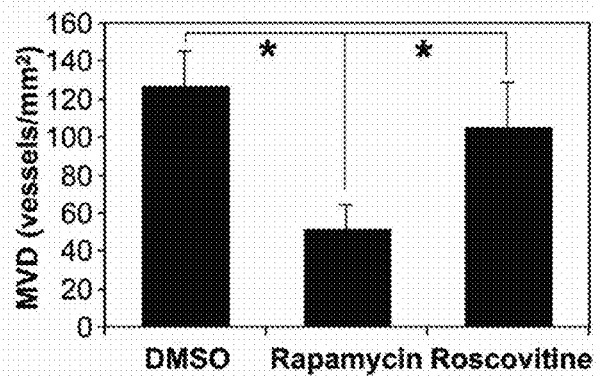
Figure 4A:
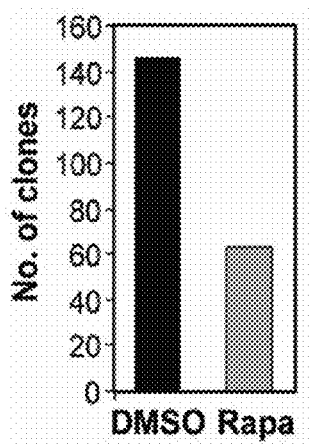
FIGS. 4A-4G demonstrate that rapamycin disrupts the stem-ness of HemSCs.
Figure 4B:
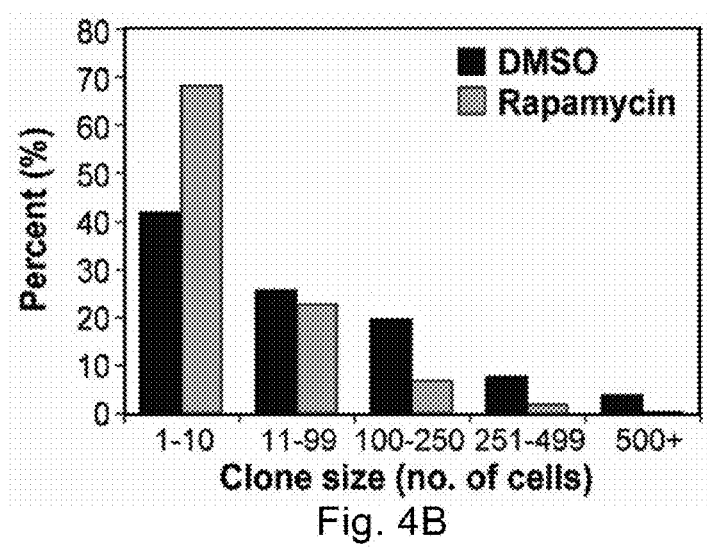

Rapamycin was identified based on its preferential inhibition of HemSCs proliferation. Whether a similar anti-proliferative effect achieved with another drug would be antivasculogenic was tested. To do this, the anti-proliferative drug Roscovitine, a purine analogue andcyclin-dependent kinase inhibitor (De Azevedo et al., 1997) (Meijer et al., 1997) was used. First, the effect of Roscovitine on HemSCs proliferation was titrated in vitro. Roscovitine, at 1.1 µg/ml (3.125 µM) led to 55% inhibition of HemSCs proliferation (FIG. 3A), a similar effect to that of Rapamycin (20 ng/ml) assayed in the same experiment (not shown). Next, HemSCs were pre-treated in vitro for three days with either Roscovitine or Rapamycin, the drugs washed out, and the cells then injected with untreated cbEPC into mice. Rapamycin inhibited microvessel density by 60%. In contrast, Roscovitine did not (FIG. 3B; data not shown), suggesting that pre-treatment of HemSC in vitro with an anti-proliferative drug was not sufficient to reduce the vasculogenic potential HemSC Self-Renewal and Multi-Lineage Differentiation are Disrupted by Rapamycin.

mTOR activity has been shown to be essential for maintaining stem cell self-renewal (Zhou et al., 2009). To test self-renewal capacity of HemSCs, a clonogenic assay was performed (Ingram et al., 2004). Pre-treatment of HemSCs with Rapamycin resulted in a 60% decrease in the number of HemSC colonies formed at 9 days (FIG. 4A). Moreover, stratifying the colonies into groups with increasing cell number demonstrated that Rapamycin pre-treatment abolished the appearance of colonies with >500 cells, reduced the percentage of colonies with 100-250 or 250-500 cells/colony and increased the percentage of colonies with 10 or fewer (FIG. 4 B). These results demonstrate that pre-treatment of cells with Rapamycin for four days resulted in a diminished number of highly proliferative clones.

Figure 4C:
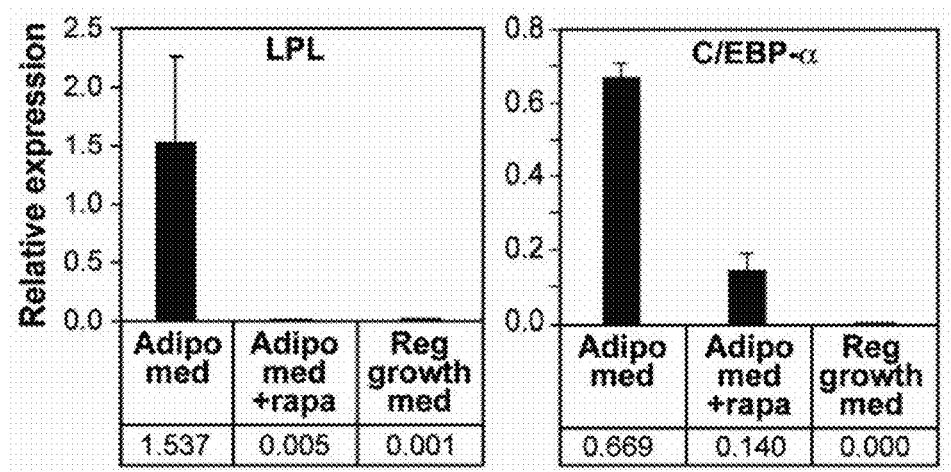

Clonally-derived populations of HemSCs have the ability to differentiate into ECs and adipocytes in vitro and in vivo (Khan et al., 2008). Whether the multi-lineage differentiation of HemSCs could be altered by Rapamycin was assayed. Rapamycin blocked expression of the adipogenic markers lipoprotein lipase (LPL), CCAAT enhancer binding protein α (C/EBP-α) (Darlington et al., 1998) and the accumulation of lipid droplets (Oil Red 0) when HemSC were subjected to an adipogenic differentiation protocol (FIG. 4C; data not shown). No effect was found on the ability of HemSCs to differentiate, under empirically-defined in vitro conditions, towards an endothelial phenotype (data not shown). These observations indicated that Rapamycin inhibits the adipogenic differentiative activity of HemSCs.

Rapamycin Leads to Mesenchymal Maturation and Impaired Vasculogenic Potential.

Figure 4D:
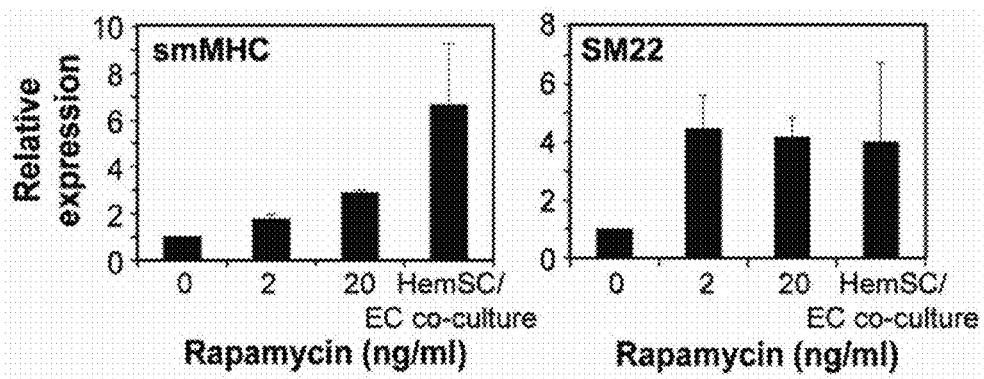
Figure 4E:
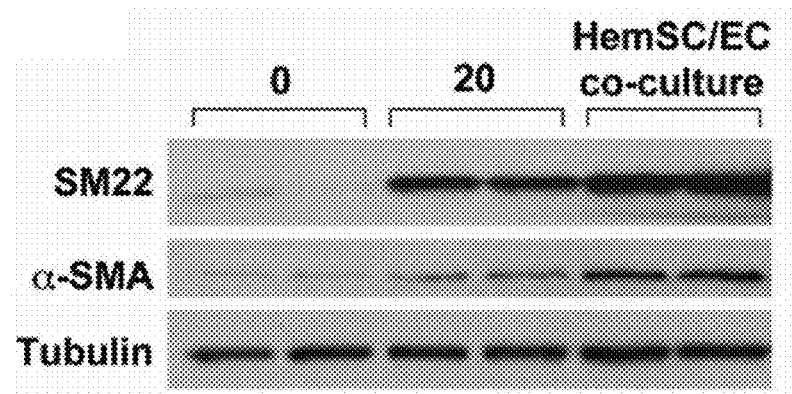
Figure 4F:
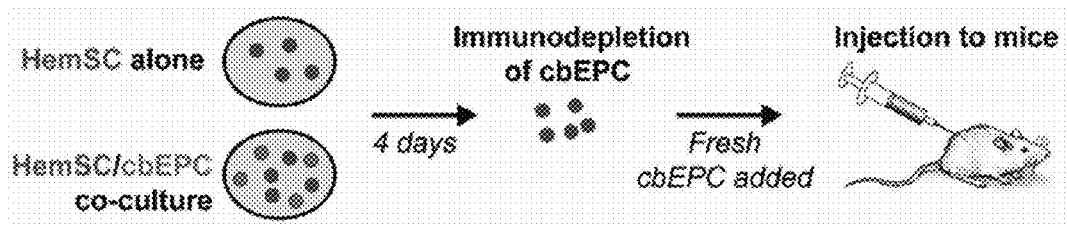
Figure 4G:
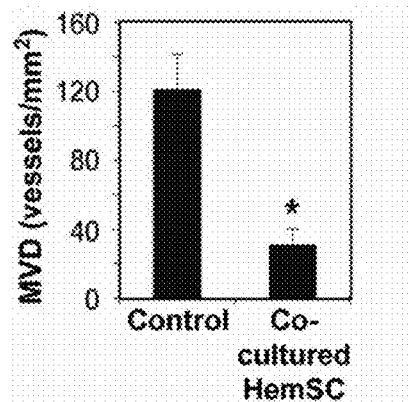
Figure 10A:
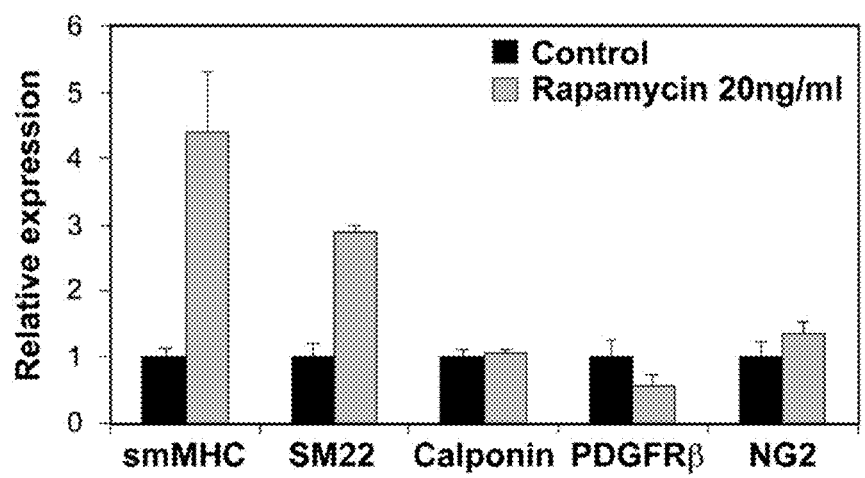
FIGS. 10A-10B depict graphs demonstrating the SMC/pericyte differentiation induced by Rapamycin.
Figure 10B:
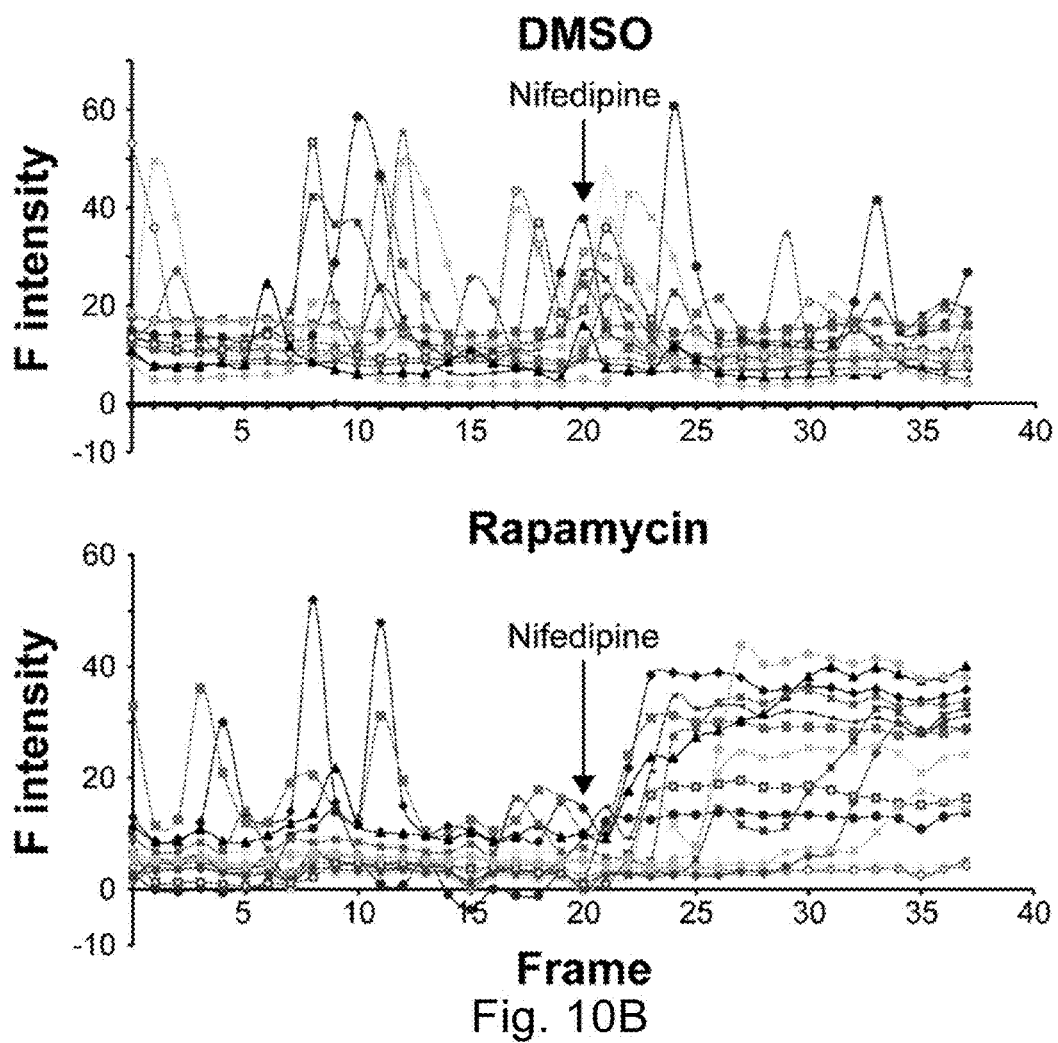

The reduction in self-renewal capacity and inhibition of adipogenesis demonstrated that rapamycin "pushes" the HemSCs to maturate past the state of multipotency. In accord with this hypothesis, HemSCs incubated with Rapamycin have an elongated morphology compared to the control cells (FIG. 8). Therefore, whether or not Rapamycin-treated HemSCs differentiate towards a smooth muscle cell (SMC) or pericytic phenotype was examined. As a positive control, endothelial co-culture was used to stimulate HemSCs towards SMC/pericytic differentiation. Similar to co-cultures of mesenchymal progenitor cells and ECs (Hirschi et al., 1998) (Melero-Martin et al., 2008), when clonal HemSCs are co-cultured with ECs, an upregulation of SMC/pericyte markers in the HemSCs occurs starting on day three (Boscolo et al., 2011). Incubation of HemSCs with Rapamycin for four days led to upregulation of smooth muscle myosin heavy chain (smMHC) and SM22-alpha transcript levels (Li et al., 1996) (FIG. 4D). Similarly, SM22-alpha and α-smooth muscle actin (αSMA) were increased at the protein level (FIG. 4E). Expression levels of calponin, NG2 and PDGF-Rβ were unchanged (FIG. 10A). To test for functional features of SMCs, calcium influx in HemSC treated with Rapamycin or DMSO for six days was analyzed. The results indicate Rapamycin-treated HemSCs express L-type voltage gated channels (FIG. 10B; data not shown). To verify that this mesenchymal maturation has a negative effect on vasculogenic capability, HemSCs were plated alone or in co-culture with cbEPCs for four days. After four days, cbEPCs were separated from the HemSCs using anti-CD31-conjugated magnetic beads. The differentiated HemSCs were combined with fresh cbEPCs, suspended in Matrigel and injected into mice (schematic in FIG. 4F). This prior co-culture step led to a 75% decrease in the microvessel density (FIG. 4G; data not shown). These findings indicate that, independent of the means by which mesenchymal differentiation was induced, either rapamycin pre-treatment or endothelial co-culture, the vasculogenic potential of HemSCs was diminished.

Rapamycin Stimulates Regression of Pre-Existing Vessels Formed from HemSCs.

Figure 5A:
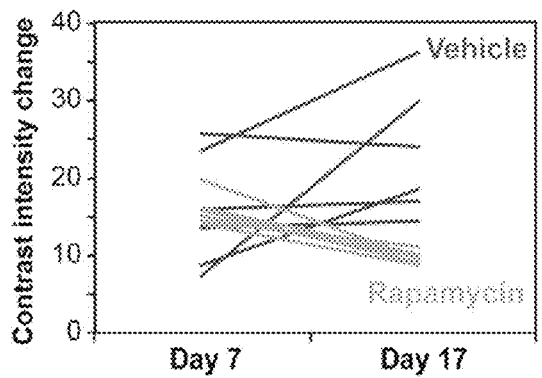
FIGS. 5A-5C demonstrate that Rapamycin stimulates regression of pre-existing vessels in IH tumor model.
Figure 5B:
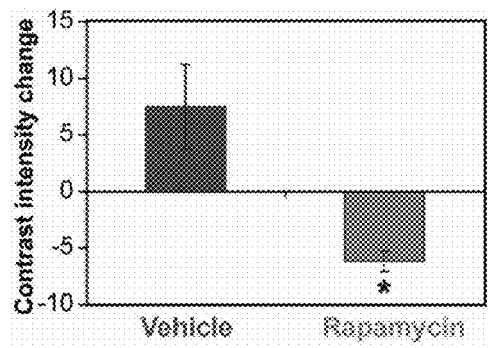
Figure 11A:
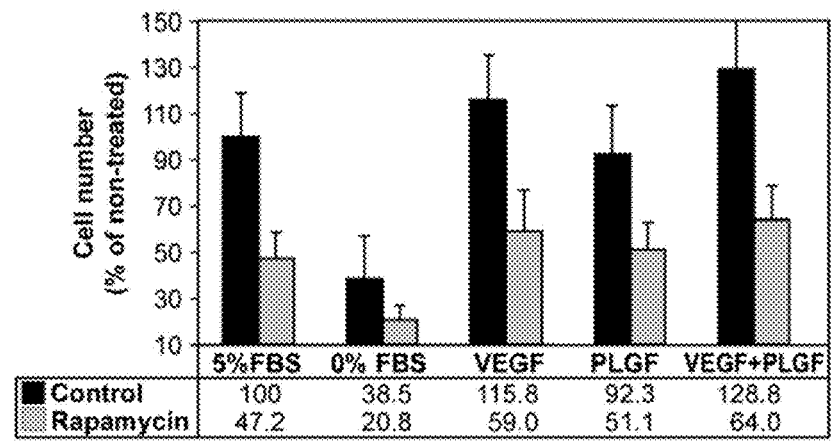
FIGS. 11A-11E depict graphs demonstrating the effect of Rapamycin on proliferation and PLGF-1 expression in endothelial cells.
Figure 11B:
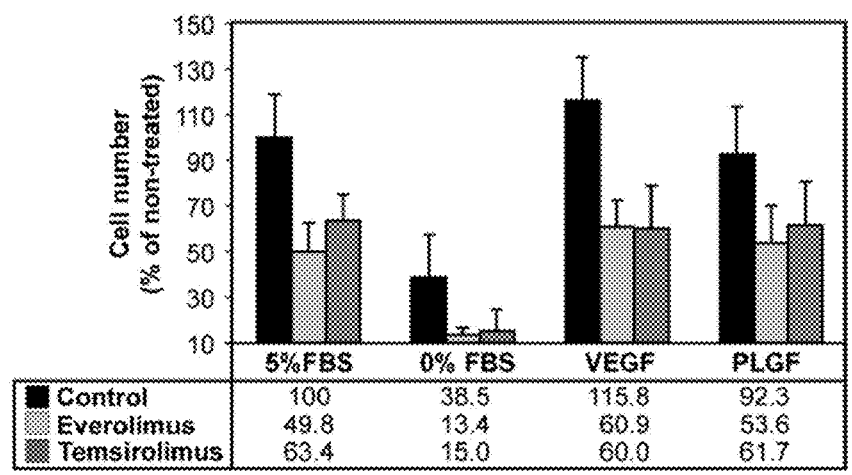
Figure 11C:
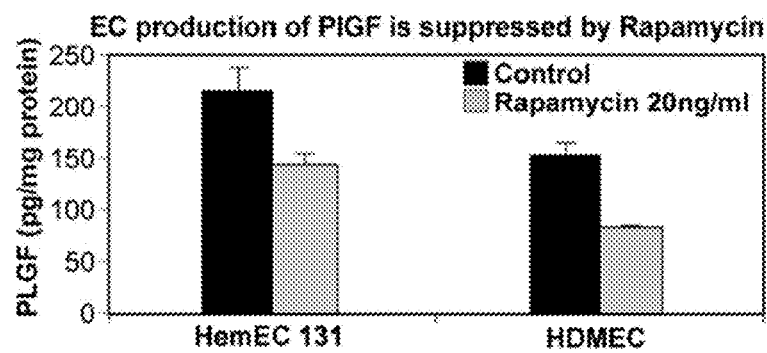
Figure 11D:
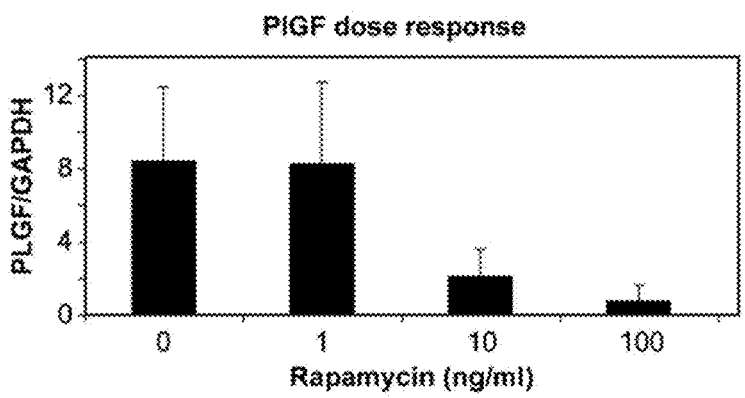
Figure 11E:
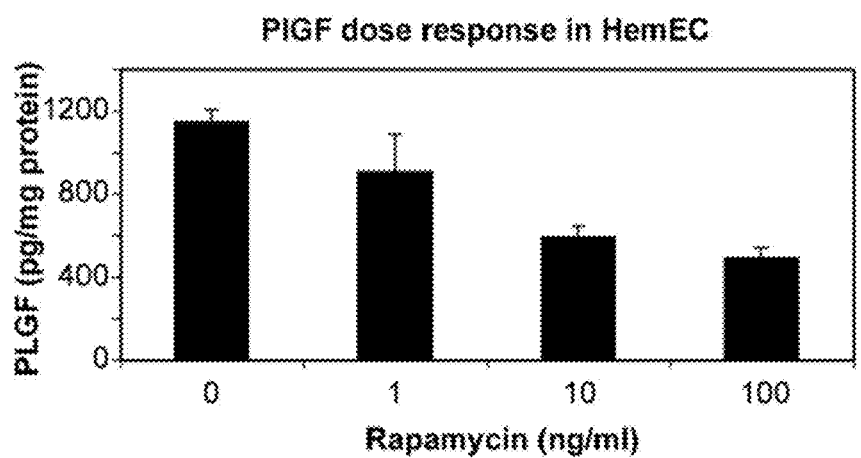
Figure 12:
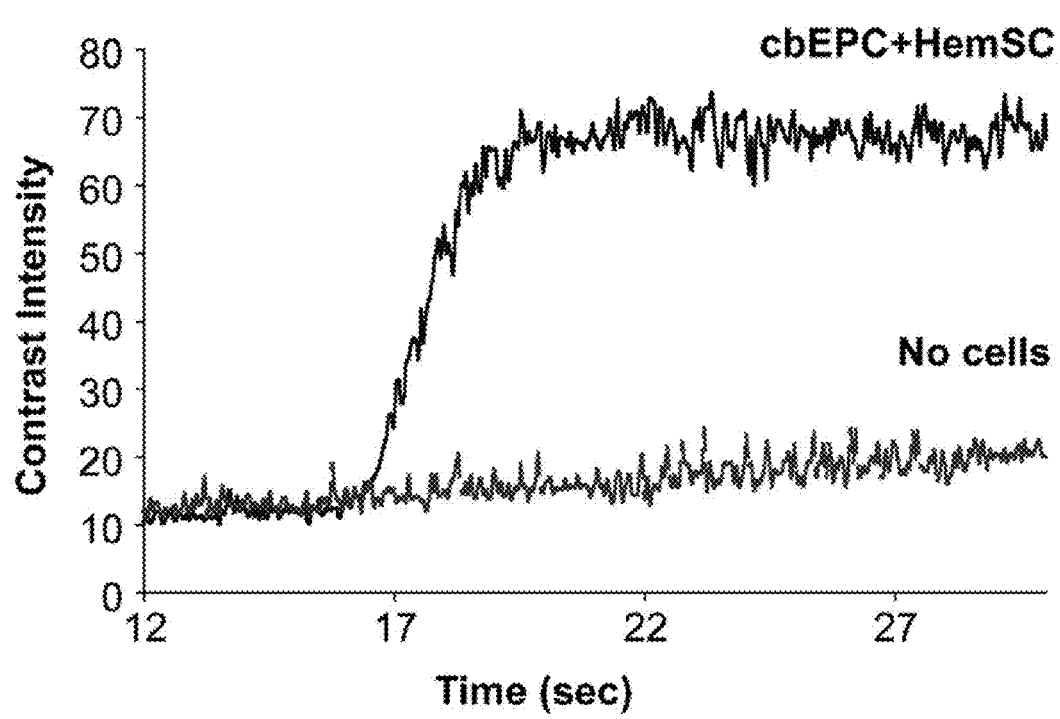
FIG. 12 depicts a graph demonstrating validation of the specificity and sensitivity of contrast-enhanced high resolution ultrasonic (US) imaging for the detection of blood flow in Matrigel implants. Contrast intensity change over time in a control Matrigel implant containing no cells or in an implant containing HemSCs/cbEPCs combination.

Rapamycin is known to have an anti-angiogenic effect on ECs in pathological settings (Guba et al., 2002) (Geerts et al., 2008) (Phung et al., 2007). To study this effect, Rapamycin was tested on cbEPCs. Rapamycin suppressed growth of cbEPCs, which was not rescued by exogenous VEGFA or placental growth factor (PLGF)-1. This observation suggests, as expected, that proliferation and response to VEGF and PLGF-1 mitogenic signals are mTOR-dependent. (FIGS. 11A-11B). In addition, Rapamycin caused a dose-dependent suppression of endogenous PLGF-1 in human ECs, including HemECs. (FIGS. 11C-11D). Thus, it was hypothesized that Rapamycin, able to target both the stem cells and ECs, could cause regression of pre-existing vessels formed from HemSCs and cbEPCs. To test this, contrast-enhanced micro-ultrasonic imaging was used to measure blood flow in the Matrigel implants. First, the sensitivity and specificity of the micro-ultrasonic imaging was verified in the model described herein (FIG. 12). For the experiment, mice were injected with cells and imaged at day 7 to record baseline blood flow in the implants. Mice were then randomized into two groups: Rapamycin, 2 mg/kg by i.p. injection or vehicle alone by i.p. injection. At day 17, follow-up imaging was performed. Mice injected with vehicle had either a stable or increased blood flow in the implant (FIG. 5A, darker lines). Mice injected with Rapamycin had reduced blood flow (FIG. 5A, lighter lines). The average change in contrast intensity change between 7 and 17 days is shown in FIG. 5B. In accord with the imaging results, Matrigel implants of Rapamycin-treated mice were less vascularized macroscopically and by histological analysis (FIG. 5E; data not shown).

Rapamycin and Corticosteroids Target HemSCs by Distinct Mechanisms.

Figure 6A:
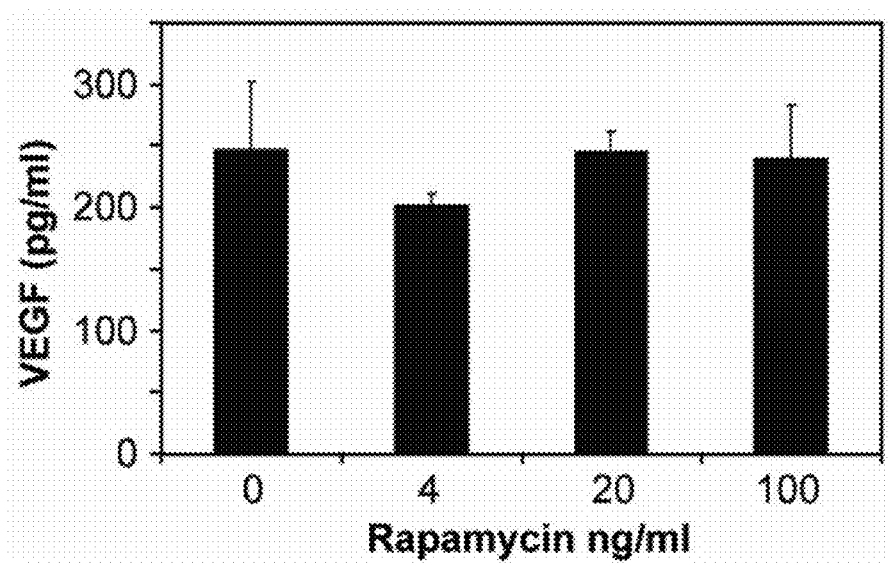
FIGS. 6A-6D demonstrate that rapamycin and corticosteroids target HemSCs by mutually exclusive mechanisms.
Figure 6B:
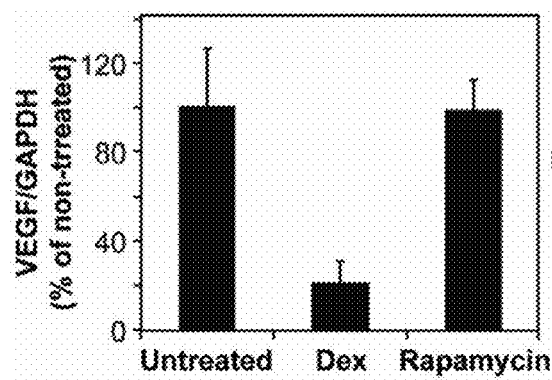
Figure 6C:
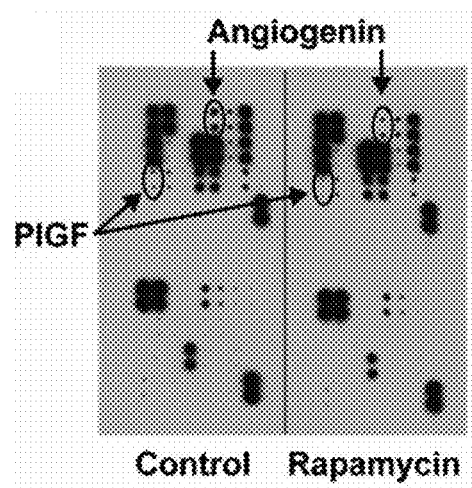
Figure 6D:
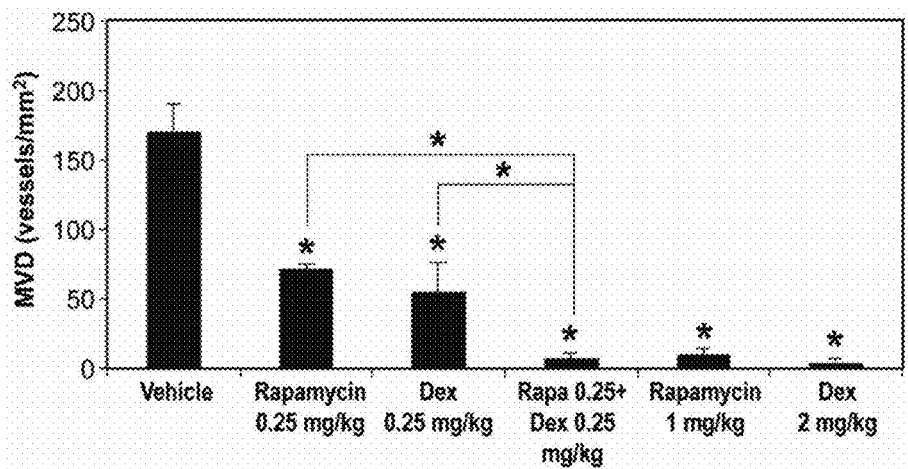
Figure 13A:
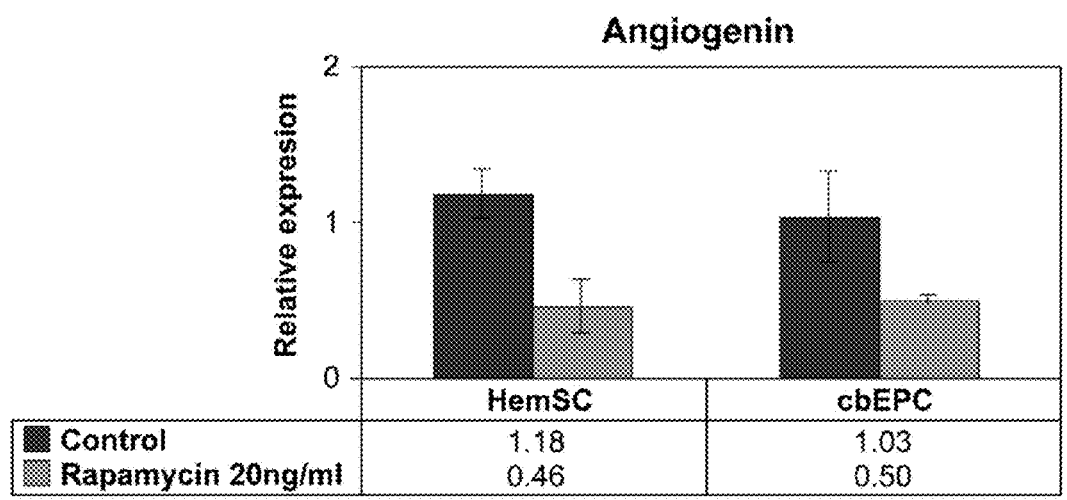
FIGS. 13A-13B depict graphs verifying the angiogenesis antibody arrays positive hits. Quantitative PCR for HemSCs and HemECs expression of Angiogenin (FIG. 13A) and PLGF-1 (FIG. 13B) with (grey bars) or without (black bars) incubation with Rapamycin. Angiogenin and PLGF-1 were identified as positive hits by a protein array (see FIGS. 6A-6D).
Figure 13B:
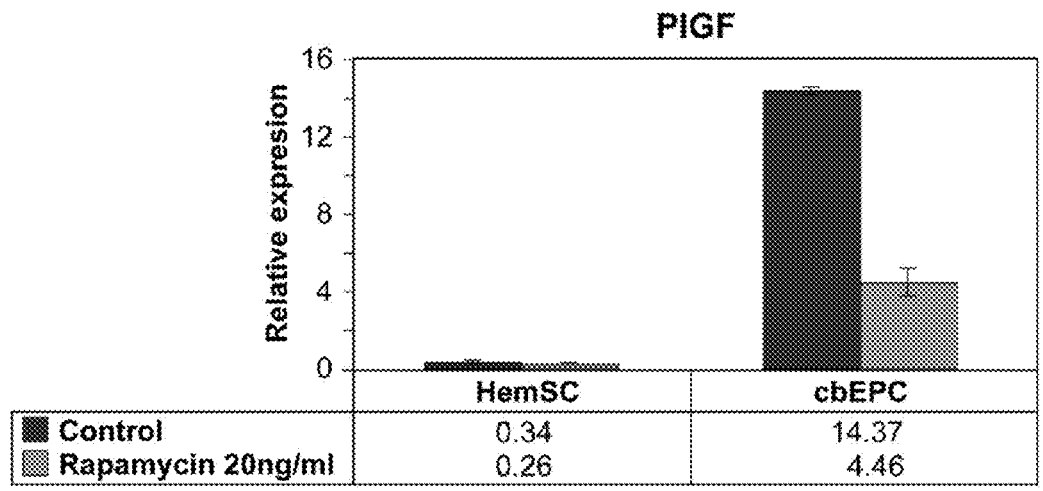

To investigate whether corticosteroids and Rapamycin share common mechanisms for suppressing HemSCs-mediated vascularization, the effect of Rapamycin on expression of a panel of 43 pro-angiogenic proteins was evaluated. In contrast to corticosteroid treatment, Rapamycin did not block the expression of VEGF-A by HemSCs at the mRNA or protein level (FIGS. 6A-6B). Indeed, no overlap was found between the effects of rapamcyin and dexamethasone on expression of the pro-angiogenic cytokines. Dexamethasone suppressed VEGF-A, interleukin-6 (IL-6), matrix metalloproteinase-1 (MMP-1), monocyte chemoattractant protein-1 (MCP-1) and urokinase plasminogen activator receptor (UPAR) (Greenberger et al., 2010). In contrast, Rapamycin downregulated angiogenin and PLGF-1 in HemSCs and cbEPCs (FIG. 6C, verification of the array results in FIGS. 13A-13B).

Because corticosteroid and Rapamycin appeared to have non-overlapping effects on HemSCs and ECs, it was hypothesized that the two drugs could "collaborate" or synergize, i.e., vascularization would be inhibited at low doses of each drug, comparable to either drug used alone at high dose. To test this concept, mice were given i.p. injections of low dose of dexamethasone (0.25 mg/kg), low dose of Rapamycin (0.25 mg/kg) or the combination of both. Combining Rapamycin and dexamethasone enhanced their potency, as evidenced by the inhibition of vasculogenesis that was comparable to high dose of either drug alone (1 and 2 mg/kg of Rapamycin or dexamethasone, respectively, FIG. 6E; data not shown). The efficacy of the two drugs at low doses supports targeting the HemSCs with dexamethasone and HemSCs and HemECs with Rapamycin as an effective therapy for endangering IH.

Discussion

Figure 14:
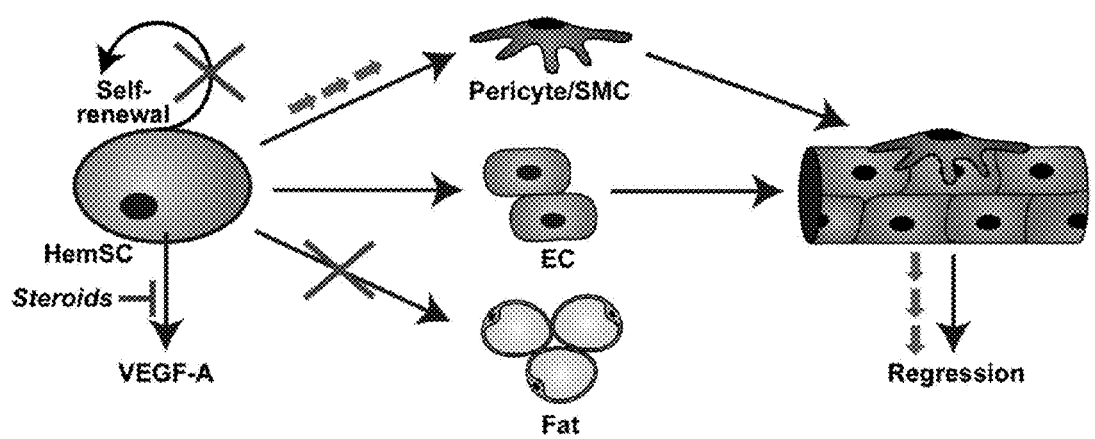
FIG. 14 depicts a schematic of rapamycin effects on HemSCs differentiation and vessel formation. Inhibitory effects of rapamycin are shown with Xs, and stimulatory effects shown by arrows. Corticosteroid inhibition of VEGF-A secretion from HemSCs is shown with blocking symbol.

To identify novel drug candidates for the common childhood tumor IH, chemical libraries were screened for compounds that would inhibit the vasculogenic stem cell, HemSCs, isolated from IH tumor tissue. Rapamycin, an mTOR inhibitor, was identified based on its relative selectivity for HemSCs over BM-MSCs, a normal human stem cell with a similar phenotype. Rapamycin also suppressed self-renewal and modified the differentiative status of the HemSCs. Finally, Rapamycin prevented HemSCs, either alone or combined with cbEPCs, from forming blood vessels in vivo and increased regression of already formed vessels. Without wishing to be limited by theory, the data described herein demonstrate that the primary action of Rapamycin is to cause the HemSCs to lose their stem cell properties; this represents an entirely unique mechanism for blocking human postnatal vasculogenesis. This conclusion is based on the experiments in which pre-treatment of HemSCs for defined periods of time diminished self-renewal in vitro and inhibited vasculogenesis in vivo. Furthermore, inhibiting proliferation per se with Roscovitine was not sufficient to block vasculogenesis. An alternative mechanism to Rapamycin's anti-vasculogenic effect in vivo might be the inhibition of the interaction between HemSC and cbEPCs. Evidence for the mTOR pathway was shown by the activation of the upstream, positive modulator AKT in proliferating IH tumor specimens. Finally, it is demonstrated herein that Rapamycin exerts non-overlapping, inhibitory effects on HemSCs and ECs compared to corticosteroids (FIG. 14).

The role of phosphatase and tensin homologue (PTEN) in controlling the homeostasis and self renewal of stem/progenitor cells in multiple tissues is well established (Hill and Wu, 2009) (Dubrovska et al., 2009; Groszer et al., 2001; Inoue-Narita et al., 2008). However, the contribution of pathways downstream of PTEN, and especially the AKT/mTOR axis, is less defined. Both over-activation and suppression of mTOR activity has been shown to affect self-renewal of stem cells. When human embryonic stem cells (hESCs) are cultivated under self-renewal conditions, mTOR inhibition suffices to disrupt pluripotency and trigger mesoderm and endoderm activities (Zhou et al., 2009). In hematopoeitic stem cells (HSC), over-activation of the mTOR pathway by conditional deletion of PTEN or tuberous sclerosis protein 1, or by constitutive activation of AKT, (Kharas et al., 2010) led to loss of HSC quiescence and reduced long-term HSC function. Rapamycin was shown to rescue HSC function (Yilmaz et al., 2006) (Chen et al., 2008; Zhang et al., 2006). The effects of rapamycin treatment on IH-derived stem cells suggest that tightly-controlled mTOR activity is also essential for postnatal, tissue-resident stem cells.

IH appears in the first weeks of life and with higher incidence in low birth weight preterm infants (Amir et al., 1986). Following the proliferative phase, there is spontaneous regression leading to a fibrofatty residuum. This unique life cycle suggests that this tumor derives from immature progenitor cells, perhaps of neural crest origin (Haggstrom et al., 2006) (Wu et al., 2008), that have not accomplished their full differentiation plan. If that is the case, an intervention that will push these cells to lose their "stemness", perhaps using Rapamycin or another modulator of mTOR activity, is an appealing strategy to prevent growth and/or induce early involution.

Taken together, the data described herein highlight two potential advantages of mTOR inhibitors for the treatment of non-responsive IH. First, the finding that corticosteroids and Rapamycin act by distinct mechanisms to suppress the vasculogenic potential of HemSCs indicates that mTOR inhibitors can be used as "steroid sparing" agents, reducing the required dose of corticosteroid. Moreover, due to the induction of HemSCs differentiation by Rapamycin, the treatment period might be shortened. Rapamycin has adverse effects, but in most cases, these effects are dose or concentration-dependent (Sindhi et al., 2005). Second, in some patients, the permanent fibrofatty residuum after tumor involution can be disfiguring. As described herein, Rapamycin blocks HemSCs adipogenic differentiation, in accordance with previous reports demonstrating a role for intact mTOR activity for adipogenic differentiation (Zhang et al., 2009) Therefore, treating proliferating IH with Rapamycin can prevent this sequela and be advantageous over a natural involution.

Materials and Methods

IH Tissue and Cell Culture.

Specimens of IH were obtained under a protocol approved by the Committee on Clinical Investigation, Children's Hospital Boston; the clinical diagnosis was confirmed in the Department of Pathology. Informed consent was obtained for use of IH specimens, according to the Declaration of Helsinki. The derivation, sources and culture conditions of HemSCs and other cells used in this study have been reported (Khan et al., 2008; Khan et al., 2006; Melero-Martin et al., 2007). For co-culture experiments, HemSCs and cbEPCs ($10^4$ cells per $cm^2$) were plated on fibronectin-(1 µg/$cm^2$) coated dishes at a 1:1 ratio. At the indicated day, cells were trypsinized to prepare a single cell suspension. Removal of cbEPCs was performed by Dynabeads® CD31 Endothelial Cells (Invitrogen) according to the manufacturer's instructions. Differentiation assays towards endothelial cells and adipocytes were done as reported (Khan et al., 2008).

Animal Experiments.

Nude/Nude mice were purchased from Massachusetts General Hospital animal facility. Procedures were approved by the Animal Care and Use Committees of the Children's Hospital, Boston. Anesthesia was induced with 4% isofluorane and maintenance in 1-3% oxygen. Mice were anesthetized once for up to 5 min. The one cell and two cell models of IH were performed as reported (Greenberger et al., 2010; Khan et al., 2008) and microvessel density (MVD) was assessed by counting red blood cell-filled lumens (Melero-Martin et al., 2007). Values reported for each experimental condition correspond to the average MVD value±standard error of the mean (SEM) obtained from all the individual animals.

Systemic mTOR Inhibitors.

Rapamycin, Everolimus and Temsirolimus were purchased from LC Laboratories. Drugs were dissolved in DMSO followed by solvent solution (5% polyethylene glycol, 0.2% carboxymethylcellulose and 0.25% Tween-80 in $H_2O$). Aliquots were kept in −20° C. Mice were given daily intra-peritoneal (i.p.) injections containing 200 µl of drug or the vehicle alone.

High-Resolution Contrast-Enhanced Ultrasonic Imaging.

Figure 5C:
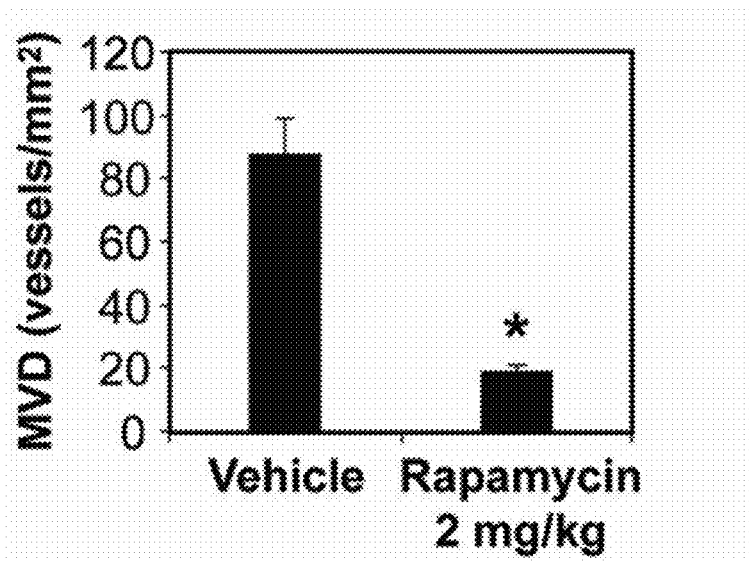

Contrast-enhanced high resolution ultrasonic (US) imaging of the blood flow in Matrigel implants was performed using a Vevo 770 System with a 40-MHz RMV scanhead (Visual Sonics) (Loveless et al., 2009; Olive et al., 2009). MicroMarker non-targeting contrast agent (Visualsonics)

was prepared according to manufacturer's guidelines. For imaging, mice were anesthetized with 2% isofluorane, coupling gel was applied to cover the entire region of interest, and 2-D B-mode scout images established the central slice of the Matrigel. The transducer was placed such that the 6 mm focal spot converged at the center of the Matrigel. Baseline images were acquired in Contrast Mode, and a 50 µL bolus of contrast agent suspension was administered via tail vein catheter during acquisition of a second contrast video. The baseline image was subtracted from the contrast image, and the difference was displayed with a contrast setting of 90 and a threshold setting of 0. For these experiments (FIG. 5), mice were subjected to isofluorane-mediated anesthesia two times (days 7 and 15) for approximately 15 minutes.

Clonogenic Assay.

HemSCs were incubated with Rapamycin 20 ng/ml or DMSO, as a control, for 4 days. Following washout of the drug, cells were serially diluted to 8 cells per ml and plated in 384 well plates, 40 µl/well. Medium was replaced every 48 hours. At day 9, cells were fixed and stained with Hoechst. Following image capture by automated fluorescence microscopy, colony formation and the number of cells/colony were determined by quantifying the number of wells with Hoechst-stained nuclei and the number of Hoechst-stained nuclei/well using MetaXpress Software.

Statistical Analysis.

Data was analyzed by Student's two-tailed t test. One-way-ANOVA was used to test for differences among multiple groups. Differences were considered significant at P<0.05.

Chemical Library Screen and Validation.

High-throughput screening was conducted at the Institute for Chemistry and Cell Biology-Longwood (ICCB-L) screening facility at Harvard Medical School. 1000 cells per well of HemSCs or BM-MSC were seeded into 384-well Clear Bottom Black Polystyrene Microplates (Corning Incorporated, Corning, N.Y.) using an automated plate filler (Wellmate, Thermo Scientific). At 24 hr, 20 mL of compound solutions were pin transferred from stock 384-well plates into the 384-well assay plates containing cells, in triplicates, resulting in ~4 µM final concentration for most compounds. 72 hours later, cells were incubated with paraformaldehyde, stained with Hoechst dye and imaged with Image Xpress Micro (Molecular Devices). Image analysis for cell number was done by MetaXpress software (Molecular Devices). Non-treated cells were used as normalization control and serum starved cells as a negative control. A positive hit was defined as a compound that reduced HemSCs cell number by at least three standard deviations from the non-treated cells and at the same time had little to no effect on proliferation of BM-MSCs. Endothelial cells (EC) were not included in the screen because they would not help to exclude "hits;" drugs that inhibited both HemSC and EC would be of interest because both vasculogenesis (HemSC) and angiogenesis (EC) contribute to growth of IH. The following compound libraries were screened and analyzed: NINDS Custom Collection 2 Collection (1120 compounds). Compounds for the secondary screen (cherry picks) were provided by the ICCB-L. Validation of positive hits was performed in a second screen, under conditions identical to the initial screen, at concentrations of 1.0, 0.1 and 0.01 µM for most compounds in replicates of 8.

Primary Human Cells.

HemSCs were isolated from IH tumor specimens using anti-CD133-conjugated magnetic beads and cultured on fibronectin (FN; 1 µg/cm$^2$) coated plates with Endothelial Basal Medium (EBM2; CC-3156; Cambrex Bio Science, Walkersville, Md.) supplemented with 20% FBS, Single-Quots (CC-4176; Cambrex Bio Science) and PSF. Analysis of HemSC by flow cytometry indicates the cells share many markers, such as CD90, in common with bone-marrow mesenchymal stem cells (BM-MSCs) but do not express endothelial or hematopoietic markers (Khan et al., 2008). cbEPCs were isolated from discarded umbilical cord blood from routine deliveries by selection using anti-CD31-coated magnetic beads. cbEPCs are primary endothelial cells that serve as a prototypic young endothelial cell: they grow robustly in vitro and maintain a stable endothelial phenotype for up to at least 15 trypsin passages (Melero-Martin et al., 2007). They are also referred to as endothelial colony forming cells (ECFCs) in the literature (Ingram et al., 2005; Yoder et al., 2007). cbEPCs are grown in the same medium as HemSCs. BM-MSCs were isolated from commercially available adult human bone marrow samples. The cells are grown in DMEM, 10% FBS, GPS. Immunophenotype, growth rates and multi-lineage differentiation capability were verified for use in these studies.

Immunohistochemistry, Immunofluorescence and Western Blots.

Human-specific CD31 (DakoCytomation) immunostaining was performed as described (MeleroMartin et al., 2007), (Roelofs et al., 2003). PhosphoAKT/VE-cadherin double immunofluorescence was done on cryosections. Slides were fixed with 8% paraformaldehyde, blocked with 1% BSA and incubated with anti-VE-Cadherin (goat, Santa Cruz Biotechnology, Santa Cruz, Calif.) 1:100 for one hour, followed by anti-goat Texas-Red (Vector Labs, Burlingame, Calif.) 1:200. Following an additional blocking step (1% BSA, 0.1% Triton-X), AntipAKT (mouse, Cell Signaling, Danvers, Mass.) 1:100, was applied over night in 4° C. and next, anti-mouse Alexa Fluor 488 (Invitrogen) 1:300 for one hour. PCNA immunostaining was done using anti-PCNA 1:500 (mouse, Santa Cruz Biotechnology, Santa-Cruz, Calif.). For immunostaining of paraffin-embedded Matrigel explants, antigen retrieval was done by citrate buffer. Sections were blocked by 5% horse serum and incubated with a secondary anti-mouse horseradish peroxidase (HRP) conjugate at 1:300 (Vector Labs, Burlingame, Calif.). For immunofluorescence, cells were fixed with methanol, blocked by 1% BSA. Anti-mouse IgG Alexa Fluor 488-conjugate (Invitrogen) 1:300 was used as a secondary antibody. For quantitative PCNA immunostaining, following image capture by automated laser microscopy, the percent of positively stained cells/total cells was determined for each well (n=8 wells/condition) using MetaXpress Software. Phalloidin staining of cells was done using an Alexa Fluor 488-phalloidin conjugate (Invitrogen, Carlsbad, Calif.). Antibodies for western blots were as follows: SM22 (goat, Abcam, 1:1000), αSMA (mouse, Sigma, 1:2000) and tubulin (mouse, Sigma, 1:5000). Western blotting was performed as described (Melero-Martin et al., 2008).

Angiogenic Cytokine Antibody Array. Conditioned media from HemSCs and HemECs, treated or untreated with dexamethasone or Rapamycin, were analyzed for protein expression using RayBio® Human Angiogenesis Antibody Array C Series 1000 (RayBiotech;) according to the manufacturer's instructions. Blots were analyzed by with image J software (NIH).

ELISA.

An enzyme-linked immunoassay (ELISA) was performed using Quantikine Human VEGF and PLGF (R&D Systems).

Quantitative Real-Time PCR Analyses.

A quantitative real-time reverse transcriptase-PCR (RT-PCR) assay was done using Opticon 2 (MJ Research, Taunton, Mass.) with the following primer pairs VEGF-A: 5'-GC-CTTGCCGCCTTGCTGCTCTA-3' (SEQ ID NO: 3)

5'-GTGCTGGCCTTGGTGAGG-3' (SEQ ID NO: 4) PLGF 5'-CCACTCAGCTCTTCTCCT-3' (SEQ ID NO: 5) 5'-AGGGTACCACTTCCACCT-3' (SEQ ID NO: 6) Angiogenin 5'-GGGCGTTTTGTTGTTGGTCT-3' (SEQ ID NO: 7) 5'-GCGCTTGTTGCCATGAATAA3' (SEQ ID NO: 8) C/EBP-α A 5'-GATAAAGCCAAACAACGCAACG-3' (SEQ ID NO: 9) 5'-CTAGAGATCCAGCGACCCGAA-3' (SEQ ID NO: 10) Lipoprotein lipase 5'-TAACTACCCCTA-GACAACGTCCA-3' (SEQ ID NO: 11) 5'-AAGAGAT-GAATGGAGCGCTCG-3' (SEQ ID NO: 12) GAPDH 5'-TG-CACCACCAACTGCTTAG-3' (SEQ ID NO: 13) 5'-GATGCAGGGATGATGTTC-3' (SEQ ID NO: 14) SM22 5'-CATGGTCTTCAAGCAGATGG-3' (SEQ ID NO: 15) 5'-CTGCGCTTTCTTCATAAACC-3' (SEQ ID NO: 16) Calponin 5'-CCCAGAAGTATGACCACCAG-3' (SEQ ID NO: 17) 5'-GCAGCTTATTGATGAATTCGC-3' (SEQ ID NO: 18) NG-2 5'-CCTGGAGAATGGTGGAAGAG-3' (SEQ ID NO: 19) 5'-CTGTGTTTGTAGTGAGGATGG-3' (SEQ ID NO: 20) smMHC 5'-AGAAGCCAGGGAGAAG-GAAACCAA-3' (SEQ ID NO: 21) 5'-TGGAGCTGACCAG-GTCTTCCATTT-3' (SEQ ID NO: 22) PDGFR-β 5'-CG-GAAATAACTGAGATCACCA-3' (SEQ ID NO: 23), 5'-TTGATGGATGACACCTGGAG-3' (SEQ ID NO: 24).

Calcium Influx Assay and Imaging by Fluorescence Microscopy.

To monitor cellular calcium influxes, HemSC treated with Rapamycin (20 ng/ml) or DMSO for six days were labeled with a single wavelength calcium dye, Fluo-4 (1 µM, Molecular Probes), by incubation in 5% CO2 at 37° C. for 20 min. The cells were then rinsed three times with PBS and kept in a calcium solution containing 127 mM NaCl, 3 mM KCl, 2 mM $CaCl_2$, 1 mM $MgCl_2$, 10 mM Hepes, and 20% FBS at pH 7.4 for the duration of the calcium experiments. Fluorescence intensity at a single wavelength (488 nm excitation) over time was followed using a Nikon Eclipse TE-2000-E Fluorescence microscope equipped with a 1000 W High Pressure Mercury Burner (Olympus Optical Company). Alterations in intracellular calcium were quantified by measuring changes in fluorescence intensity in a region of interest drawn over the entire cell including the nucleus. Background fluorescence was subtracted from fluorescence values at each time point. Results are presented as F/Fo, where F is the average fluorescence intensity in the region of interest (ROD at each time point during time lapse imaging, and Fo is the fluorescence intensity in the ROI at time=0. Images (exposed for 250 ms) were recorded every 15 seconds using a Coolsnap HQ CCD camera (Photometrics) and IPLab imaging software (BD Biosciences Bioimaging). Nifedipine (10 uM, Sigma) was added at frame 20. All experiments were performed at room temperature.

Endothelial Proliferation Assays.

cbEPCs at passages 6-10 were plated in 384-well plates at 1000 cells per well. 24 hours later, media was removed and replaced with EBM-2 5% fetal bovine serum media containing the recombinant human proteins VEGF-A at 37.5 ng/ml (R&D Systems) or PlGF-1 at 37.5 ng/ml (R&D Systems), and the drug compounds Rapamycin (20 ng/ml), Everolimus 20 ng/ml or Temsirolimus 200 ng/ml in replicates of 32. 48 hours later, cells were fixed and stained with Hoechst (Invitrogen). Following image capture by automated fluorescence microscopy, cell number was determined using MetaXpress Software.

REFERENCES

All references are incorporated herein by reference in their entirety.

1. Amir J, Metzker A, Krikler R, Reisner S H (1986) Strawberry hemangioma in preterm infants. *Pediatr Dermatol* 3:331-2.
2. Bennett M L, Fleischer A B, Jr., Chamlin S L, Frieden I J (2001) Oral corticosteroid use is effective for cutaneous hemangiomas: an evidence-based evaluation. *Arch Dermatol* 137:1208-13.
3. Boon L M, MacDonald D M, Mulliken J B (1999) Complications of systemic corticosteroid therapy for problematic hemangioma. *Plast Reconstr Surg* 104:1616-23.
4. Boscolo E, Stewart C L, Greenberger S, Wu J K, Durham J T, Herman I M, et al. (2011) JAGGED1 Signaling Regulates Hemangioma Stem Cell-to-Pericyte/Vascular Smooth Muscle Cell Differentiation. *Arterioscler Thromb Vasc Biol*. July 14 [Epub ahead of print] PMID 21757656.
5. Boye E, Yu Y, Paranya G, Mulliken J B, Olsen B R, Bischoff J (2001) Clonality and altered behavior of endothelial cells from hemangiomas. *J Clin Invest* 107:745-52.
6. Chen C, Liu Y, Liu R, Ikenoue T, Guan K L, Liu Y, et al. (2008) TSC-mTOR maintains quiescence and function of hematopoietic stem cells by repressing mitochondrial biogenesis and reactive oxygen species. *J Exp Med* 205:2397-408.
7. Darlington G J, Ross S E, MacDougald O A (1998) The role of C/EBP genes in adipocyte differentiation. *J Biol Chem* 273:30057-60.
8. De Azevedo W F, Leclerc S, Meijer L, Havlicek L, Strnad M, Kim S H (1997) Inhibition of cyclin-dependent kinases by purine analogues: crystal structure of human cdk2 complexed with roscovitine. *Eur J Biochem* 243:518-26.
9. Drolet B A, Esterly N B, Frieden H (1999) Hemangiomas in children. *N Engl J Med* 341:173-81.
10. Dubrovska A, Kim S, Salamone R J, Walker J R, Maim S M, Garcia-Echeverria C, et al. (2009) The role of PTEN/Akt/PI3K signaling in the maintenance and viability of prostate cancer stem-like cell populations. *Proc Natl Acad Sci USA* 106:268-73.
11. Frieden U, Drolet B A (2009) Propranolol for infantile hemangiomas: promise, peril, pathogenesis. *Pediatr Dermatol* 26:642-4.
12. Geerts A M, Vanheule E, Van Vlierberghe H, Leybaert L, Van Steenkiste C, De Vos M, et al. (2008) Rapamycin prevents mesenteric neo-angiogenesis and reduces splanchnic blood flow in portal hypertensive mice. *Hepatol Res* 38:1130-9.
13. Greenberger S, Boscolo E, Adini I, Mulliken J B, Bischoff J (2010) Corticosteroid suppression of VEGF-A in infantile hemangioma-derived stem cells. *N Engl J Med* 362:1005-13.
14. Groszer M, Erickson R, Scripture-Adams D D, Lesche R, Trumpp A, Zack J A, et al. (2001) Negative regulation of neural stem/progenitor cell proliferation by the Pten tumor. suppressor gene in vivo. *Science* 294:2186-9.
15. Guba M, von Breitenbuch P, Steinbauer M, Koehl G, Flegel S, Hornung M, et al. (2002) Rapamycin inhibits primary and metastatic tumor growth by antiangiogenesis: involvement of vascular endothelial growth factor. *Nat Med* 8:128-35.
16. Haggstrom A N, Lammer E J, Schneider R A, Marcucio R, Frieden H (2006) Patterns of infantile hemangiomas: new clues to hemangioma pathogenesis and embryonic facial development. *Pediatrics* 117:698-703.
17. Hall P A, Levison D A (1990) Review: assessment of cell proliferation in histological material. *J Clin Pathol* 43:184-92.
18. Hara K, Yonezawa K, Kozlowski M T, Sugimoto T, Andrabi K, Weng Q P, et al. (1997) Regulation of eIF-4E BP1 phosphorylation by mTOR. *J Biol Chem* 272:26457-63.

19. Hill R, Wu H (2009) PTEN, stem cells, and cancer stem cells. *J Biol Chem* 284:11755-9.
20. Hirschi K K, Rohovsky S A, D'Amore P A (1998) PDGF, TGF-beta, and heterotypic cell-cell interactions mediate endothelial cell-induced recruitment of 10T1/2 cells and their differentiation to a smooth muscle fate. *J Cell Biol* 141:805-14.
21. Ingram D A, Caplice N M, Yoder M C (2005) Unresolved questions, changing definitions, and novel paradigms for defining endothelial progenitor cells. *Blood* 106:1525-31.
22. Ingram D A, Mead L E, Tanaka H, Meade V, Fenoglio A, Mortell K, et al. (2004) Identification of a novel hierarchy of endothelial progenitor cells using human peripheral and umbilical cord blood. *Blood* 104:2752-60.
23. Inoue-Narita T, Hamada K, Sasaki T, Hatakeyama S, Fujita S, Kawahara K, et al. (2008) Pten deficiency in melanocytes results in resistance to hair graying and susceptibility to carcinogen-induced melanomagenesis. *Cancer Res* 68:5760-8.
24. Khan Z A, Boscolo E, Picard A, Psutka S, Melero-Martin J M, Bartch T C, et al. (2008) Multipotential stem cells recapitulate human infantile hemangioma in immunodeficient mice. *J Clin Invest* 118:2592-9.
25. Khan Z A, Melero-Martin J M, Wu X, Paruchuri S, Boscolo E, Mulliken J B, et al. (2006) Endothelial progenitor cells from infantile hemangioma and umbilical cord blood display unique cellular responses to endostatin. *Blood* 108:915-21.
26. Kharas M G, Okabe R, Ganis J J, Gozo M, Khandan T, Paktinat M, et al. (2010) Constitutively active AKT depletes hematopoietic stem cells and induces leukemia in mice. *Blood* 115:1406-15.
27. Leaute-Labreze C, Dumas de la Roque E, Hubiche T, Boralevi F, Thambo J B, Taieb A (2008) Propranolol for severe hemangiomas of infancy. *N Engl J Med* 358:2649-51.
28. Li L, Miano J M, Cserjesi P, Olson E N (1996) SM22 alpha, a marker of adult smooth muscle, is expressed in multiple myogenic lineages during embryogenesis. *Circ Res* 78:188-95.
29. Loveless M E, Whisenant J G, Wilson K, Lyshchik A, Sinha T K, Gore J C, et al. (2009) Coregistration of ultrasonography and magnetic resonance imaging with a preliminary investigation of the spatial colocalization of vascular endothelial growth factor receptor 2 expression and tumor perfusion in a murine tumor model. *Mol Imaging* 8:187-98.
30. Meijer L, Borgne A, Mulner O, Chong J P, Blow J J, Inagaki N, et al. (1997) Biochemical and cellular effects of roscovitine, a potent and selective inhibitor of the cyclin-dependent kinases cdc2, cdk2 and cdk5. *Eur J Biochem* 243:527-36.
31. Melero-Martin J M, De Obaldia M E, Kang S Y, Khan Z A, Yuan L, Oettgen P, et al. (2008) Engineering robust and functional vascular networks in vivo with human adult and cord blood-derived progenitor cells. *Circ Res* 103:194-202.
32. Melero-Martin J M, Khan Z A, Picard A, Wu X, Paruchuri S, Bischoff J (2007) In vivo vasculogenic potential of human blood-derived endothelial progenitor cells. *Blood* 109:4761-8.
33. Mulliken J B (1988) Diagnosis and natural history of hemangiomas. In: *Vascular Birthmarks: hemangiomas and malformations* (Mulliken J B, ed), Philadelphia: W B Saunders.
34. Olive K P, Jacobetz M A, Davidson C J, Gopinathan A, McIntyre D, Honess D, et al. (2009) Inhibition of Hedgehog signaling enhances delivery of chemotherapy in a mouse model of pancreatic cancer. *Science* 324:1457-61.
35. Phung T L, Eyiah-Mensah G, O'Donnell R K, Bieniek R, Shechter S, Walsh K, et al. (2007) Endothelial Akt signaling is rate-limiting for rapamycin inhibition of mouse mammary tumor progression. *Cancer Res* 67:5070-5.
36. Prelich G, Tan C K, Kostura M, Mathews M B, So A G, Downey K M, et al. (1987) Functional identity of proliferating cell nuclear antigen and a DNA polymerase-delta auxiliary protein. *Nature* 326:517-20.
37. Roelofs J J, Rowshani A T, van den Berg J G, Claessen N, Aten J, ten Berge U, et al. (2003) Expression of urokinase plasminogen activator and its receptor during acute renal allograft rejection. *Kidney Int* 64:1845-53.
38. Siegfried E C, Keenan W J, Al-Jureidini S (2008) More on propranolol for hemangiomas of infancy. *N Engl J Med* 359:2846; author reply-7.
39. Sindhi R, Seward J, Mazariegos G, Soltys K, Seward L, Smith A, et al. (2005) Replacing calcineurin inhibitors with mTOR inhibitors in children. *Pediatr Transplant* 9:391-7.
40. Sun S, Liu Y, Lipsky S, Cho M (2007) Physical manipulation of calcium oscillations facilitates osteodifferentiation of human mesenchymal stem cells. *FASEB J* 21:1472-80.
41. Wu P A, Mancini A J, Marghoob A A, Frieden U (2008) Simultaneous occurrence of infantile hemangioma and congenital melanocytic nevus: Coincidence or real association? *J Am Acad Dermatol* 58:S16-22.
42. Yilmaz O H, Valdez R, Theisen B K, Guo W, Ferguson D O, Wu H, et al. (2006) Pten dependence distinguishes haematopoietic stem cells from leukaemia-initiating cells. *Nature* 441:475-82
43. Yoder M C, Mead L E, Prater D, Krier T R, Mroueh K N, Li F, et al. (2007) Redefining endothelial progenitor cells via clonal analysis and hematopoietic stem/progenitor cell principals. *Blood* 109:1801-9.
44. Zhang H H, Huang J, Duvel K, Boback B, Wu S, Squillace R M, et al. (2009) Insulin stimulates adipogenesis through the Akt-TSC2-mTORC1 pathway. *PLoS ONE* 4:e6189.
45. Zhang J, Grindley J C, Yin T, Jayasinghe S, He X C, Ross J T, et al. (2006) PTEN maintains haematopoietic stem cells and acts in lineage choice and leukaemia prevention. *Nature* 441:518-22.
46. Zhou J, Su P, Wang L, Chen J, Zimmermann M, Genbacev O, et al. (2009) mTOR supports long-term self-renewal and suppresses mesoderm and endoderm activities of human embryonic stem cells. *Proc Natl Acad Sci USA* 106:7840-5.

TABLE 1

Identification and validation of compounds that exhibit selective inhibition of HemSCs. Chemical compounds identified as positive hits in the screen. Values represent the number of standard deviations below the control, untreated cells obtained for cells treated with ~1 µM of a given compound. Standard deviations were determined from the standard deviation from the average cell number of untreated cells, n = 8 for each treatment combination.

|  | HemSC | BM-MSC |
|---|---|---|
| Nifedipine | −4.23 | −0.71 |
| Antimycin A | −6.74 | −1.82 |
| Chelidonine monohydrate | −4.21 | −2.07 |
| Lycorine hydrochloride | −4.56 | −2.53 |
| Rapamycin | −6.26 | −2.59 |
| Ionomycin | −8.45 | −2.98 |
| LY-294,002 | −4.07 | −2.27 |
| Cerulenin | −6.43 | 0.30 |
| Monensin sodium | −7.99 | −2.97 |

What is claimed herein is:

1. A method of treating a proliferative vascular disorder, the method comprising: administering a mTOR inhibitor; and administering a steroid and a beta blocker, wherein the proliferative vascular disorder is infantile hemangioma.

2. The method of claim 1, wherein the mTOR inhibitor is selected from the group consisting of: everolimus; temisrolimus; and rapamycin.

3. The method of claim 1, wherein the steroid is a corticosteroid.

4. The method of claim 3, wherein the corticosteroid is selected from the group consisting of:

dexamethasone; prednisone; prednisolone; triamcinolone; clobetasol propionate; betamethasone valerate; betamethasone dipropionate; and mometasone furoate.

5. The method of claim 1, wherein the beta-blocker is selected from the group consisting of:

atenolol; nadolol; propranolol and timolol.

6. The method of claim 1, wherein the i) mTOR inhibitor and ii) the steroid or beta-blocker are administered concomitantly.

7. The method of claim 1, wherein one or more of the mTOR inhibitor, steroid, or beta-blocker are administered systemically.

8. The method of claim 1, wherein one or more of the mTOR inhibitor, steroid, or beta-blocker are administered orally.

9. The method of claim 1, wherein one or more of the mTOR inhibitor, steroid, or beta-blocker are administered intralesionally.

10. The method of claim 1, wherein one or more of the mTOR inhibitor, steroid, or beta-blocker are administered topically.

11. The method of claim 1, wherein the mTOR inhibitor; steroid; and optionally, the beta-blocker are administered for 1 week.

12. The method of claim 1, wherein the mTOR inhibitor; steroid; and optionally, the beta-blocker are administered for 2 weeks.

13. The method of claim 1, wherein the mTOR inhibitor; steroid; and optionally, the beta-blocker are administered for 3 weeks.

14. The method of claim 1, wherein the mTOR inhibitor; steroid; and optionally, the beta-blocker are administered for 4 weeks.

* * * * *

UNITED STATES PATENT AND TRADEMARK OFFICE
CERTIFICATE OF CORRECTION

PATENT NO. : 9,220,716 B2  
APPLICATION NO. : 13/558850  
DATED : December 29, 2015  
INVENTOR(S) : Joyce Bischoff et al.

Page 1 of 1

It is certified that error appears in the above-identified patent and that said Letters Patent is hereby corrected as shown below:

In the Specification

At Column 1, Lines 15-18, please delete "This invention was made with federal funding under Grant Nos. R01 HL096384 and P01 AR48564 awarded by the National Institutes of Health. The U.S. government has certain rights in the invention." and insert the following text:
-- This invention was made with government support under grant number AR048564 awarded by the National Institutes of Health. The Government has certain rights in the invention. --

Signed and Sealed this
Eleventh Day of June, 2019

Andrei Iancu
*Director of the United States Patent and Trademark Office*

UNITED STATES PATENT AND TRADEMARK OFFICE
CERTIFICATE OF CORRECTION

PATENT NO. : 9,220,716 B2
APPLICATION NO. : 13/558850
DATED : December 29, 2015
INVENTOR(S) : Joyce Bischoff et al.

It is certified that error appears in the above-identified patent and that said Letters Patent is hereby corrected as shown below:

In the Specification

At Column 1, Lines 15-18:
"This invention was made with government support under grant number AR048564 awarded by the National Institutes of Health. The Government has certain rights in the invention."
Should be replaced with:
-- This invention was made with government support under Grant nos. AR048564 and HL096384, awarded by The National Institutes of Health. The government has certain rights in the invention. --

This certificate supersedes the Certificate of Correction issued June 11, 2019.

Signed and Sealed this
Thirty-first Day of March, 2020

Andrei Iancu
*Director of the United States Patent and Trademark Office*